US011826361B2

(12) United States Patent
Hayden et al.

(10) Patent No.: US 11,826,361 B2
(45) Date of Patent: Nov. 28, 2023

(54) USE OF PRIDOPIDINE FOR TREATING DYSTONIAS

(71) Applicant: PRILENIA THERAPEUTICS DEVELOPMENT LTD., Herzliya (IL)

(72) Inventors: Michael Hayden, Herzliya (IL); Spyridon Papapetropoulos, Wellesley Hills, MA (US); Juha-Matti Savola, Reinach (CH); Eli Eyal, Petah-Tikva (IL); Beth Borowsky, Flemington, NJ (US); Igor D. Grachev, Millstone Township, NJ (US); Mark Forrest Gordon, Jericho, NY (US)

(73) Assignee: PRILENIA NEUROTHERAPEUTICS LTD, Yakum (IL)

( * ) Notice: Subject to any disclaimer, the term of this patent is extended or adjusted under 35 U.S.C. 154(b) by 0 days.

(21) Appl. No.: 16/283,784

(22) Filed: Feb. 24, 2019

(65) Prior Publication Data
US 2019/0192496 A1    Jun. 27, 2019

Related U.S. Application Data

(63) Continuation-in-part of application No. PCT/US2017/048458, filed on Aug. 24, 2017.

(60) Provisional application No. 62/395,319, filed on Sep. 15, 2016, provisional application No. 62/379,175, filed on Aug. 24, 2016.

(51) Int. Cl.
  *A61K 31/451* (2006.01)
  *A61P 21/00* (2006.01)
  *A61K 9/00* (2006.01)

(52) U.S. Cl.
  CPC .......... *A61K 31/451* (2013.01); *A61K 9/0053* (2013.01); *A61P 21/00* (2018.01)

(58) Field of Classification Search
  CPC ...... A61K 31/451; A61K 9/0053; A61P 21/00
  See application file for complete search history.

(56) References Cited

U.S. PATENT DOCUMENTS

| 6,903,120 | B2 * | 6/2005 | Sonesson ........... C07D 295/155 514/331 |
|---|---|---|---|
| 2003/0139423 | A1 | 7/2003 | Sonesson et al. |
| 2006/0135531 | A1 | 6/2006 | Sonesson et al. |
| 2007/0238879 | A1 | 10/2007 | Gauthier et al. |
| 2007/0270467 | A1 | 11/2007 | Sonesson et al. |
| 2008/0234321 | A1 | 9/2008 | Sonesson |
| 2010/0105736 | A1 | 4/2010 | Wikström |
| 2011/0082397 | A1 * | 4/2011 | Alberts ............. A63B 24/0087 601/26 |
| 2013/0150406 | A1 | 6/2013 | Zimmermann et al. |
| 2013/0197031 | A1 | 8/2013 | Sonesson |
| 2013/0267469 | A1 | 10/2013 | Matson |
| 2013/0267552 | A1 | 10/2013 | Waters et al. |
| 2014/0037850 | A1 | 2/2014 | Buckley, Jr. et al. |
| 2014/0315951 | A1 | 10/2014 | Sonneson et al. |
| 2014/0378508 | A1 * | 12/2014 | Bassan ................ A61P 25/14 514/315 |
| 2015/0202302 | A1 * | 7/2015 | Licht ................... A61K 9/2054 514/317 |
| 2015/0209344 | A1 | 7/2015 | Zimmermann et al. |
| 2015/0374677 | A1 | 12/2015 | Schmidt et al. |
| 2016/0095847 | A1 | 4/2016 | Sonesson |
| 2016/0166559 | A1 | 6/2016 | Sonesson |
| 2016/0176821 | A1 | 6/2016 | Wu et al. |
| 2016/0243098 | A1 | 8/2016 | Geva et al. |
| 2017/0020854 | A1 | 1/2017 | Licht et al. |
| 2017/0022158 | A1 | 1/2017 | Barel et al. |
| 2017/0266170 | A1 | 9/2017 | Waters et al. |
| 2018/0055832 | A1 | 3/2018 | Hayden et al. |
| 2018/0235950 | A1 | 8/2018 | Sonesson |
| 2019/0015401 | A1 | 1/2019 | Sonesson |
| 2019/0030016 | A1 | 1/2019 | Schmidt et al. |
| 2019/0046516 | A1 | 2/2019 | Russ et al. |
| 2019/0209542 | A1 | 7/2019 | Licht et al. |

FOREIGN PATENT DOCUMENTS

| JP | 2019524897 A | 9/2019 |
|---|---|---|
| WO | WO 2001/046145 A1 | 6/2001 |
| WO | WO 2005/121087 A1 | 12/2005 |
| WO | WO 2006/040155 A1 | 4/2006 |
| WO | WO 2008/127188 A1 | 10/2008 |
| WO | WO 2011/107583 | 9/2011 |
| WO | WO 2012/028635 A1 | 3/2012 |
| WO | WO 2013/034622 A1 | 3/2013 |
| WO | WO 2013/152105 A1 | 10/2013 |
| WO | WO 2014/205229 A1 | 12/2014 |
| WO | WO 2015/112601 | 7/2015 |
| WO | WO 2016/003919 A1 | 1/2016 |
| WO | WO 2016/138130 A1 | 9/2016 |

(Continued)

OTHER PUBLICATIONS

Tedroff, J et al., Movement Disorders vol. 19 pp. S201. 2004 (Year: 2004).*

(Continued)

*Primary Examiner* — Jared Barsky
(74) *Attorney, Agent, or Firm* — Mark S. Cohen; PEARL COHEN ZEDEK LATZER BARATZ LLP

(57) ABSTRACT

The invention provides a method of treating a subject afflicted with a dystonia, comprising periodically administering to the subject a pharmaceutical composition comprising an amount of pridopidine effective to treat the subject.

14 Claims, 35 Drawing Sheets

(56) References Cited

FOREIGN PATENT DOCUMENTS

| WO | WO 2016/138135 A1 | 9/2016 |
| WO | WO 2017/015609 A1 | 1/2017 |
| WO | WO 2017/015615 A1 | 1/2017 |
| WO | WO 2017/147366 A1 | 8/2017 |
| WO | WO 2018/039477 A1 | 3/2018 |
| WO | WO 2018/053275 A1 | 3/2018 |
| WO | WO 2018/053280 A1 | 3/2018 |
| WO | WO 2018/053287 A1 | 3/2018 |
| WO | WO 2018/136600 A1 | 7/2018 |
| WO | WO 2019/036358 A1 | 2/2019 |
| WO | WO 2019/050775 A1 | 3/2019 |

OTHER PUBLICATIONS

Reagan Shaw et al (FASEBJ vol. 22 pp. 659-661 published 2007). (Year: 2007).*
Tedroff (Movement Disorders vol. 19 p. S201-S202 published 2004) (Year: 2004).*
Varanese (Parkinson's disease vol. 2010) (Year: 2010).*
Burke et al (Neurology vol. 35 pp. 73-77 pp. 1985) (Year: 1985).*
Yebenes et al., "Pridopidine for the treatment of motor function in patients with Huntington's disease (MermaiHD): a phase 3, randomised, double-blind, placebo-controlled trial," the Lancet vol. Dec. 10, 2011.*
Albanese, "Dystonia rating scales: critique and recommendations," Mov Disord. Jun. 15, 2013; 28(7): 874-883.*
Albanese et al. "A systematic review on the diagnosis and treatment of primary (idiopathic) dystonia and dystonia plus syndromes: report of an EFNS/MDS-ES Task Force" European journal of neurology. May 2006;13(5):433-44.
Albanese et al. Phenomenology and classification of dystonia: a consensus update: Movement disorders. Jun. 15, 2013;28(7):863-73.
Albanese et al. "Dystonia rating scales: critique and recommendations, Movement Disorders" Jun. 15, 2013;28(7):874-83.
Bechtel et al. "Tapping linked to fuction and structure in premanifest and symptomatic Huntington disease" Neurology, Dec. 14, 2010;75(24):2150-60.
Bowie et al. "Administration and interpretation of the Trail Making Test" Nature protocols. Dec. 2006;1(5):2277.
Brown et al. "Physical and performance measures for the identification of mild to moderate failty" The Journals of Gerontology Series A: Biological Sciences and Medical Sciences. Jun. 1, 2000;55(6):M350-5.
"Coenzyme Q10 in Huntington's Disease (HD) (2CARE)", ClinicalTrials.gov Identifier: NCT00608881, clinicaltrials.gov/ct2/show/NCT00608881?term=2CARE%20+Huntington&rank=1, accessed Sep. 13, 2016.
Craufurd et al. "Behavioral changes in Huntington disease" Cognitive and Behavioral Neurology. Oct. 1, 2001;14(4):219-26.
"Exploratory Population Pharmacokinetic Modeling and Simulations with Pridopidine" (Report No. CP-13-013). Pharsight Consulting Services, Jul. 10, 2013.
Group TE. "EuroQol—a new facility for the measurement of health-related quality of life" Health policy. Dec. 1, 1991;16(3):199-208.
Guy W. "Clinical global impression. Assessment manual for Psychopharmacology" 1976:217-22.
Hocaoglu et al. "The Huntington's Disease health-related Quality of Life questionnaire (HDQoL): a disease-specific measure of health-related quality of life" Clinical genetics. Feb. 2012;81(2):117-22.
Huntington Study Group TREND-HD Investigators. "Randomized controlled trial of ethyl-elcosapentaenoic acid in Huntington disease" Archives of neurology. Jan. 1, 2008;65(12):1582-9.
Huntington HS. Unified Huntington's disease rating scale: reliability and consistency. Movement Disorders. 1996;11:136-42.
Huntington Study Group. "Dosage effects of riluzole in Huntington's disease: a multicenter placebo-controlled study" Neurology. Dec. 9, 2003;61(11):1551-6.
Huntington Study Group. "Tetrabenazine as antichorea therapy in Huntington disease: a randomized controlled trial" Neurology. Feb. 14, 2006;66(3):366-72.
Huntington Study Group. "A randomized, placebo-controlled trial of coenzyme Q10 and remacemide in Huntington's disease" Neurology. Aug. 14, 2001;57(3):397-404.
International Search Report for PCT Application No. PCT/US2017/048458 dated Nov. 9, 2017.
Joffres et al. "Qualitative analysis of the clinician interview-based impression of change (Plus): methodological issues and implications for clinical research" International psychogeriatrics. Sep. 2000;12(3):403-13.
Johnson et al. "Understanding Behavior in Huntington's Disease: A Guide for Professionals" New York: Huntington's Disease Society of America. 2014.
Kingma et al. "Behavioural problems in Huntington's disease using the Problem Behaviours Assessment" General hospital psychiatry. Mar. 1, 2008;30(2):155-61.
Liang et al. "TorsinA hypofunction causes abnormal twisting movements and sensorimotor circuit neurodegeneration" The Journal of clinical Investigation. Jul. 1, 2014;124(7):3080-92.
Mahant et al "Huntington Study Group. Huntington's disease: clinical correlates of disability and progression" Neurology. Oct. 28, 2003;61(8):1085-92.
Marder et al. "Rate of functional decline in Huntington's disease" Neurology. Jan. 25, 2000;54(2):452-479.
Mestre et al. "Therapeutic interventions for symptomatic treatment in Huntington's disease" Cochrane Database of Systematic Reviews. 2009(3).
Myers et al. "Factors associated with slow progression in Huntington's disease" Archives of neurology. Aug. 1, 1991;48(8):800-4.
Natesan, Sridhar, et al. The dopamine stabilizers (S)-(−)-(3-methanesulfonyl-phenyl)-1-propyl-piperidine [(=)-OSU6162] and 4-(3-methanesulfonylphenyl)-1-propyl-piperidine (ACR16) show high in vivo D2 receptor occupancy, antipsychotic-like efficacy, and low potential for motor side effects in the rat. *Journal of Pharmacology and Experimental Therapeutics*, 2006, 318.2: 810-818.
"Open-label Extension Study of Pridopidine (ACR16) in the Symptomatic Treatment of Huntington Disease (OPEN-HART)", ClinicalTrials.gov Identifier: NCT01306929, clinicaltrials.gov/ct2/show/NCT01306929, accessed Sep. 13, 2016.
Ozelius et al. "DYT1 early-onset isolated dystonia" In GeneReviews® [Internet] Nov. 17, 2016. University of Washington, Seattle.
Ozelius et al. "The early-onset torsion dystonia gene (DYT1) encodes an ATP-binding protein" Nature genetics. Sep. 1997;17(1):40.
Podsiadlo et al. "The timed "Up & Go": a test of basic functional mobility for frail elderly persons" Journal of the American geriatrics Society. Feb. 1991;39(2):142-8.
Ponten et al. "In vivo pharmacology of the dopaminergic stabilizer pridopidine" European journal of pharmacology. Oct. 10, 2010;644(1):88-95.
Rao et al. "Clinical measurement of mobility and balance impairments in Huntington's disease: validity and responsiveness" Gait & posture. Apr. 1, 2009;29(3):433-6.
Segawa et al. "Genetics and pathophysiology of primary dystonia with special emphasis on DYT1 and DYT5" In Seminars in neurology Jul. 2014 (vol. 34, No. 03, pp. 306-311). Thieme Medical Publishers.
Standaert DG. "Update on the pathology of dystonia" Neurobiology of disease. May 1, 2011;42(2):148-51.
Verbeek et al. "Unmet Needs in Dystonia: Genetics and Molecular Biology—How Many Dystonias?" Frontiers in neurology. Jan. 16, 2017;7:241.
Bressman, S.B. et al. (Jan. 1996)—Exclusion of the DYT1 locus in familial torticollis. Annals of Neurology, vol. 40, No. 4, pp. 681-684.
De Yebenes, J. G. et al. (2011)—Pridopidine for the treatmmt of motor function in patients with Huntington's disease (MermaiHD): a phase 3, randumized, dauble-blind, placebo-controlled trial. The Lancet Neurolog, vol. 10, not 12, p. 1049-1057.

(56) References Cited

OTHER PUBLICATIONS

Geva, M. et al. (2016)—Pridopidine activates neuroprotective pathways imgaired in Huntingten Disease—Human molecular genetics, 25(18), 3975-3987.

Hasegawa, O. (Sep. 2015)—Professional dystonia of musicians, Journal of Japan Physicians Associatian, vol. 30 No. 2, p. 175, Japan Physicians Association, Tokyo, Japan.

Huntington Study Group Hart Investigators (2013)—A randomized, double-blind, placebo-controlled trial of pridopidine in Huntington—s disease. Movement Disorders, vol. 28, not 10, pp. 1407-1415. First published Feb. 28, 2013.

International Search Report for PCT/US2017/048458 dated Nov. 9, 2017.

Kawarai, T., et al. (2013). Dystonia genes and elucidation of their roles in dystonia pathogenesis. *Rinsho Shinkeigaku=Clinical Neurology*, 53(6), 419-429.

Martin, M. et al. (Jul. 2013)—Pridopidine in the pharmacological treatment of Huntington's disease. Clinical Investigation, vol. 3, No. 7, pp. 691-699, UK.

Rabinovich-Guilatt et al. (2016)—The effect of mild and moderate renal impairment on the pharmocokinetics of pridopidine, a new drug for Huntington's disease—British journal of clinical pharmacology, 81(2), 246-255.

Ryskamp, D. et al. (2017)—The sigma-1 receptor mediates the beneficial effects of pridopidine in a mouse model of Huntington disease—Neurobiology of disiease, 97, 46-59.

Squitieri, F. et al. (Oct. 2015)—Profile of pridopidine and its potential in the treatment of Huntington disease: The evidence to date. Drug Design, Development and Therapy, p. 5827, UK.

Supplementary European Search Report for EP17844432.9 dated Apr. 2, 2020.

Badhwar, AmanPreet, et al. Resting-state network dysfunction in Alzheimer's disease: a systematic review and meta-analysis. *Alzheimer's & Dementia: Diagnosis, Assessment & Disease Monitoring*, 2017, 8: 73-85.

Comella, Cynthia L., et al. Rating scales for dystonia: a multicenter assessment. *Movement disorders*, 2003, 18.3: 303-312.

Delnooz, Cathérine CS, et al. Task-free functional MRI in cervical dystonia reveals multi-network changes that partially normalize with botullinum toxin. *Plos one*, 2013, 8.5: e62877.

Folstein, Marshal F.; Robins, Lee N.; Helzer, John E. The minimental state examination. Archives of general psychiatry, 1983, 40.7: 812-812.

Goveas, Joseph S., et al. Recovery of hippocampal network connectivity correlates with cognitive Improvement in mild Alzheimer's disease patients treated with donepezil assessed by resting-state fMRI. Journal of Magnetic Resonance Imaging, 2011, 34.4: 764-773.

Ikeda, Ken, et al. Donepezil-induced cervical dystonia in Alzheimer's disease: a case report and literature review of dystonia due to cholinesterase inhibitors. Internal Medicine, 2014, 53.9: 1007-1010.

Jahanshahi, Marjan; Torkamani, Mariam. The cognitive features of idiopathic and DYT1 dystonia. Movement Disorders, 2017, 32.10: 1348-1355.

Lucas-Jiménez, Olaia, et al. Altered functional connectivity in the default mode network is associated with cognitive impairment and brain anatomical changes in Parkinson's disease. Parinsonism & related disorders, 2016, 33: 58-64.

Mohammadi, Bahram, et al. Changes of resting state brain networks in amyotrophic lateral sclerosis. Experimental neurology, 2009, 217.1: 147-153.

Mukku, Shiva Shanker Reddy, et al. Recurrent truncal dystonia (Pisa syndrome) due to donepezil—A case report. Asian journal of psychiatry, 2018, 35: 47-49.

Poewe, W. H.; Lees, A. J.; Stern, G. M. Dystonia in Parkinson's disease: clinical and pharmacological features. Annals of Neurology: Official Journal of the American Neurological Association and the Child Neurology Society, 1988, 23.1: 73-78.

Quarantelli, Mario, et al. Default-mode network changes in Huntington's disease: an integrated MRI study of functional connectivity and morphometry. PloS One, 2013, 8.8: e72159.

Ravina, B., et al. Donepezil for dementia in Parkinson's disease: a randomised, double blind, placebo controlled, crossover study. Journal of Neurology, Neurosurgery & Psychiatry, 2005, 76.7: 934-939.

Rogers, S. L., et al. A 24-week, double-blind, placebo-controlled trial of donepezil in patients with Alzheimer's disease. Neurology, 1998, 50.1: 136-145.

Shetty, Aakash S.; Bhatia, Kailash P.; Lang, Anthony E. Dystonia and Parkinson's disease: what is the relationship?. Neurobiology of disease, 2019, 132: 104462.

Smith, Verity; Mitchell, Daniel J.; Duncan, John. Role of the default mode network in cognitive transitions. Cerebral Cortex, 2018, 28.10: 3685-3696.

Stout, Julie C., et al. HD-CAB: A cognitive assessment bbattery for clinical trials in Huntington's disease1, 2, 3. Movement Disorders, 2014, 29.10: 1281-1288.

Alzheimer's disease (AD)—https://www.alz.org/alzheimers-dementia/10_signs.

Frontotemporal dementia (FTD)—https://www.alz.org/alzheimers-dementia/what-is-dementia/types-of-dementia/frontotemporal-dementia.

Dystonia Treatment in Bangalore—https://www.drsanjivneurobangalore.com/dystonia-treatment-in-bangalore.php.

Greene, P., et al. (1988). Analysis of open-label trials in torsion dystonia using high dosages of anticholinergics and other drugs. Movement disorders: official journal of the Movement Disorder Society, 3(1). 46-60.

Huntington Study Group, (1996). Unified Huntington's disease rating scale: Reliability and consistency. Mov Disord, 11, 136-142.

Huntington Study Group. (2006). Tetrabenazine as antichorea therapy in Huntington disease: a randomized controlled trial. *Neurology*, 66(3), 366-372.

Jankovic. J., & Beach, J. (Feb. 1996). Long-term effects of tetrabenazine in hyperkinetic movement disorders. In *Neurology* (vol. 46, No. 2, pp. 22005-22005).

Tarakad, A. (2020). Clinical rating scales and quantitative assessments of movement disorders. Neurologic clinics, 38(2), 231-254.

Tumas, V., et al. (2004). Internal consistency of a Brazilian version of the unified Huntington's disease rating scale. Arquivos de Neuro-psiquiatria, 62, 977-982.

Michl, M. et al. (2013). Pridopidine in the pharmacological treatment of Huntington's disease. Clinical Investigation, 3(7), 691-699.

Mestre, T. A., et al. Rating scales for cognition in Huntington's disease: critique and recommendations. *Movement Disorders*, 2018, 33(2), 187-195.

\* cited by examiner

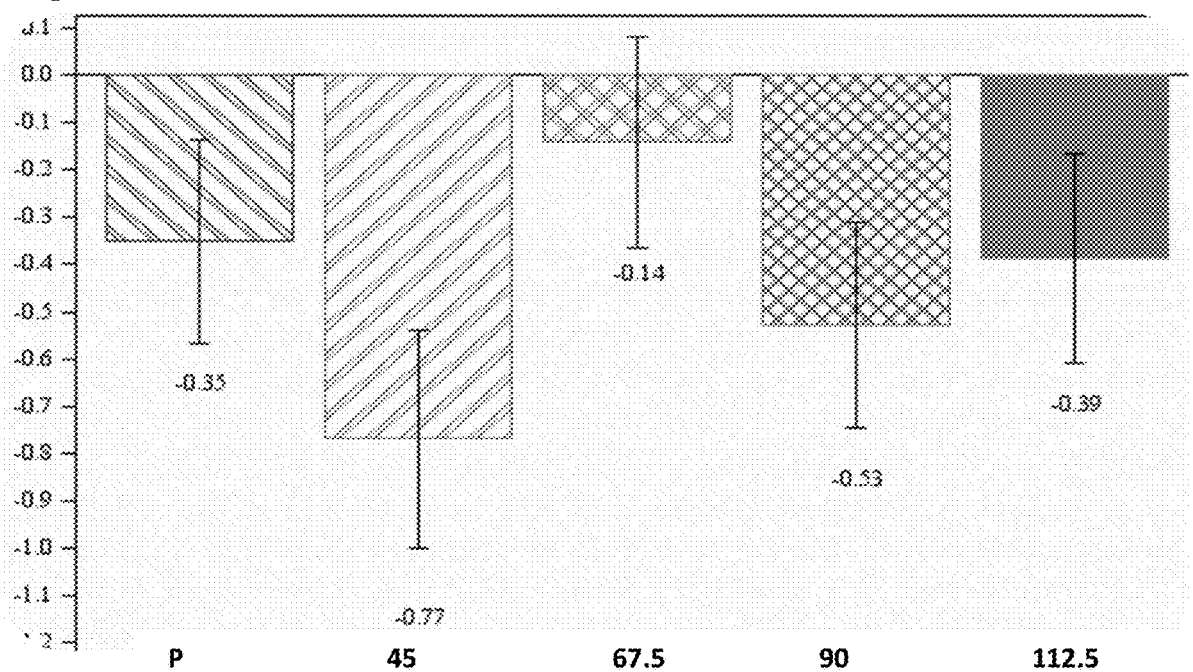

USE OF PRIDOPIDINE FOR TREATING DYSTONIAS

CROSS REFERENCE TO RELATED APPLICATIONS

This application is a Continuation-in-Part Application from PCT/US2017/048458 filed 24 Aug. 2017, which claims the benefit of U.S. Provisional Application No. 62/395,319, filed Sep. 15, 2016 and U.S. Provisional Application No. 62/379,175, filed Aug. 24, 2016, the contents of each of which are hereby incorporated by reference in their entirety.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

FIELD OF THE INVENTION

The invention provides a method of treating a subject afflicted with a dystonia, comprising periodically administering to the subject a pharmaceutical composition comprising an amount of pridopidine effective to treat the subject.

BACKGROUND OF INVENTION

Dystonias

Dystonia is a movement disorder characterized by sustained or intermittent muscle contractions of agonist and antagonist muscles causing abnormal, often repetitive movements, postures, or both. Dystonic movements are typically patterned, twisting, and may be tremulous. Dystonia is often initiated or worsened by voluntary action and associated with overflow muscle activation. Dystonia is classified along two axes: clinical characteristics, including age at onset, body distribution, temporal pattern and associated features (additional movement disorders or neurological features), and etiology, which includes nervous system pathology and inheritance (Albanese 2013a).

Dystonia is a dynamic condition that often changes in severity depending on the posture assumed and on voluntary activity of the involved body area. Symptoms may progress into adjacent muscles and vary according to the type and location of the dystonia. Patients with dystonia may experience muscle spasms, cramping, pain, impaired vision (eyelid closure), chewing, speech, or swallowing, loss of coordination, and abnormal posture/gait. This feature of dystonia has challenged the development of rating scales with acceptable clinimetric properties. (Albanese 2013a).

The clinical characteristics of dystonia include: age at onset (from infancy to late adulthood), body distribution (focal, segmental or, generalized), and temporal pattern (static or progressive and variability related to voluntary actions or to diurnal fluctuations). Dystonia can be isolated or combined with another movement disorder, such as parkinsonism or myoclonus, or can be associated with other neurological or systemic manifestations. Isolated dystonia with onset in childhood tends to progress to generalization, whereas dystonia arising in adulthood usually remains focal or segmental.

Despite the identification of genetic mutations associated with dystonias, there remains uncertainty regarding the causative role of those gene variants. Many familial dystonia cases and the majority of sporadic dystonia cases cannot be explained by validated mutations in known dystonia gene. A list of genes for monogenic forms of isolated and combined dystonias is presented in Table 1 of Verbeek and Gasser. (Verbeek 2017). Additional genes responsible for inherited dystonias are listed in Albanese. (Albanese 2013a).

The classification of dystonia has evolved over time. The changing system for categorizing dystonia reflects, in part, an increased understanding of the various clinical manifestations and etiologies, but also the varied opinion on the merits and criteria for grouping certain disorders together. (Albanese 2013a).

The most common hereditary, primary dystonia is DYT1 dystonia caused by a genetic mutation (DYT1) which results in a defect in an ATP-binding protein called Torsin A. Torsin A is expressed at high levels in neuronal cytoplasm of specific neuronal populations in the adult human brain, including the substantia nigra (SN), thalamus, cerebellum, hippocampus, and neostriatum. The defective Torsin A protein creates a disruption in communication in neurons that control muscle movement and muscle control (Ozelius 1997; Albanese 2006).

The most common symptoms of DYT1 dystonia are dystonic muscle contractions causing posturing of a foot, leg, or arm. Dystonia is usually first apparent with specific actions such as writing or walking. Over time, the contractions frequently (but not invariably) become evident with less specific actions and spread to other body regions. No other neurologic abnormalities are present, except for postural arm tremor. Disease severity varies considerably even within the same family. Isolated writer's cramp may be the only sign (Ozelius 1999).

In most instances, DYT1 dystonia symptoms start with a focal dystonia as talipes equinovarus of one leg in early childhood, typically around 6 years of age. The dystonic posturing then gradually progresses with age to other extremities and trunk muscles by the early teens. Dystonia may also start in an arm. There is asymmetry to the dystonia, with involvement of the extremities on the dominant side along with the ipsilateral sternocleidomastoid muscle. In these patients, interlimb coordination and locomotive movements are not affected. Moreover, intellectual, mental, and psychological functions are completely intact in these patients (Ozelius 1997; Ozelius 1999; Albanese 2006).

Based on clinical characteristics, it has been proposed that DYT1 dystonia can be classified into two types: the postural type with appendicular and truncal dystonias, or the action type, which is associated with violent dyskinetic movements in addition to dystonic posture (Segawa 2014).

Pridopidine

Pridopidine (4-[3-(methylsulfonyl)phenyl]-1-propyl-piperidine) (formerly known as ACR16) is a drug under development for treatment of Huntington's disease. Pridopidine has been shown to modulate motor activity by either suppressing hyperactivity or enhancing hypoactivity. The neuroprotective properties of pridopidine are suggested to be attributed to its high affinity to the Sigma-1 receptor (S1R, binding IC50~100 nM), while the motor activity of pridopidine may be mediated primarily by its low-affinity, antagonistic activity at the dopamine D2 receptor (D2R) (binding IC50~10 µM) (Ponten 2010). Pridopidine shows low-affinity binding to additional receptors in the micromolar range.

The S1R is an endoplasmic reticulum (ER) chaperone protein which is implicated in cellular differentiation, neuroplasticity, neuroprotection and cognitive function in the brain. Recently, transcriptomic analysis of rat striatum showed that pridopidine treatment activates expression of the BDNF, dopamine receptor 1 (D1R), glucocorticoid receptor (GR), and the serine-threonine kinase protein kinase B (Akt)/phosphoinositide 3-kinase (PI3K) pathways, known to promote neuronal plasticity and survival and to be impaired in HD. Moreover, pridopidine gene expression profile showed a reversed pattern of the HD disease gene expression profile in a Q175 knock-in (Q175 KI) HD mouse model (Geva 2016). Pridopidine also enhances secretion of the neuroprotective brain-derived neurotrophic factor (BDNF) in a neuroblastoma cell line, in a S1R-dependent manner (Geva 2016).

BRIEF SUMMARY OF THE INVENTION

This invention provides a method of treating a subject afflicted with a dystonia, comprising periodically administering to the subject a pharmaceutical composition comprising an amount of pridopidine effective to treat the subject.

This invention provides a method of treating a subject afflicted with a dystonia comprising periodically administering to the subject a pharmaceutical composition comprising an amount of pridopidine or its pharmaceutically acceptable salt, effective to treat the subject, wherein the dystonia is a primary dystonia, an isolated dystonia, an early onset generalized dystonia, a secondary dystonia, a focal dystonia, a segmental dystonia, a multifocal dystonia, a hemidystonia, a generalized dystonia, paroxysmal dystonia, Blepharospasm (Benign Essential Blepharospasm[BEB]), Cervical Dystonia (Spasmodic Torticollis[ST]), Acquired Dystonia, Oromandibular Dystonia, Embouchure dystonia, Paroxysmal Dystonia Choreoathetosis, Paroxysmal nonkinesigenic dyskinesia (PKND), Spasmodic Dysphonia (SD), Spasmodic Torticollis (Cervical Dystonia), Tardive Dystonia, writer's Cramp dystonia or any combination thereof.

This invention further provides a method of treating a subject afflicted with a dystonia as a symptom of a disorder comprising: Huntington disease, Parkinson disease, Alzheimer disease, Wilson's disease, Multiple Sclerosis, birth injury, disorders that develop in some people with cancer (paraneoplastic syndromes), oxygen deprivation or carbon monoxide poisoning, infections such as HIV, tuberculosis or encephalitis, reactions to certain medications or heavy metal poisoning, comprising periodically administering to the subject a pharmaceutical composition comprising an amount of pridopidine or its pharmaceutically acceptable salt effective to treat the subject or a genetic dystonias.

The invention also provides pridopidine for the manufacture of a medicament for use in treating a subject afflicted with a dystonia.

The invention also provides a pharmaceutical composition comprising an effective amount of pridopidine for treating a dystonia.

The invention also provides a pharmaceutical composition comprising pridopidine for use in treating a subject suffering from a dystonia.

The invention also provides a package comprising:
a) a pharmaceutical composition comprising an amount of pridopidine; and
b) instructions for use of the pharmaceutical composition to treat a subject afflicted with a dystonia.

The invention also provides a therapeutic package for dispensing to, or for use in dispensing to, a subject afflicted with a dystonia, which comprises:
a) one or more unit doses, each such unit dose comprising an amount of pridopidine thereof, wherein the amount of said pridopidine in said unit dose is effective, upon administration to said subject, to treat the subject, and
b) a finished pharmaceutical container therefor, said container containing said unit dose or unit doses, said container further containing or comprising labeling directing the use of said package in the treatment of said subject.

BRIEF DESCRIPTION OF THE SEVERAL VIEWS OF THE DRAWINGS

The present invention is further illustrated by reference to the accompanying drawings. In the following brief descriptions of the figures and the corresponding figures, efficacy was assessed throughout the 52-week period using Mixed Models Repeated Measures (MMRM) analyses of change from baseline in the Unified Huntington's Disease Rating Scale Total Motor Score (UHDRS TMS; TMS), the modified Physical Performance Test (mPPT), individual TMS subscales, functional, cognitive and other outcomes.

Figure 1:
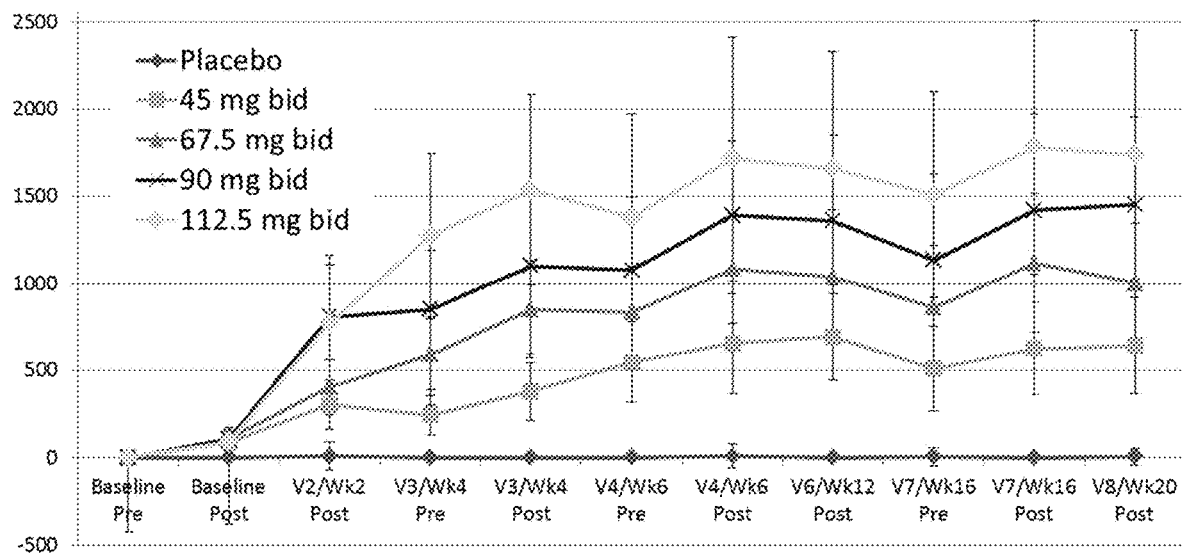
FIG. 1: Pridopidine concentration in patient's blood (ng/mL; Mean (+/'sd) measured values). "Pre" means predose and "post" mean post dose. V2 means visit 2, V3 means visit 3, etc. Wk2 means second week, Wk3 means third week, etc.
Figure 2:
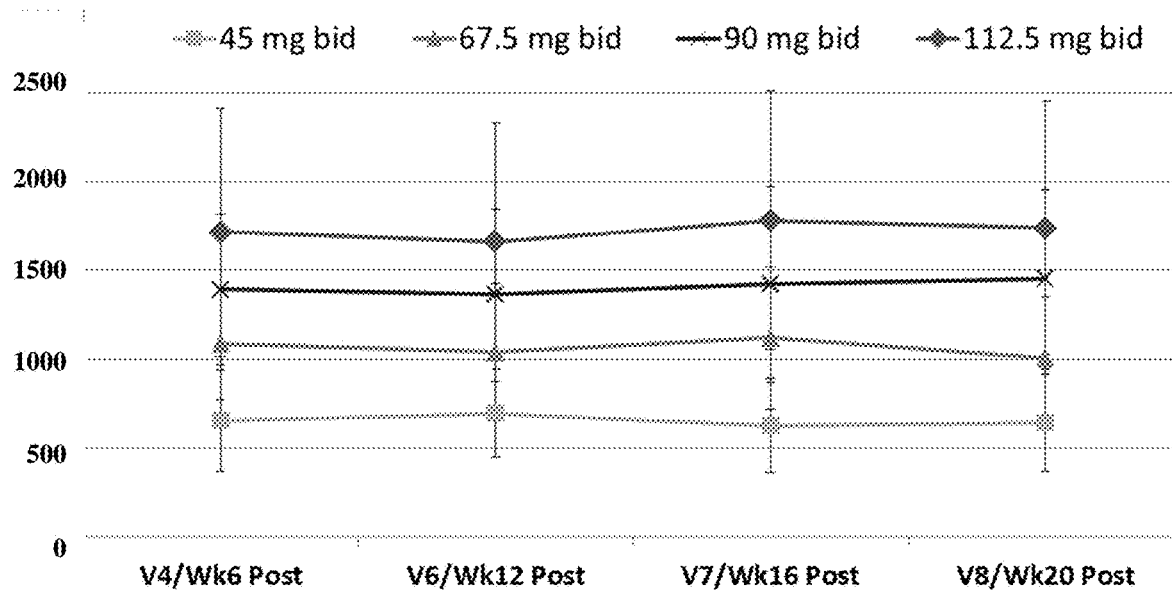
FIG. 2: Pridopidine concentration in patient's blood (ng/mL). Post-dose ("Cmax") (+/−sd) at Steady State.

For FIGS. 1 and 2, a % coefficient of variation (CV) of around 40% for measured values is considered adequate for this setting [1-2 hours post dose, patient population, sparse sampling]. Variability is expected to decrease once true sampling times are taken into consideration.

Figure 3:
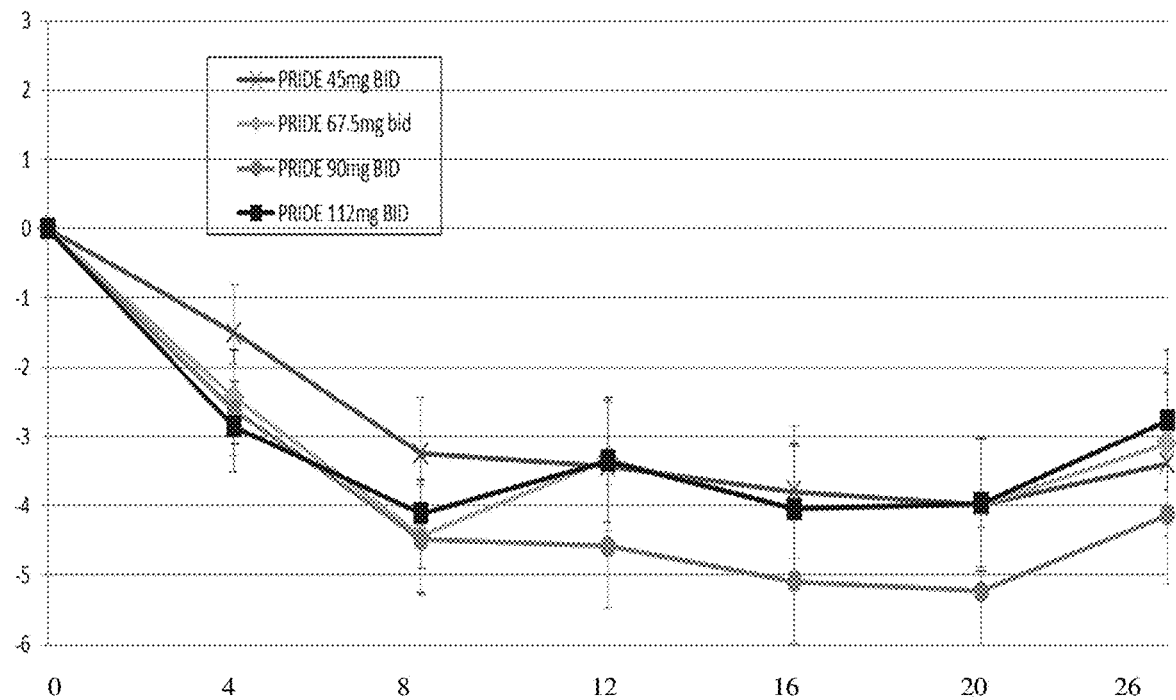

FIG. 3: Total Motor Score (TMS) Change from Baseline (BL) with pridopidine administration. The 90 mg bid dose (circles) demonstrated the largest treatment effect. A decrease in TMS indicates an improvement. Table 1 below shows the P-Values corresponding to FIG. 3.

TABLE 1

| Week | 45 mg bid | 67.5 mg bid | 90 mg bid | 112.5 mg bid |
| --- | --- | --- | --- | --- |
| 4 | 0.0304 | 0.0004 | <.0001 | <.0001 |
| 8 | <.0001 | <.0001 | <.0001 | <.0001 |
| 12 | 0.0002 | 0.0003 | <.0001 | 0.0002 |
| 16 | <.0001 | <.0001 | <.0001 | <.0001 |
| 20 | <.0001 | <.0001 | <.0001 | <.0001 |
| 26 | 0.0013 | 0.0024 | <.0001 | 0.0063 |

Figure 4:
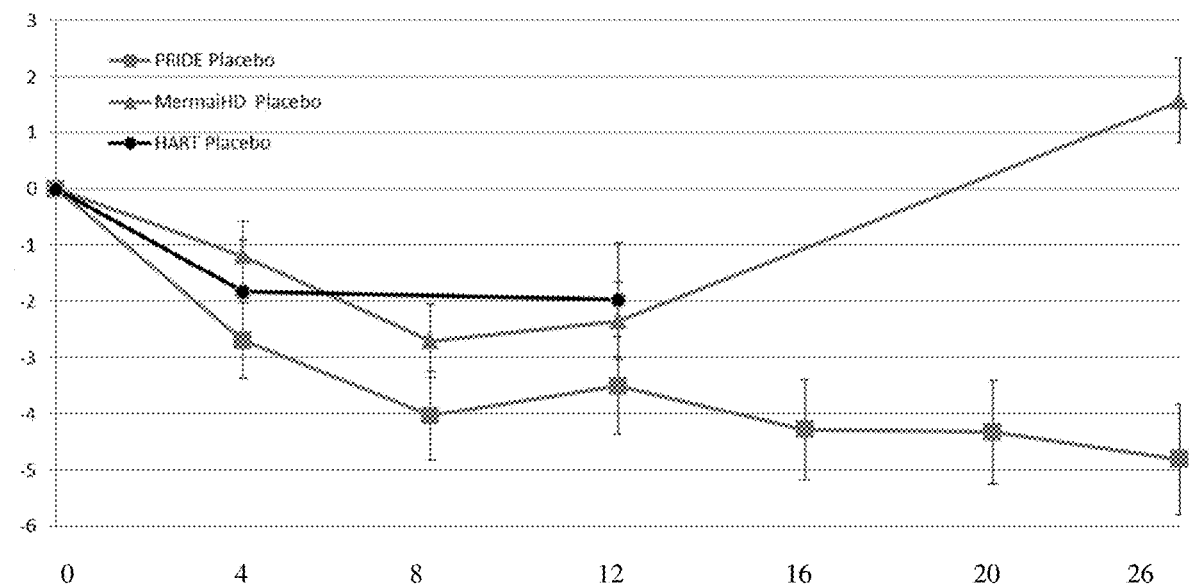

FIG. 4: Total Motor Score (TMS)—Change from Baseline (90 mg pridopidine bid vs historical placebo in HART and MermaiHD clinical trials). There is about a 6.5 TMS point difference at week 26.

Figure 5A:
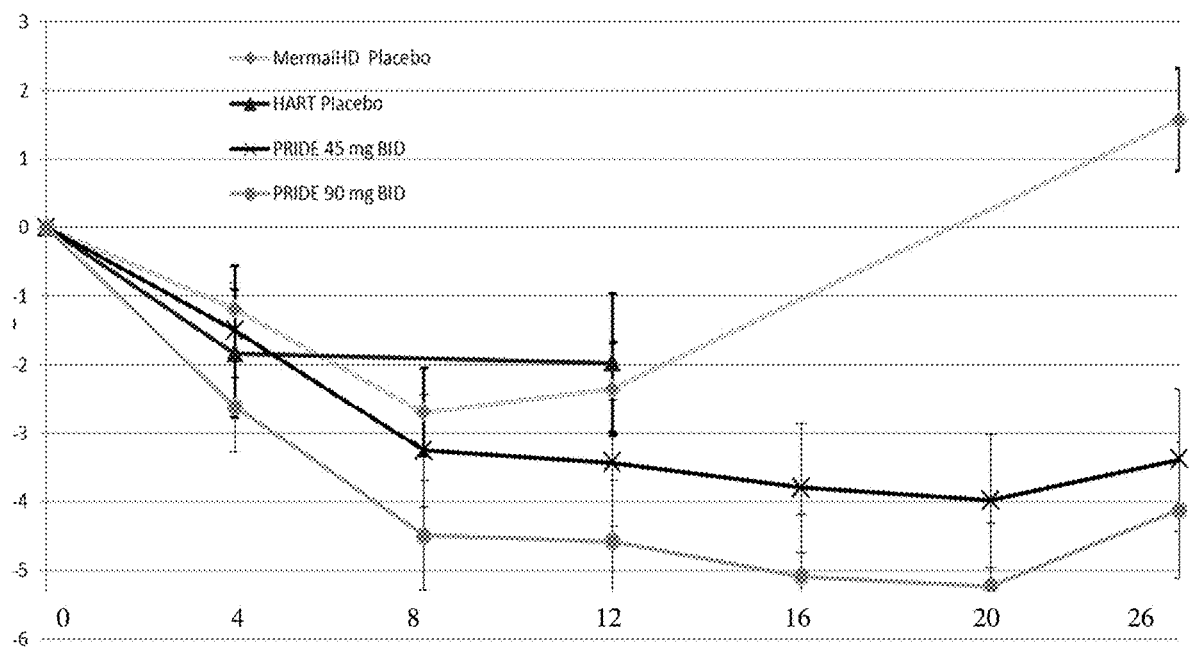
Figure 5B:
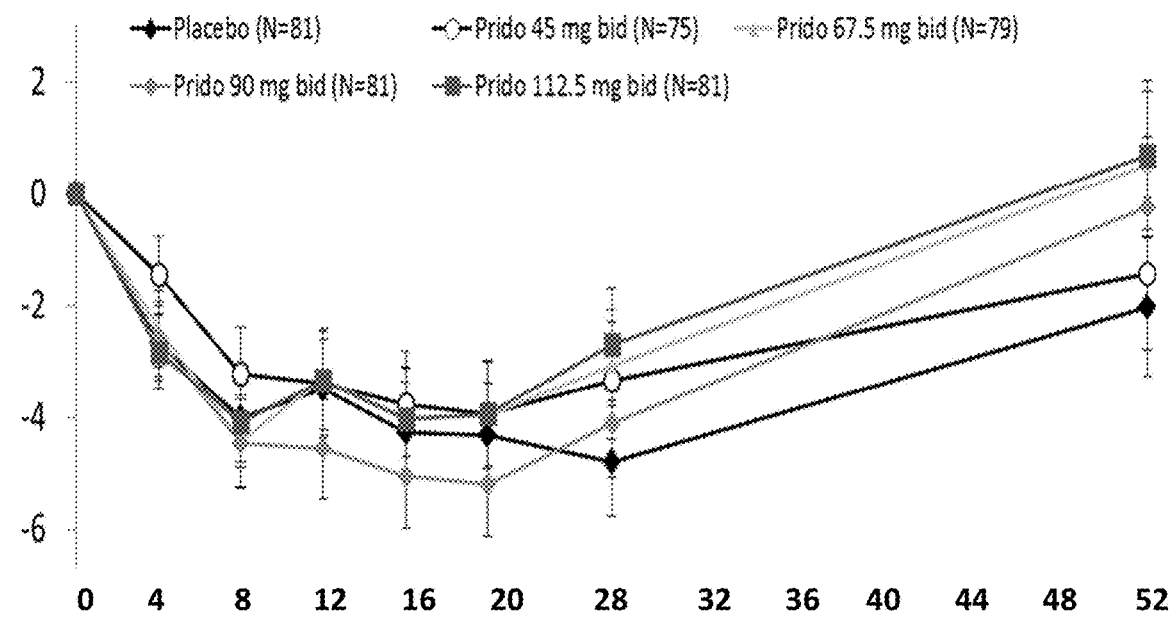

FIGS. 5a and 5b: Change from baseline in TMS. FIG. 5a: Using historical placebo in HART and MermaiHD clinical trials, TMS (change from baseline) results are significant for both 45 mg pridopidine bid and 90 mg pridopidine bid. A lower number indicates improvement. FIG. 5b: Change from baseline UHDRS-TMS full analysis set plotted over time. PRIDE-HD replicates previous data in TMS changes from baseline as the change from baseline values were similar to those in HART and MermaiHD. In this graph, a decrease in TMS change from baseline indicates improvement. Dark line with diamonds represents placebo, dark line with open circles represents 45 mg bid, gray line with triangles represents 67.5 mg bid, gray line with diamonds represents 90 mg bid, line with squares represents 112.5 mg bid. The 90 mg bid dose demonstrated the largest treatment effect.

Figure 6A:
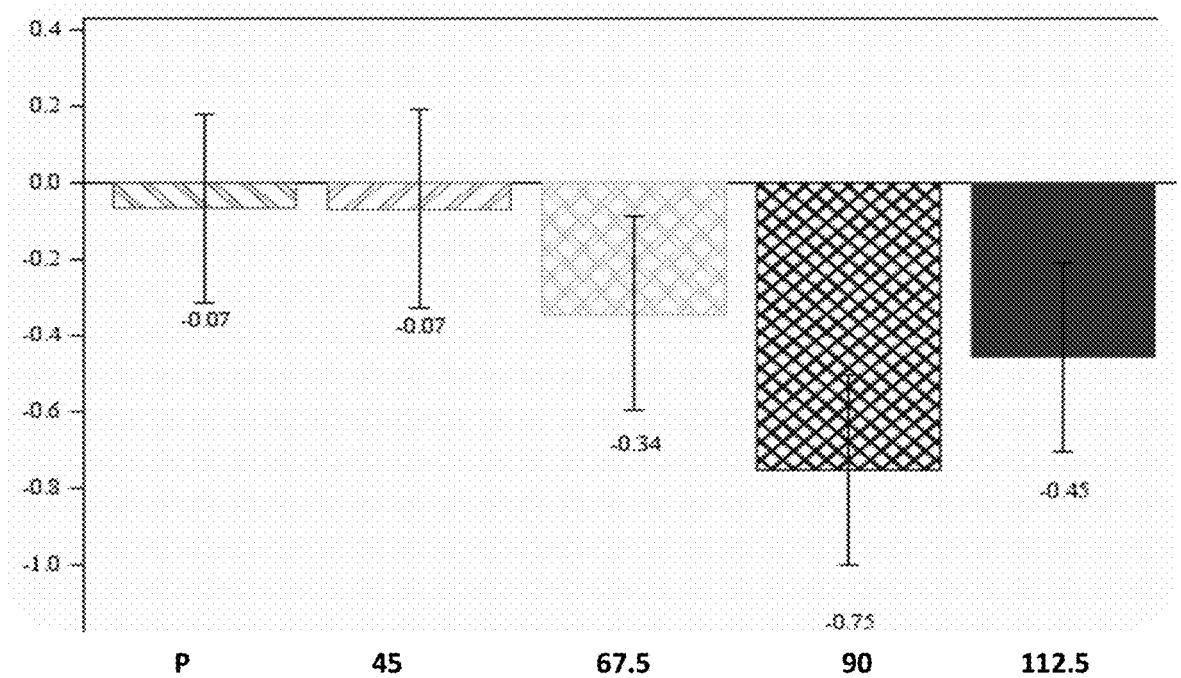
Figure 6B:
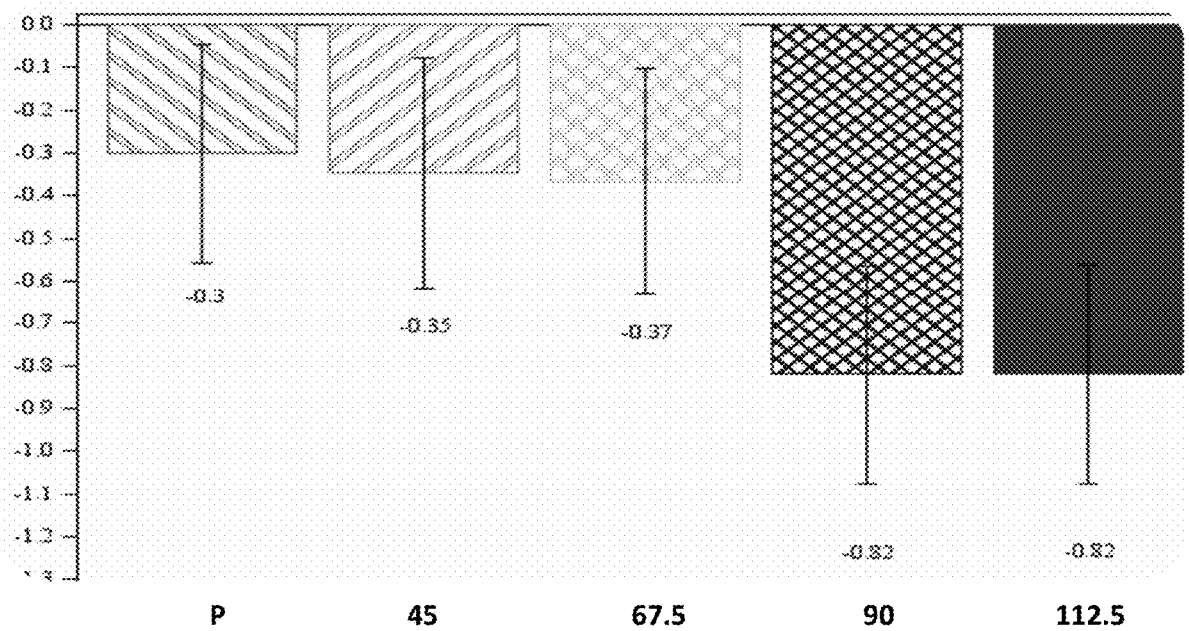
Figure 6C:
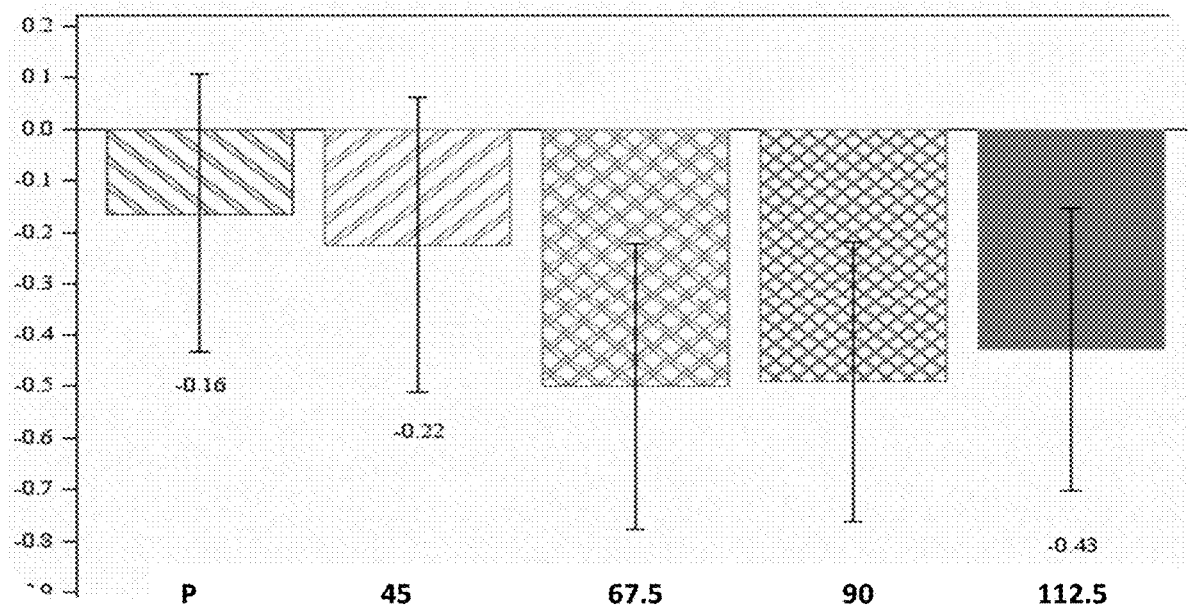

FIGS. 6a, 6b and 6c: Total Dystonia at week 12 (6a); at week 20 (6b); and at week 26 (6c) in patient groups administered different doses of pridopidine. Y-axis is change in dystonia from baseline. All data refer to adjusted means+ SE of change in dystonia in full analysis set. A lower number indicates improvement.

Figure 7A:
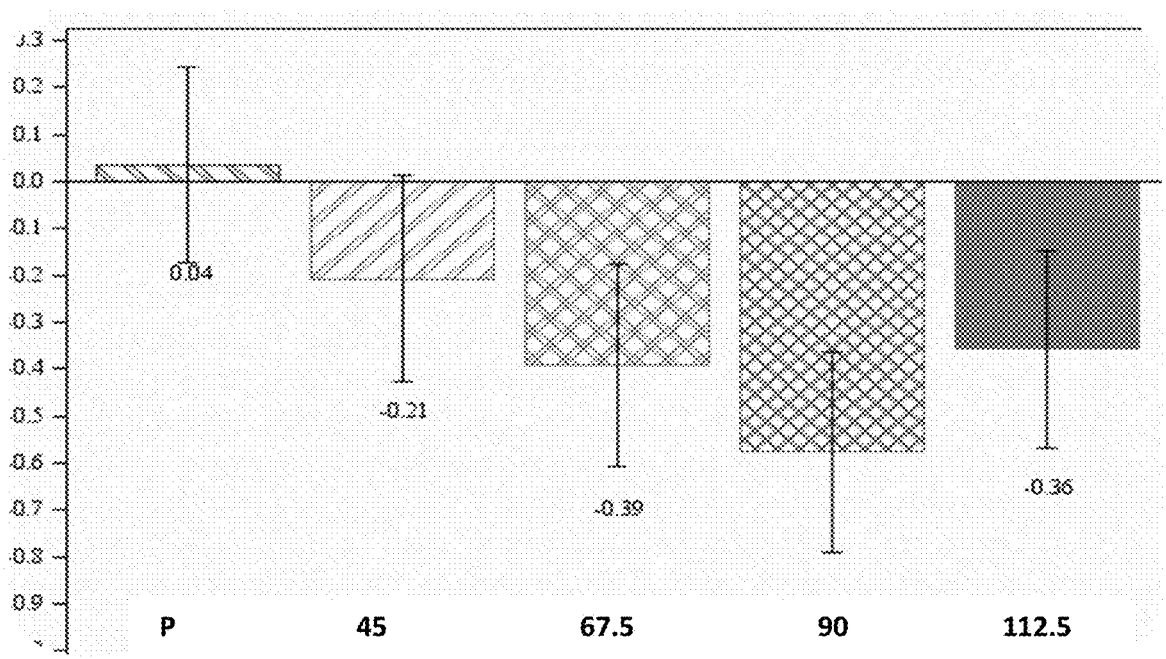
Figure 7B:
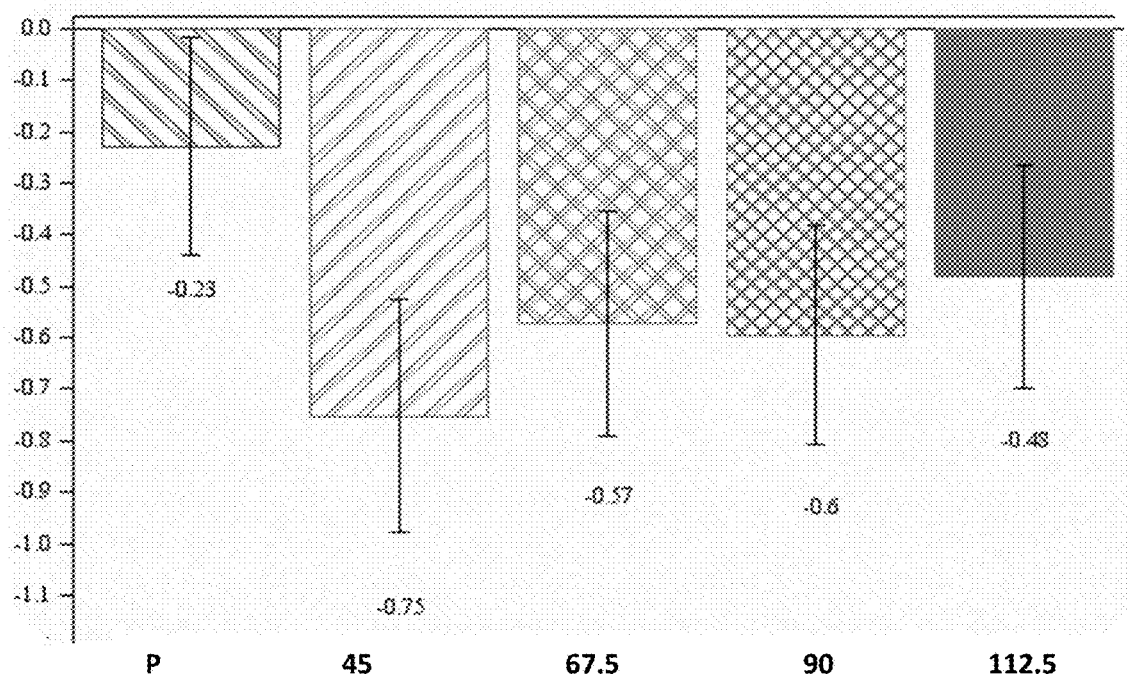

FIG. 7a: Change in Dystonia in limbs (UHDRS-dystonia limbs) at week 12; FIG. 7b: Finger Taps and Pronate-Supinate (P/S) hands at week 20; FIG. 7c: Finger Taps and P/S hands at week 26. Finger Taps and Pronate-Supinate (P/S) hands is a combination of finger tapping (the ability to tap the fingers of both hands where 15 repetitions in 5 seconds is considered normal) with pronation/supination (the ability to rotate the forearm and hand such that the palm is down (pronation) and to rotate the forearm and hand such that the palm is up (supination) on both sides of the body).

In the tables below, data and the P-Values corresponding to the figures are provided. N refers to number of patients. Wk26 refers to relevant score at week 26. Wk52 refers to relevant score at week 52. "Δ to placebo" refers to the difference in score from compared to placebo, specifically, the average change from baseline in the placebo group compared to the average change from baseline of the relevant group. "ALL" refers to pridopidine treated patients irrespective of disease stage. Y-axes are change from baseline for characteristic listed above the table. X-axes are dose whereby P means "placebo", 45 means "45 mg bid," 67.5 means "67.5 mg bid," 90 means "90 mg bid," and 112.5 means "112.5 mg bid." In the figures, improvement is in the direction from bottom of the graph to top of the graph.

Figure 8A:
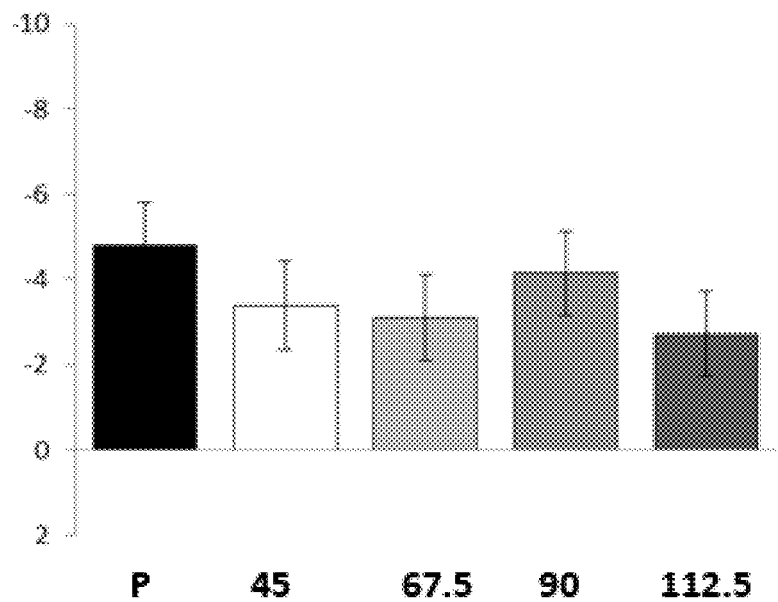
Figure 8B:
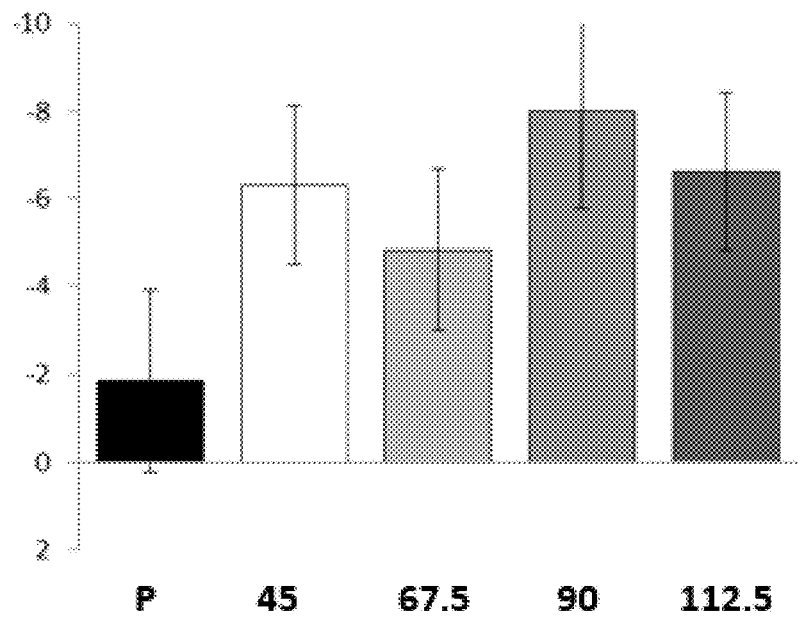

For example, FIG. 8b shows the average difference in the UHDRS TMS score of the indicated group of patients (i.e. patients having a TFC score of 11-13 at baseline) between the score at baseline (prior to administration of pridopidine at week 0) and the score after 26 weeks of administration of pridopidine (at week 26). In this figure, the 90 mg bid dose shows the greatest improvement because its data point is the top most data point in the figure, showing an approximately 8 point improvement compared to baseline (i.e. a −8 UHDRS TMS score at week 26 compared to baseline). The table below the description of FIG. 8b shows that the 90 mg bid group had 11 patients ("N" row) and an average UHDRS TMS score of 39.1 at baseline ("Baseline" row). The table below the description of FIG. 8b also shows that the 90 mg bid group's change from baseline (about −8, shown in figure, not shown in table) is 6.15 points better (−6.15) than the placebo group's change from placebo (about −2, shown in figure, not shown in table)("Δ to placebo" row). Additionally, the table below the description of FIG. 8b shows a p value of 0.0361 for the 90 mg bid group ("p value" row). HD1 refers to an early stage Huntington's disease (HD) patient with a baseline Unified Huntington's Disease Rating Scale Total Functional Capacity (UHDRS-TFC; TFC) score of 11-13. HD2 refers to an early stage HD patient with a baseline UHDRS-TFC score of 7-10.

FIG. 8a: Change from baseline in UHDRS TMS Week 26 ALL. The table below and FIG. 8a show no significant improvement in UHDRS TMS in all pridopidine treated patients at 26 weeks compared to placebo. Improvement is evidenced by a more negative value in the UHDRS TMS score.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 46.9 | 44.5 | 46.9 | 47 | 46.7 |
| Δ to placebo |  | 1.42 | 1.71 | 0.67 | 2.1 |
| p value |  | 0.3199 | 0.2235 | 0.6282 | 0.1337 |

FIG. 8b: Change from baseline in UHDRS TMS Week 26 Stage 1 BL TFC 11-13. (The UHDRS TMS score at week 26 of pridopidine treated patients with a baseline Total Functional Capacity (BL TFC) score of 11 to 13). HD patients with a baseline TFC score of 11-13 are generally considered to be first stage (stage 1) HD patients. The table below and FIG. 8b show trend towards improvement in UHDRS TMS in HD1 pridopidine treated patients at 26 weeks compared to placebo.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 37.3 | 35.4 | 36.4 | 39.1 | 38.7 |
| Δ to placebo |  | −4.47 | −3 | −6.15 | −4.79 |
| p value |  | 0.0976 | 0.2505 | 0.0361 | 0.0676 |

Figure 8C:
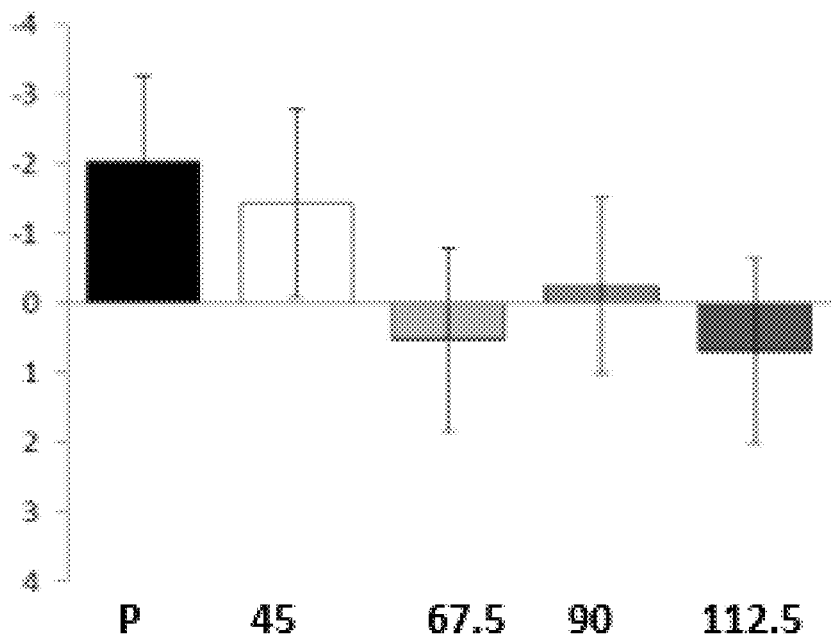

FIG. 8c: Change from baseline in UHDRS TMS Week 52 ALL. The table below and FIG. 8c show no significant improvement in UHDRS TMS in all pridopidine treated patients at 52 weeks, compared to placebo.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 46.9 | 44.5 | 46.9 | 47 | 46.7 |
| Δ to placebo |  | 0.59 | 2.55 | 1.78 | 2.71 |
| p value |  | 0.7468 | 0.1591 | 0.3144 | 0.137 |

Figure 8D:
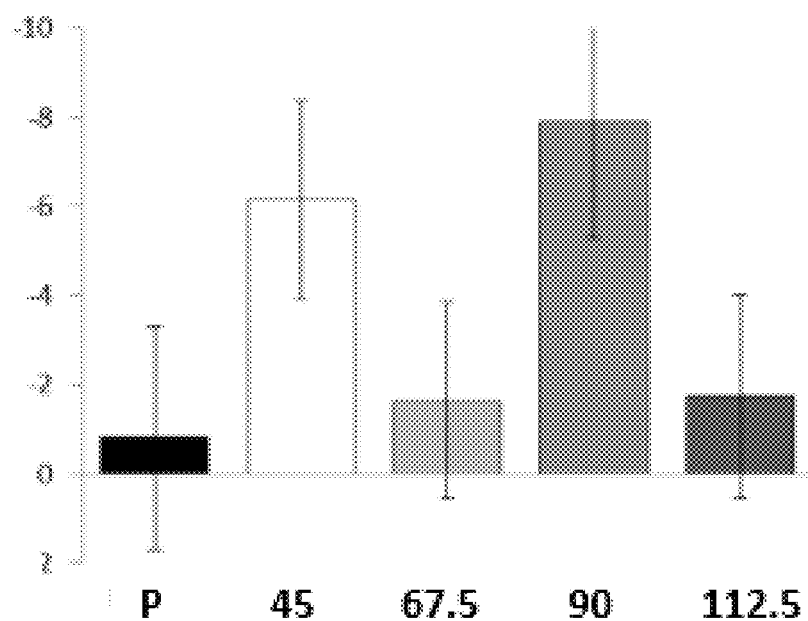

FIG. 8d: Change from baseline in UHDRS TMS Week 52 Stage 1 BL TFC 11-13. The table below and FIG. 8d show a trend towards improvement in UHDRS TMS in HD1 pridopidine treated patients at 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 37.3 | 35.4 | 36.4 | 39.1 | 38.7 |
| Wk 52 Δ to placebo |  | −5.32 | −0.84 | −7.1 | −0.92 |
| p value |  | 0.1065 | 0.7918 | 0.047 | 0.7765 |

Figure 8E:
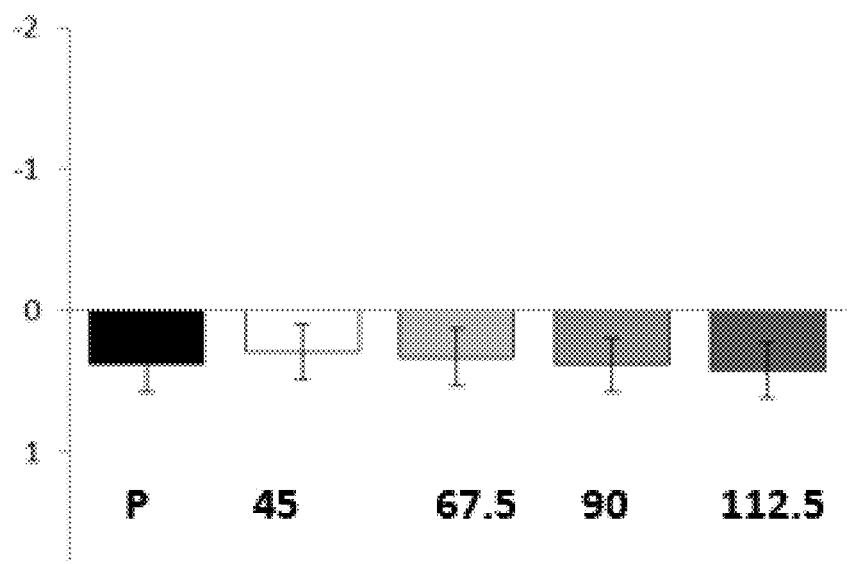

FIG. 8e: Change from baseline in UHDRS TMS Gait and Balances Week 52. The table below and FIG. 8e show no significant improvement in UHDRS TMS gait and balances in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.8 | 4.1 | 4.1 | 4 | 3.8 |
| Δ to placebo |  | −0.09 | −0.05 | −0.01 | 0.04 |
| p value |  | 0.7404 | 0.8532 | 0.9747 | 0.8923 |

Figure 8F:
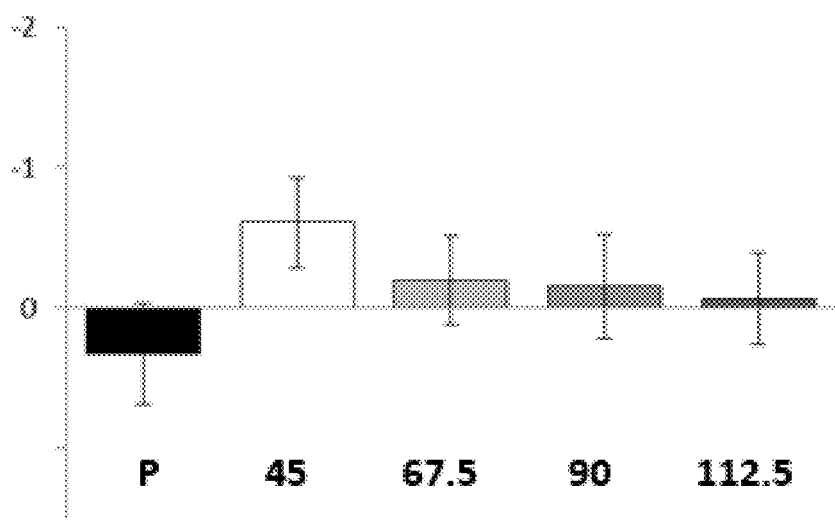

FIG. 8f: Change from baseline in UHDRS TMS Gait and Balances Week 52 Stage 1 BL TFC 11-13. The table below and FIG. 8f show a trend towards improvement in UHDRS TMS gait and balances in HD1 pridopidine treated patients at 52 weeks with significance for patients receiving 45 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.3 | 2.8 | 2.6 | 2.6 | 2.4 |
| Δ to placebo |  | −0.94 | −0.53 | −0.49 | −0.4 |
| p value |  | 0.0445 | 0.2294 | 0.3056 | 0.3797 |

Figure 8G:
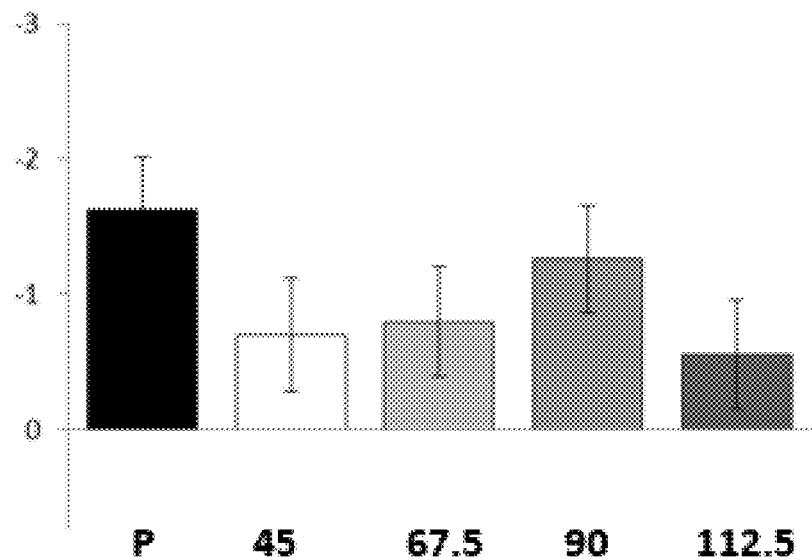

FIG. 8g: Change from baseline in UHDRS TMS Chorea Week 26 ALL. The table below and FIG. 8g show no significant improvement in UHDRS TMS chorea in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 11.4 | 10.9 | 11 | 11.2 | 10.9 |
| Δ to placebo |  | 0.92 | 0.81 | 0.36 | 1.05 |
| p value |  | 0.1083 | 0.1501 | 0.5185 | 0.0609 |

Figure 8H:
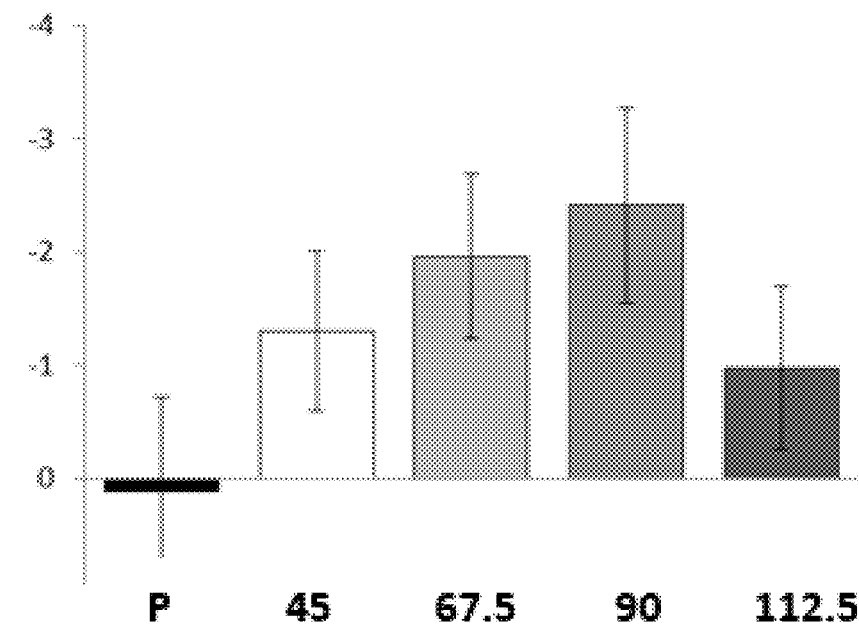

FIG. 8h: Change from baseline in UHDRS TMS Chorea Week 26 Stage 1 BL TFC 11-13. The table below and FIG. 8h show a trend towards improvement in UHDRS TMS chorea in HD1 pridopidine treated patients at 26 weeks with significance for patients receiving 90 mg bid pridopidine.

|  | 45 mg bid | 67.5 mg bid | 90 mg bid | 112.5 mg bid |
|---|---|---|---|---|
| N | 17 | 17 | 11 | 18 |
| Wk 26 Δ to placebo | −1.4 | −2.07 | −2.52 | −1.08 |
| p value | 0.1805 | 0.0438 | 0.0271 | 0.2932 |

Figure 8I:
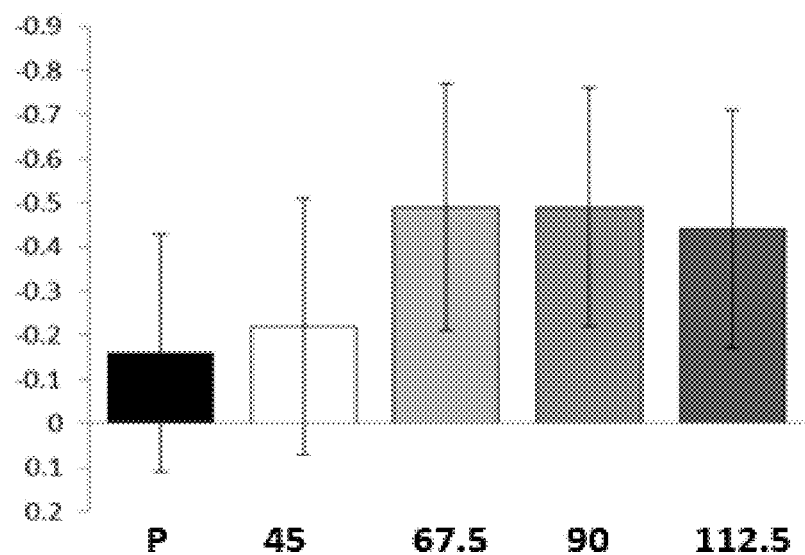

FIG. 8i: Change from baseline in UHDRS TMS Dystonia Week 26 ALL. The table below and FIG. 8i show a trend towards improvement in UHDRS TMS dystonia in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4.1 | 3.6 | 4.1 | 4.9 | 4.5 |
| Δ to placebo |  | −0.06 | −0.34 | −0.33 | −0.29 |
| p value |  | 0.8711 | 0.3778 | 0.3845 | 0.4507 |

Figure 8J:
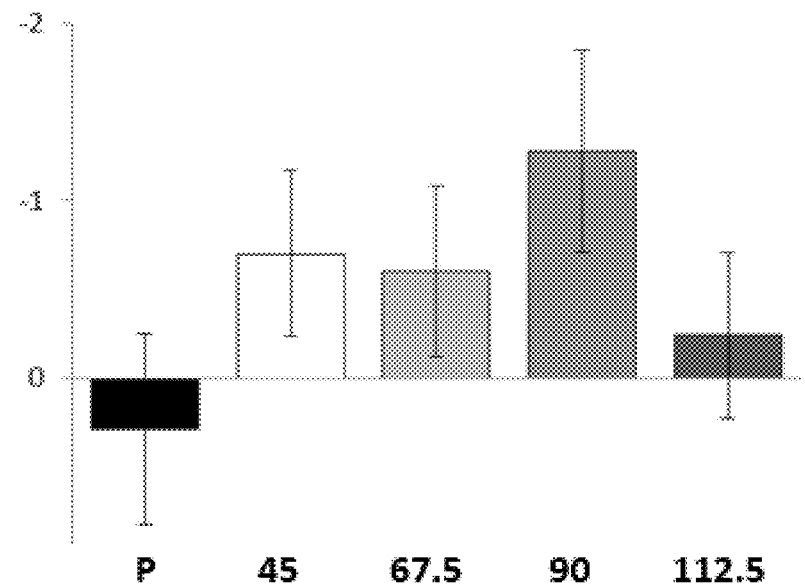

FIG. 8j: Change from baseline in UHDRS TMS Dystonia Week 26 Stage 1 BL TFC 11-13. The table below and FIG. 8j show a trend towards improvement in UHDRS TMS dystonia in HD1 pridopidine treated patients at 26 weeks with significance for patients receiving 90 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.8 | 2.1 | 2.2 | 3.2 | 2.4 |
| Δ to placebo |  | −0.99 | −0.89 | −1.56 | −0.53 |
| p value |  | 0.1569 | 0.1882 | 0.0396 | 0.4303 |

Figure 8K:
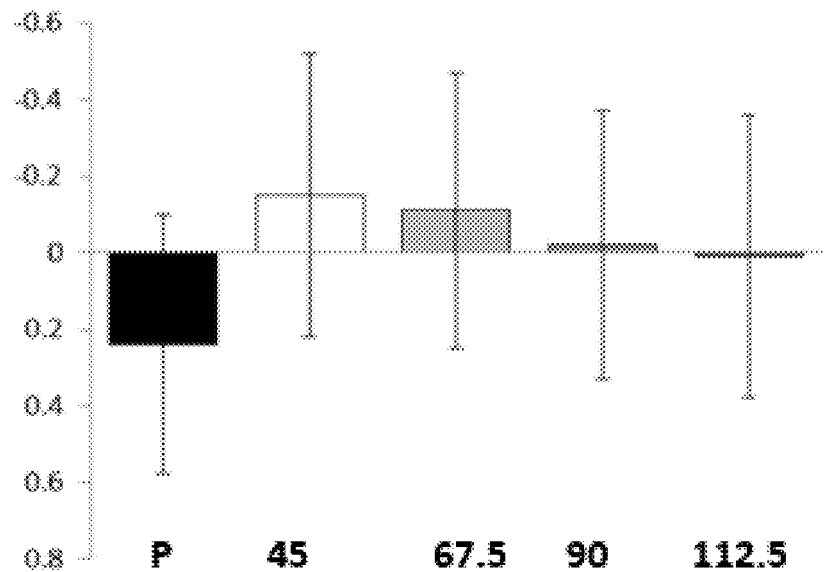

FIG. 8k: Change from baseline in UHDRS TMS Dystonia Week 52. The table below and FIG. 8k show a trend toward improvement in UHDRS TMS dystonia in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4.1 | 3.6 | 4.1 | 4.9 | 4.5 |
| Δ to placebo |  | −0.39 | −0.35 | −0.27 | −0.24 |
| p value |  | 0.4358 | 0.4795 | 0.5858 | 0.6382 |

Figure 8L:
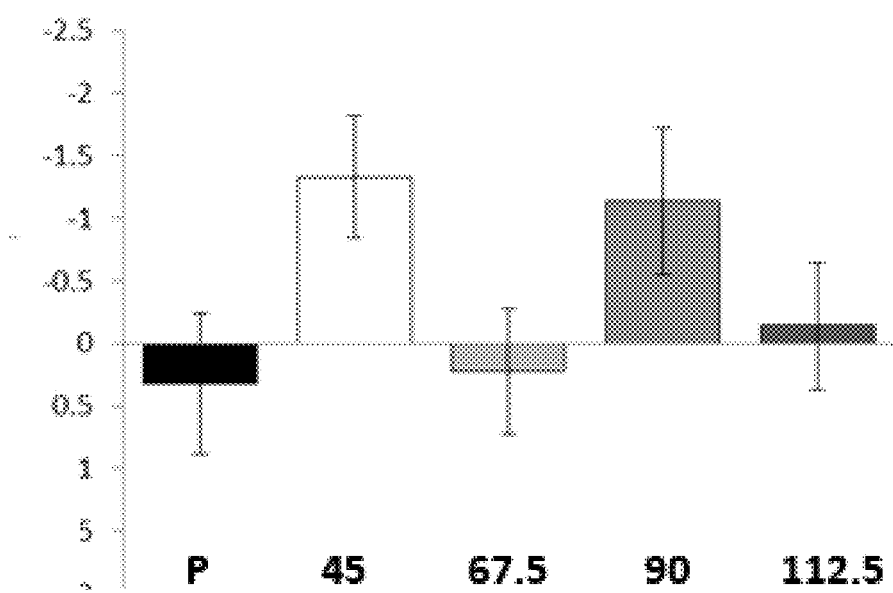

FIG. 8l: Change from baseline in UHDRS TMS Dystonia Week 52 Stage 1 BL TFC 11-13. The table below and FIG. 8l show a trend towards improvement in UHDRS TMS dystonia in HD1 pridopidine treated patients at 52 weeks with significance for patients receiving 45 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.8 | 2.1 | 2.2 | 3.2 | 2.4 |
| Δ to placebo |  | −1.65 | −0.1 | −1.46 | −0.46 |
| p value |  | 0.0243 | 0.8848 | 0.0575 | 0.5228 |

Figure 8M:
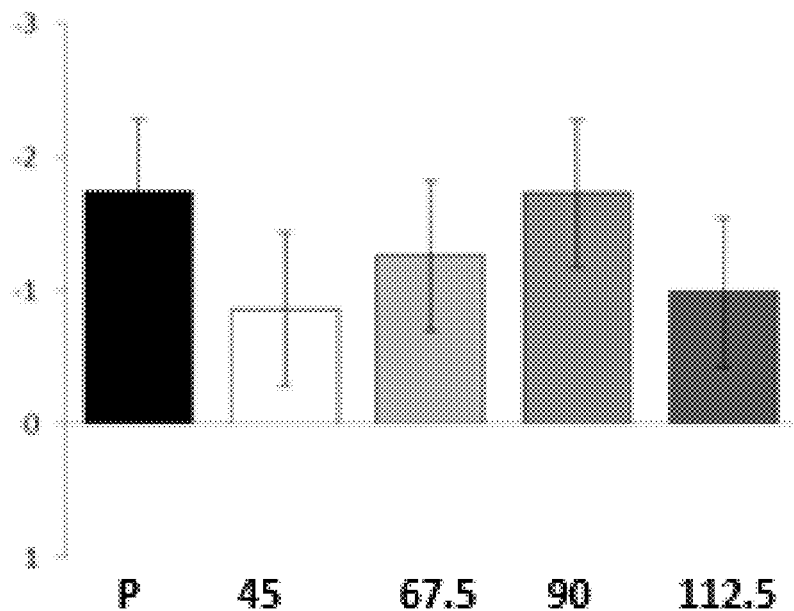

FIG. 8m: Change from baseline in UHDRS TMS Involuntary Movements Week 26 ALL The table below and FIG. 8m show no significant improvement in UHDRS TMS Involuntary Movements in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 15.6 | 14.4 | 15.1 | 16 | 15.4 |
| Δ to placebo |  | 0.89 | 0.48 | 0.01 | 0.76 |
| p value |  | 0.2594 | 0.5328 | 0.9873 | 0.3268 |

Figure 8N:
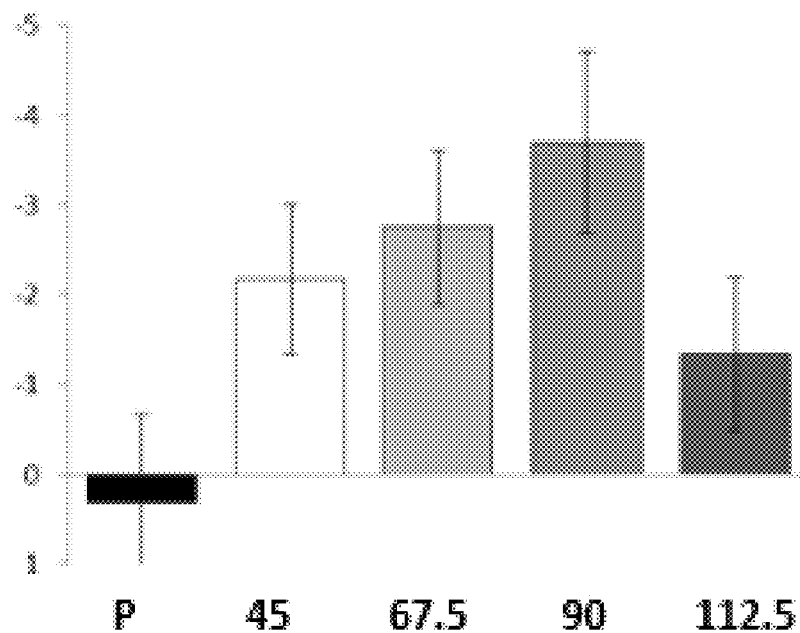

FIG. 8n: Change from baseline in UHDRS TMS Involuntary Movements Week 26 Stage 1 BL TFC 11-13. The table below and FIG. 8n show significant improvement in UHDRS TMS Involuntary Movements at 26 weeks in HD1 pridopidine treated patients receiving 45 mg bid, 67.5 bid and 90 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 11.5 | 12 | 12.2 | 12.9 | 13.2 |
| Δ to placebo |  | −2.49 | −3.07 | −4 | −1.64 |
| p value |  | 0.0469 | 0.0117 | 0.0033 | 0.1731 |

Figure 8O:
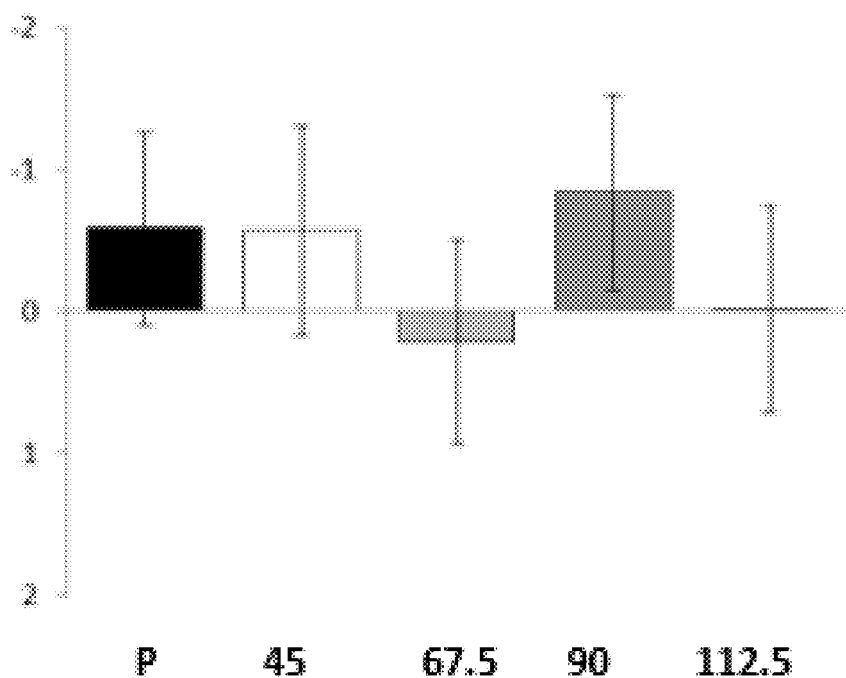

FIG. 8o: Change from baseline in UHDRS TMS Involuntary Movements Week 52 The table below and FIG. 8o show no significant improvement in UHDRS TMS Involuntary Movements in all pridopidine treated patients at 52 weeks.

|           | Placebo | 45 mg bid | 67.5 mg bid | 90 mg bid | 112.5 mg bid |
|-----------|---------|-----------|-------------|-----------|--------------|
| N         | 81      | 75        | 79          | 81        | 81           |
| Baseline  | 15.6    | 14.4      | 15.1        | 16        | 15.4         |
| Δ to placebo |      | 0.02      | 0.8         | −0.26     | 0.57         |
| p value   |         | 0.9867    | 0.4196      | 0.7893    | 0.5648       |

Figure 8P:
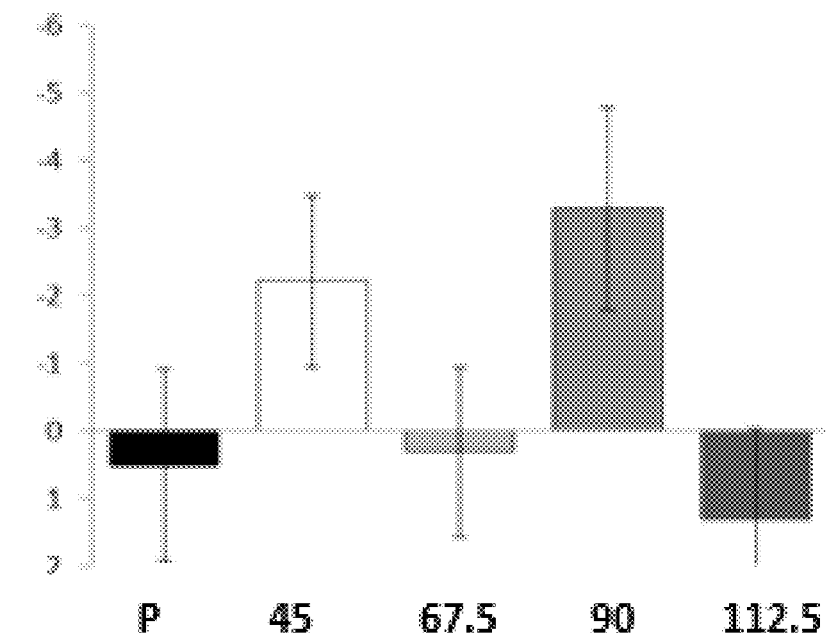

FIG. 8p: Change from baseline in UHDRS TMS Involuntary Movements Week 52 Stage 1 BL TFC 11-13. The table below and FIG. 8p show a trend towards improvement in UHDRS TMS Involuntary Movements in HD1 pridopidine treated patients at 52 weeks, in particular in 45 mg bid and 90 mg bid treated patients.

|           | Placebo | 45 mg bid | 67.5 mg bid | 90 mg bid | 112.5 mg bid |
|-----------|---------|-----------|-------------|-----------|--------------|
| N         | 12      | 17        | 17          | 11        | 18           |
| Baseline  | 11.5    | 12        | 12.2        | 12.9      | 13.2         |
| Δ to placebo |      | −2.73     | −0.2        | −3.8      | 0.8          |
| p value   |         | 0.1487    | 0.9111      | 0.0643    | 0.6751       |

Figure 8Q:
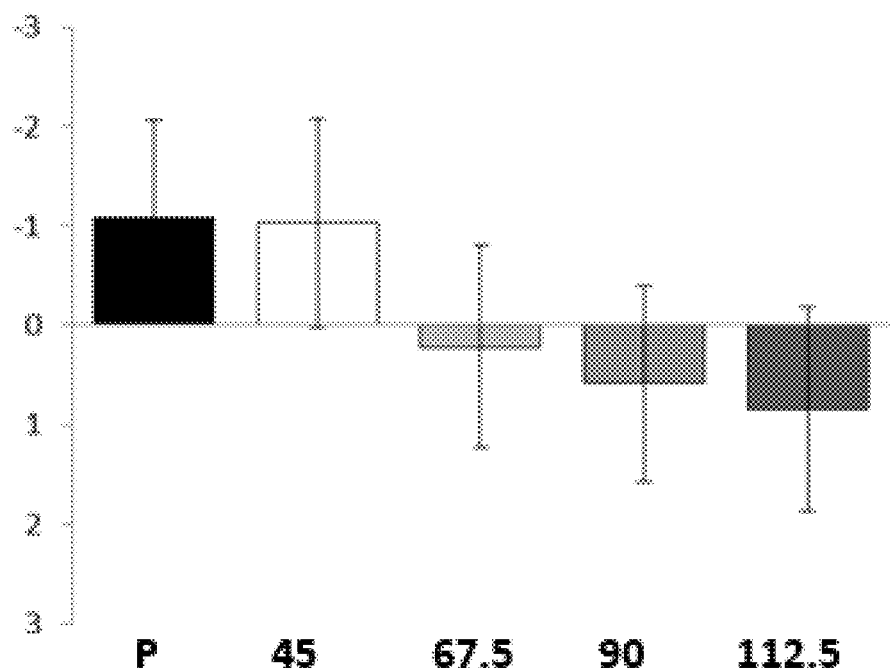

FIG. 8q: Change from baseline in UHDRS TMS Excluding Chorea Week 52. The table below and FIG. 8q show no significant improvement in UHDRS TMS excluding chorea in all pridopidine treated patients at 52 weeks.

|           | Placebo | 45 mg bid | 67.5 mg bid | 90 mg bid | 112.5 mg bid |
|-----------|---------|-----------|-------------|-----------|--------------|
| N         | 81      | 75        | 79          | 81        | 81           |
| Baseline  | 35.5    | 33.6      | 35.9        | 35.8      | 35.8         |
| Δ to placebo |      | 0.05      | 1.31        | 1.67      | 1.94         |
| p value   |         | 0.9693    | 0.3495      | 0.2234    | 0.1704       |

Figure 8R:
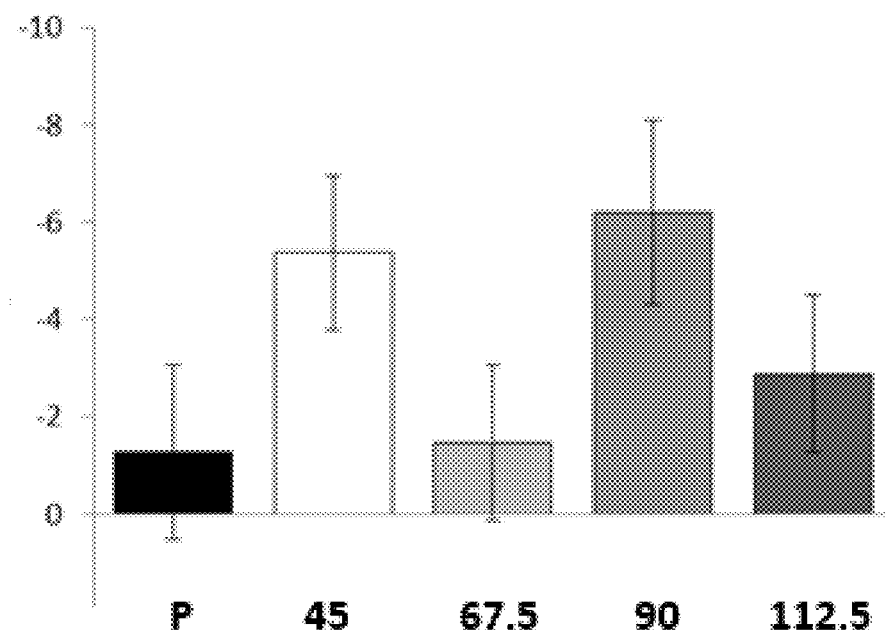

FIG. 8r: Change from baseline in UHDRS TMS Excluding Chorea Week 52 Stage 1 BL TFC 11-13. The table below and FIG. 8r show a trend towards improvement in UHDRS TMS excluding chorea in HD1 pridopidine treated patients at 52 weeks, in particular in the 45 mg bid and 90 mg bid treated patients.

|           | Placebo | 45 mg bid | 67.5 mg bid | 90 mg bid | 112.5 mg bid |
|-----------|---------|-----------|-------------|-----------|--------------|
| N         | 12      | 17        | 17          | 11        | 18           |
| Baseline  | 28.6    | 25.5      | 26.4        | 29.4      | 27.8         |
| Δ to placebo |      | −4.09     | −0.18       | −4.92     | −1.59        |
| p value   |         | 0.083     | 0.9358      | 0.0505    | 0.4924       |

Figure 8S:
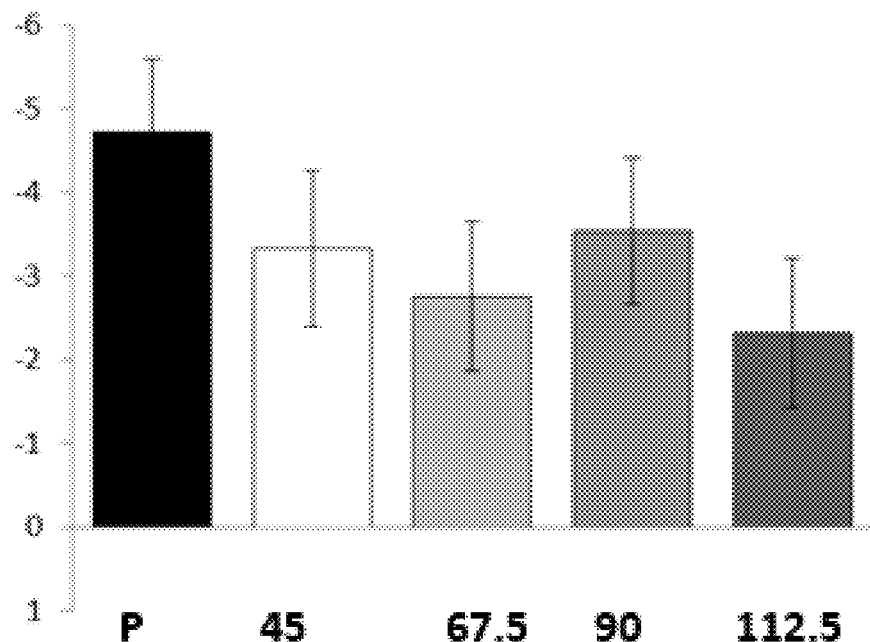

FIG. 8s: Change from baseline in UHDRS TMS Excluding Dystonia Week 26 ALL. The table below and FIG. 8s show no significant improvement in UHDRS TMS excluding dystonia in all pridopidine treated patients at 26 weeks.

|           | Placebo | 45 mg bid | 67.5 mg bid | 90 mg bid | 112.5 mg bid |
|-----------|---------|-----------|-------------|-----------|--------------|
| N         | 81      | 75        | 79          | 81        | 81           |
| Baseline  | 42.7    | 40.9      | 42.8        | 42.1      | 42.2         |
| Δ to placebo |      | 1.39      | 1.97        | 1.2       | 2.4          |
| p value   |         | 0.2733    | 0.1137      | 0.3314    | 0.0539       |

Figure 8T:
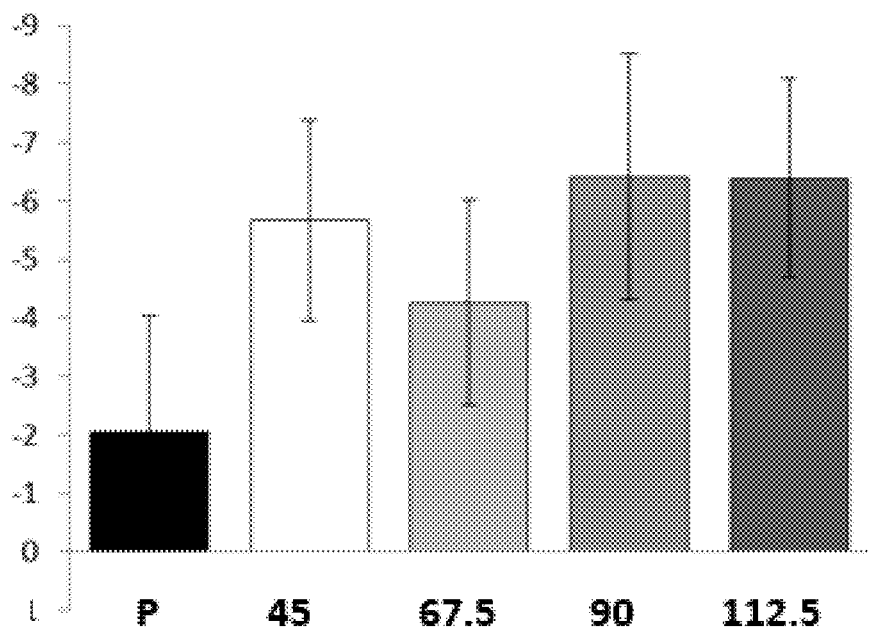

FIG. 8t: Change from baseline in UHDRS TMS Excluding Dystonia Week 26 Stage 1 BL TFC 11-13. The table below and FIG. 8t show a trend towards improvement in UHDRS TMS excluding dystonia in HD1 pridopidine treated patients, at 26 weeks.

|           | Placebo | 45 mg bid | 67.5 mg bid | 90 mg bid | 112.5 mg bid |
|-----------|---------|-----------|-------------|-----------|--------------|
| N         | 12      | 17        | 17          | 11        | 18           |
| Baseline  | 34.6    | 33.4      | 34.1        | 35.9      | 36.3         |
| Δ to placebo |      | −3.6      | −2.2        | −4.35     | −4.31        |
| p value   |         | 0.1594    | 0.376       | 0.1167    | 0.0842       |

FIGS. 9a-9e show bar graphs of changes in UHDRS TMS Finger Tap scores in 26 and 52 week patient groups.

Figure 9A:
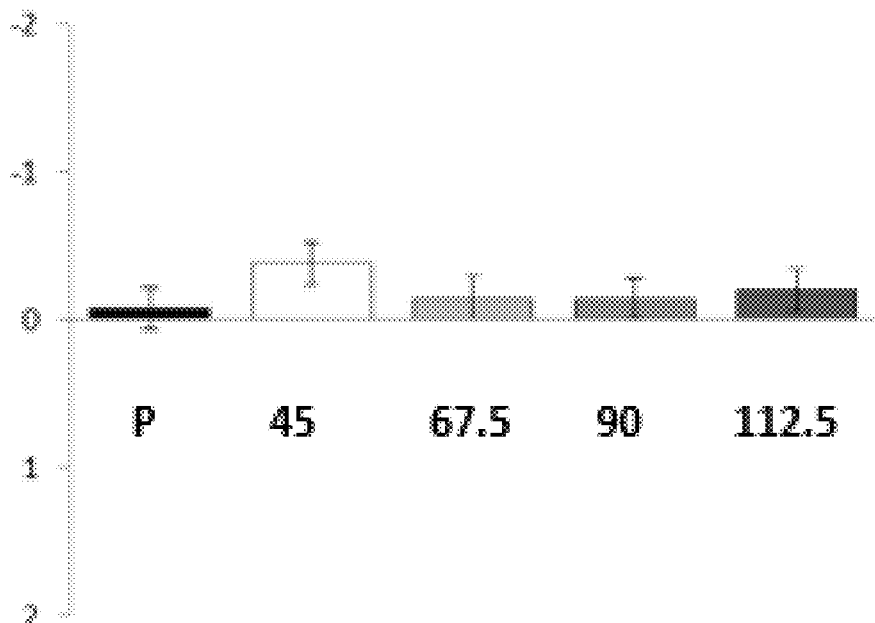

FIG. 9a: Change from Baseline in UHDRS TMS Finger Taps ALL. Week 26. The table below provides P-Values corresponding to FIG. 9a. The table below and FIG. 9a show no significant improvement in the UHDRS TMS finger taps in all pridopidine treated patients, at 26 weeks.

|           | Placebo | 45 mg bid | 67.5 mg bid | 90 mg bid | 112.5 mg bid |
|-----------|---------|-----------|-------------|-----------|--------------|
| N         | 81      | 75        | 79          | 81        | 81           |
| Baseline  | 3.8     | 3.5       | 4.1         | 3.7       | 3.9          |
| Δ to placebo |      | −0.3      | −0.07       | −0.07     | −0.12        |
| p value   |         | 0.1466    | 0.7306      | 0.7114    | 0.5475       |

Figure 9B:
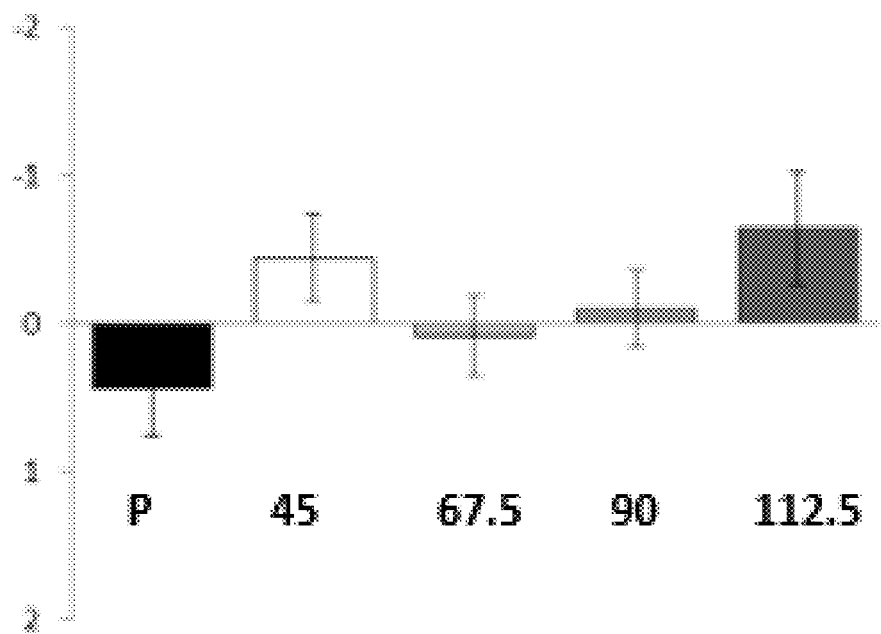

FIG. 9b: Change from Baseline in UHDRS TMS Finger Taps: Week 26 patients with baseline total functional capacity (BL TFC)≥9 and CAG Repeats>44. The table below provides the P-Values corresponding to FIG. 9b. The table below and FIG. 9b show statistically significant improvement in the UHDRS TMS finger taps in 45 mg bid and 112.5 mg bid pridopidine treated patients having BL TFC greater than or equal to 9 and greater than 44 CAG repeats in their htt gene, at 26 weeks.

|           | Placebo | 45 mg bid | 67.5 mg bid | 90 mg bid | 112.5 mg bid |
|-----------|---------|-----------|-------------|-----------|--------------|
| N         | 13      | 15        | 19          | 22        | 11           |
| Baseline  | 2.6     | 2.7       | 3.3         | 3         | 3.6          |
| Δ to placebo |      | −0.86     | −0.34       | −0.52     | −1.07        |
| p value   |         | 0.0499    | 0.4255      | 0.1972    | 0.0424       |

Figure 9C:
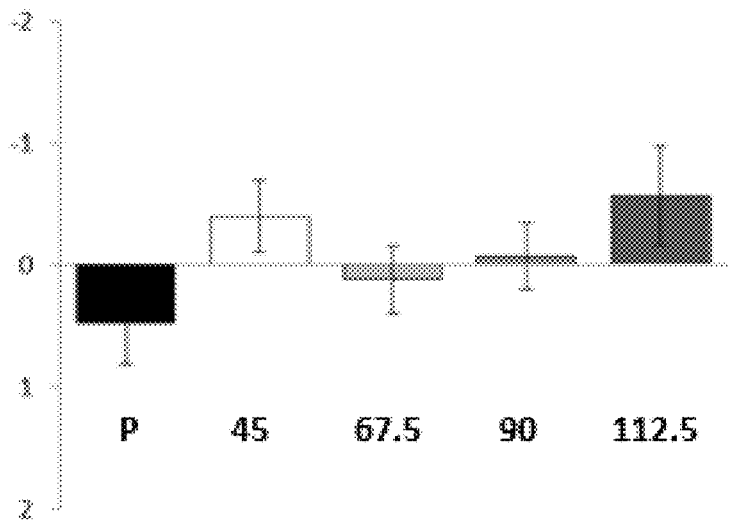

FIG. 9c: Change from baseline in UHDRS TMS Finger Taps: Week 26 patients with BL TFC≥9, CAG Repeats<44 and patients who represent three least severe TMS quarters (BL TMS 1st 3 Qs). The table below provides the P-Values corresponding to FIG. 9c. The table below and FIG. 9c show statistically significant improvement in the UHDRS TMS finger taps in 45 mg bid and 112.5 mg bid pridopidine treated patients having BL TFC greater than or equal to 9 and less than 44 CAG repeats in their htt gene, at 26 weeks.

|  | Placebo | 45 mg bid | 67.5 mg bid | 90 mg bid | 112.5 mg bid |
| --- | --- | --- | --- | --- | --- |
| N | 13 | 15 | 19 | 21 | 10 |
| Baseline | 2.6 | 2.7 | 3.3 | 3 | 3.5 |
| Δ to placebo |  | −0.87 | −0.36 | −0.54 | −1.05 |
| p value |  | 0.05 | 0.41 | 0.1888 | 0.0537 |

Figure 9D:
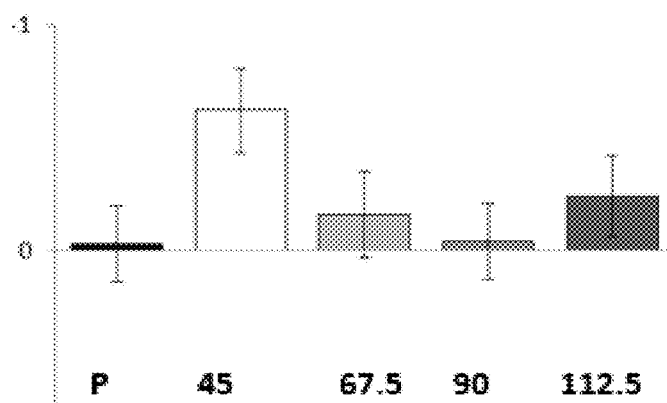

FIG. 9d: Change from baseline in UHDRS TMS Finger Taps: Patients who have completed 52 weeks of treatment: UHDRS TMS Finger Tap score at week 26. The table below provides the P-Values corresponding to FIG. 9d. The table below and FIG. 9d show statistically significant improvement in the UHDRS TMS finger taps in 45 mg bid pridopidine treated patients who completed 52 weeks, at 26 weeks.

|  | Placebo | 45 mg bid | 67.5 mg bid | 90 mg bid | 112.5 mg bid |
| --- | --- | --- | --- | --- | --- |
| N | 52 | 43 | 44 | 53 | 44 |
| Baseline | 3.8 | 3.2 | 4 | 3.5 | 3.8 |
| Δ to placebo |  | −0.59 | −0.13 | −0.01 | −0.21 |
| p value |  | 0.0182 | 0.5881 | 0.9554 | 0.3833 |

Figure 9E:
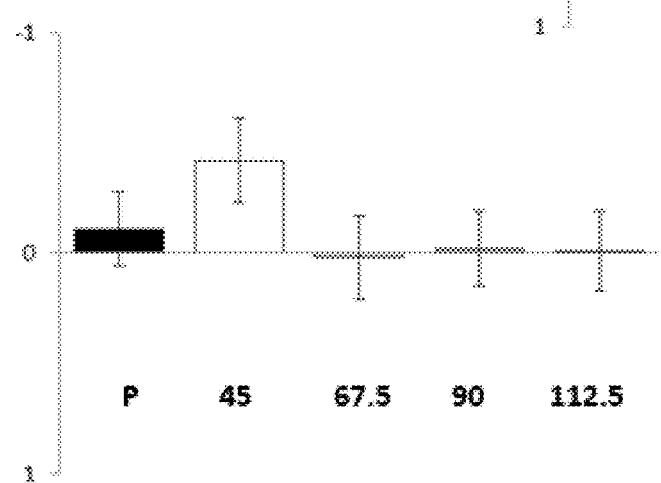

FIG. 9e: Change from baseline in UHDRS TMS Finger Taps: Patients who have completed 52 weeks of treatment: UHDRS TMS Finger Tap score at week 52. The table below provides the P-Values corresponding to FIG. 9e. The table below and FIG. 9e show no significant improvement in the UHDRS TMS finger taps in ALL pridopidine treated patients, at 52 weeks.

|  | Placebo | 45 mg bid | 67.5 mg bid | 90 mg bid | 112.5 mg bid |
| --- | --- | --- | --- | --- | --- |
| N | 52 | 43 | 44 | 53 | 44 |
| Baseline | 3.8 | 3.2 | 4 | 3.5 | 3.8 |
| Δ to placebo |  | −0.31 | 0.13 | 0.08 | 0.1 |
| p value |  | 0.2091 | 0.6027 | 0.7179 | 0.6835 |

Figure 9F:
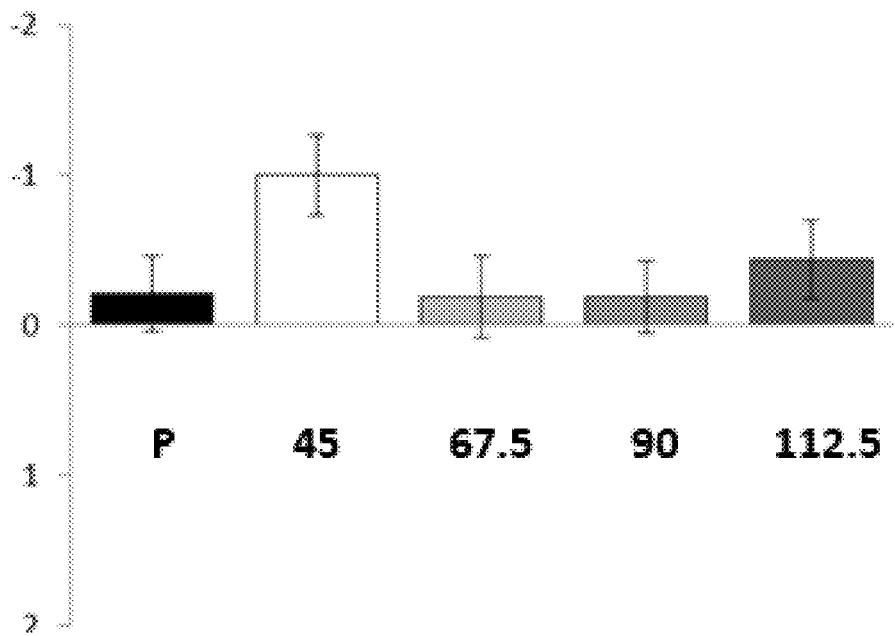

FIG. 9f: Change from baseline in UHDRS TMS Finger Tapping+Pronate-Supinate Hands: Patients who have completed 52 weeks of treatment—score at week 26. The table below provides the P-Values corresponding to FIG. 9f. The table below and FIG. 9f show statistically significant improvement in the UHDRS TMS finger taps and Pronate-Supinate Hands in 45 mg bid pridopidine treated patients who completed 52 weeks, at 26 weeks.

|  | Placebo | 45 mg bid | 67.5 mg bid | 90 mg bid | 112.5 mg bid |
| --- | --- | --- | --- | --- | --- |
| N | 52 | 43 | 44 | 53 | 44 |
| Baseline | 7.1 | 6.1 | 7 | 6.5 | 7 |
| Δ to placebo |  | −0.79 | 0.02 | 0.02 | −0.23 |
| p value |  | 0.0294 | 0.9443 | 0.9412 | 0.5268 |

Figure 9G:
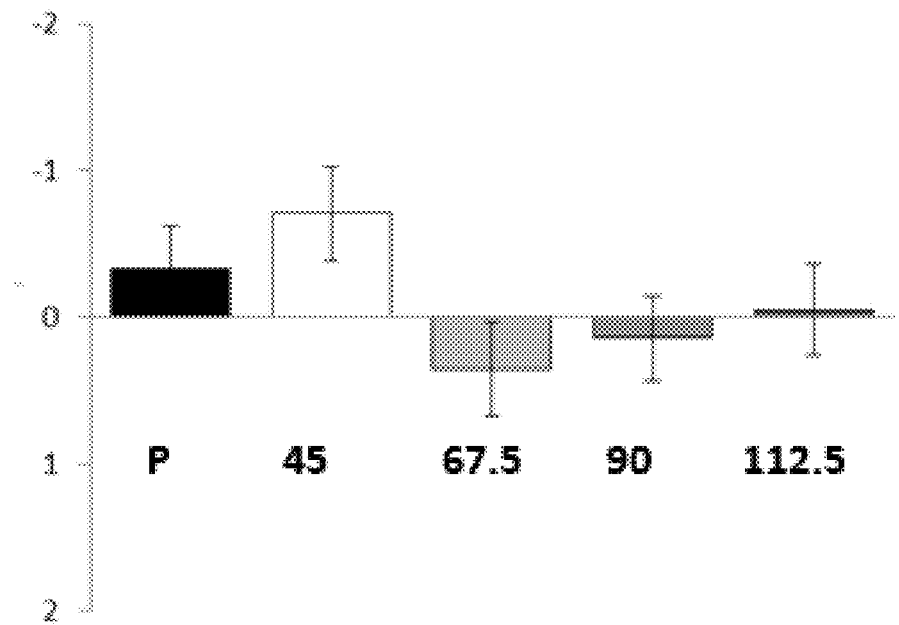

FIG. 9g: Change from baseline in UHDRS TMS Finger Tapping+Pronate-Supinate Hands: Patients who have completed 52 weeks of treatment—score at week 52. The table below provides the P-Values corresponding to FIG. 9g. The table below and FIG. 9g show no significant improvement in the UHDRS TMS finger taps and Pronate-Supinate Hands in pridopidine treated patients at 26 weeks.

|  | Placebo | 45 mg bid | 67.5 mg bid | 90 mg bid | 112.5 mg bid |
| --- | --- | --- | --- | --- | --- |
| N | 52 | 43 | 44 | 53 | 44 |
| Baseline | 7.1 | 6.1 | 7 | 6.5 | 7 |
| Δ to placebo |  | −0.37 | 0.68 | 0.48 | 0.28 |
| p value |  | 0.3801 | 0.1066 | 0.2337 | 0.4978 |

Figure 9H:
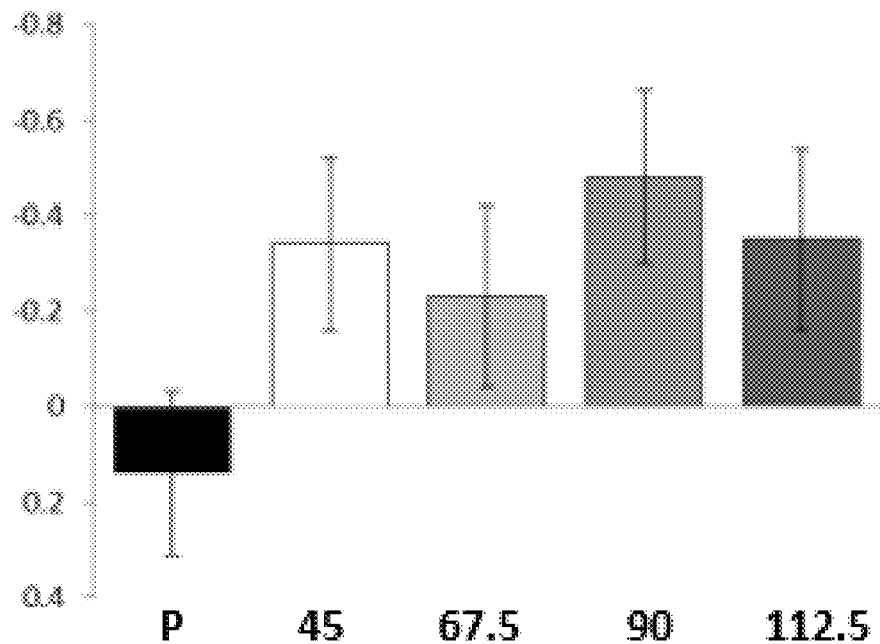

FIG. 9h: Change from baseline in UHDRS TMS Gait and Balance: Gait and balance scores at week 26 for patients with BL TFC≥7. The table below provides the P-Values corresponding to FIG. 9h. The table below and FIG. 9h show statistically significant improvement in the UHDRS TMS gait and balances in 90 mg bid pridopidine treated HD1 and HD2 patients at 26 weeks.

|  | Placebo | 45 mg bid | 67.5 mg bid | 90 mg bid | 112.5 mg bid |
| --- | --- | --- | --- | --- | --- |
| N | 62 | 59 | 54 | 56 | 58 |
| Baseline | 3.2 | 3.7 | 3.4 | 3.5 | 3.1 |
| Δ to placebo |  | −0.48 | −0.37 | −0.62 | −0.49 |
| p value |  | 0.0563 | 0.1442 | 0.013 | 0.0518 |

Figure 9I:
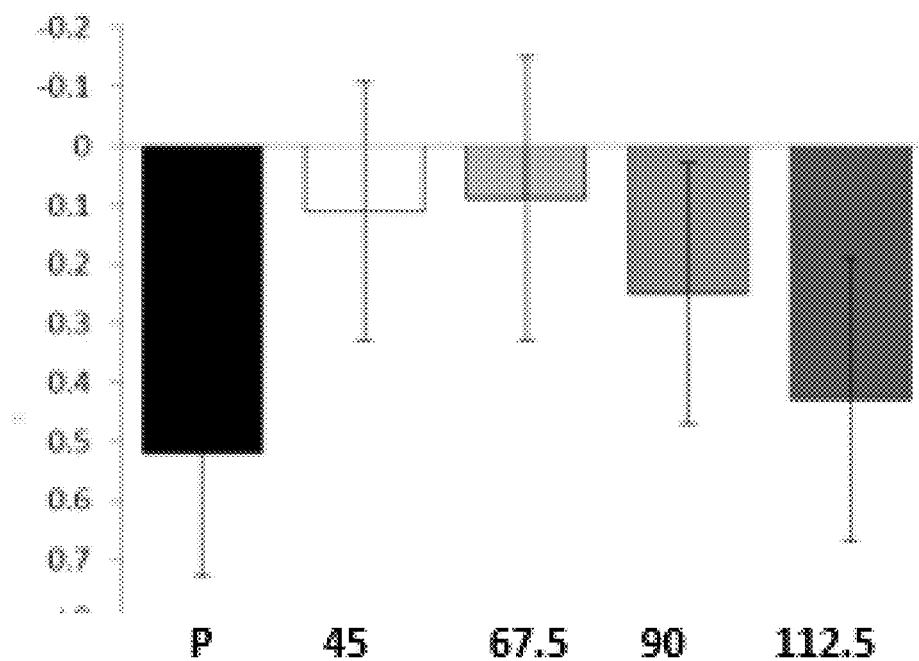

FIG. 9i: Change from baseline in UHDRS TMS Gait and Balance: Gait and balance scores at week 52 for patients with BL TFC≥7. The table below provides the P-Values corresponding to FIG. 9i. The table below and FIG. 9i show no significant improvement in the UHDRS TMS gait and balances in pridopidine treated HD1 and HD2 patients at 52 weeks.

|  | Placebo | 45 mg bid | 67.5 mg bid | 90 mg bid | 112.5 mg bid |
| --- | --- | --- | --- | --- | --- |
| N | 62 | 59 | 54 | 56 | 58 |
| Baseline | 3.2 | 3.7 | 3.4 | 3.5 | 3.1 |
| Δ to placebo |  | −0.41 | −0.43 | −0.28 | −0.09 |
| p value |  | 0.1811 | 0.1691 | 0.365 | 0.7719 |

FIGS. 9j-9m provide bar graphs of changes in UHDRS TMS Dystonia scores in 26 and 52 week patient groups.

Figure 9J:
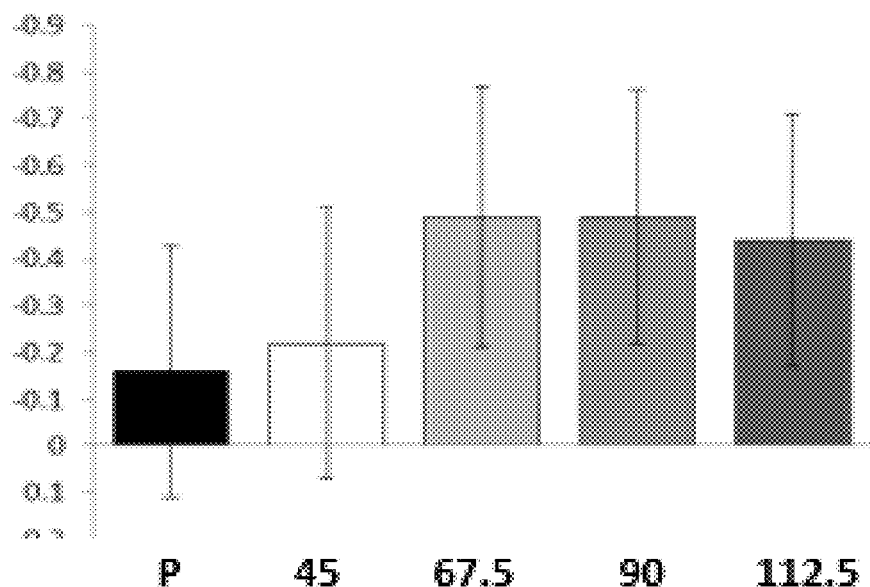

FIG. 9j: Change from baseline in UHDRS TMS Dystonia ALL: UHDRS TMS Dystonia scores at week 26 in all patients. The table below provides the P-Values corresponding to FIG. 9j. No significant improvement is observed.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 4.1 | 3.6 | 4.1 | 4.9 | 4.5 |
| Δ to placebo |  | −0.06 | −0.34 | −0.33 | −0.29 |
| p value |  | 0.8711 | 0.3778 | 0.3845 | 0.4507 |

Figure 9K:
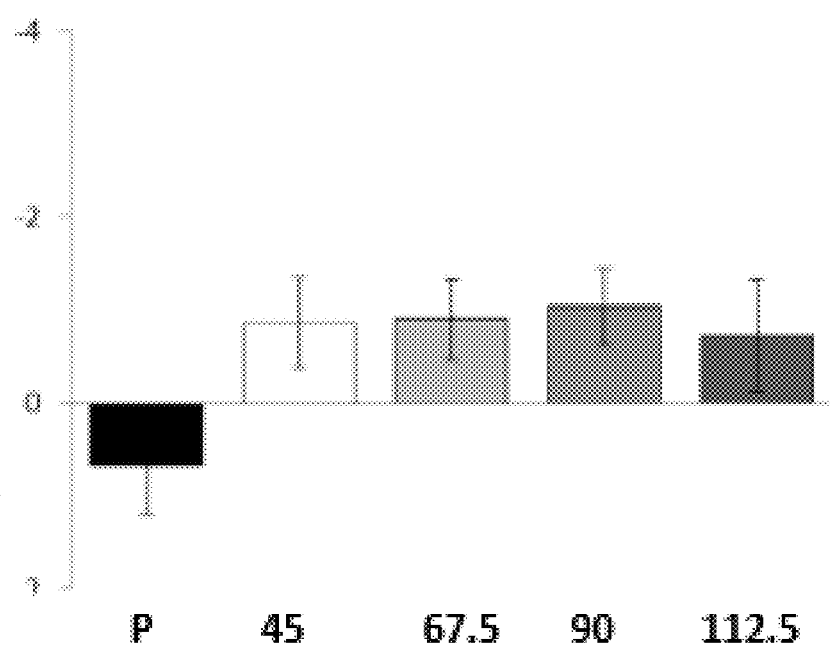

FIG. 9k: Change from baseline in UHDRS TMS Dystonia: UHDRS TMS Dystonia scores for patients with BL TFC≥9 AND CAG Repeats<44 at week 26. The table below provides the P-Values corresponding to FIG. 9k. Patients with baseline TFC greater than or equal to 9, show statistically significant improvement in the UHDRS TMS Dystonia score at 45 mg bid-90 mg bid pridopidine for 26 weeks.

|          | Placebo | 45 mg bid | 67.5 mg bid | 90 mg bid | 112.5 mg bid |
|----------|---------|-----------|-------------|-----------|--------------|
| N        | 13      | 15        | 19          | 22        | 11           |
| Baseline | 3.8     | 1.7       | 2.8         | 3.4       | 1.9          |
| Δ to placebo |     | −1.54     | −1.58       | −1.72     | −1.4         |
| p value  |         | 0.0313    | 0.0191      | 0.0078    | 0.0847       |

Figure 9L:
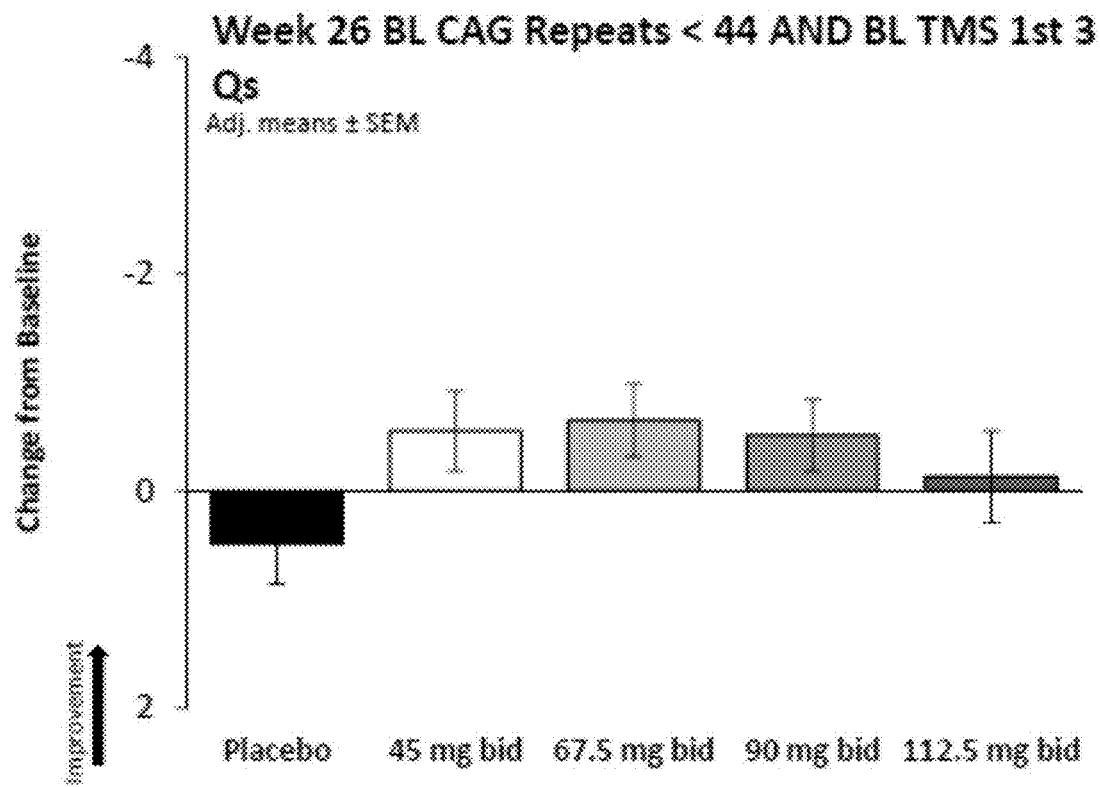

FIG. 9l: Change from baseline in UHDRS TMS Dystonia: UHDRS TMS Dystonia scores for patients with CAG Repeats<44 AND BL TMS 1st 3 Qs at week 26. The table below provides the P-Values corresponding to FIG. 9l. Patients with baseline TMS who represent three least severe TMS quarters and less than 44 CAG repeats in their htt gene, show statistically significant improvement in the UHDRS TMS Dystonia score at 45 mg bid-90 mg bid pridopidine for 26 weeks.

|          | Placebo | 45 mg bid | 67.5 mg bid | 90 mg bid | 112.5 mg bid |
|----------|---------|-----------|-------------|-----------|--------------|
| N        | 29      | 29        | 32          | 37        | 22           |
| Baseline | 3       | 2.6       | 2.6         | 2.9       | 2.6          |
| Δ to placebo |     | −1.04     | −1.15       | −1        | −0.62        |
| p value  |         | 0.0437    | 0.0235      | 0.0399    | 0.2655       |

Figure 9M:
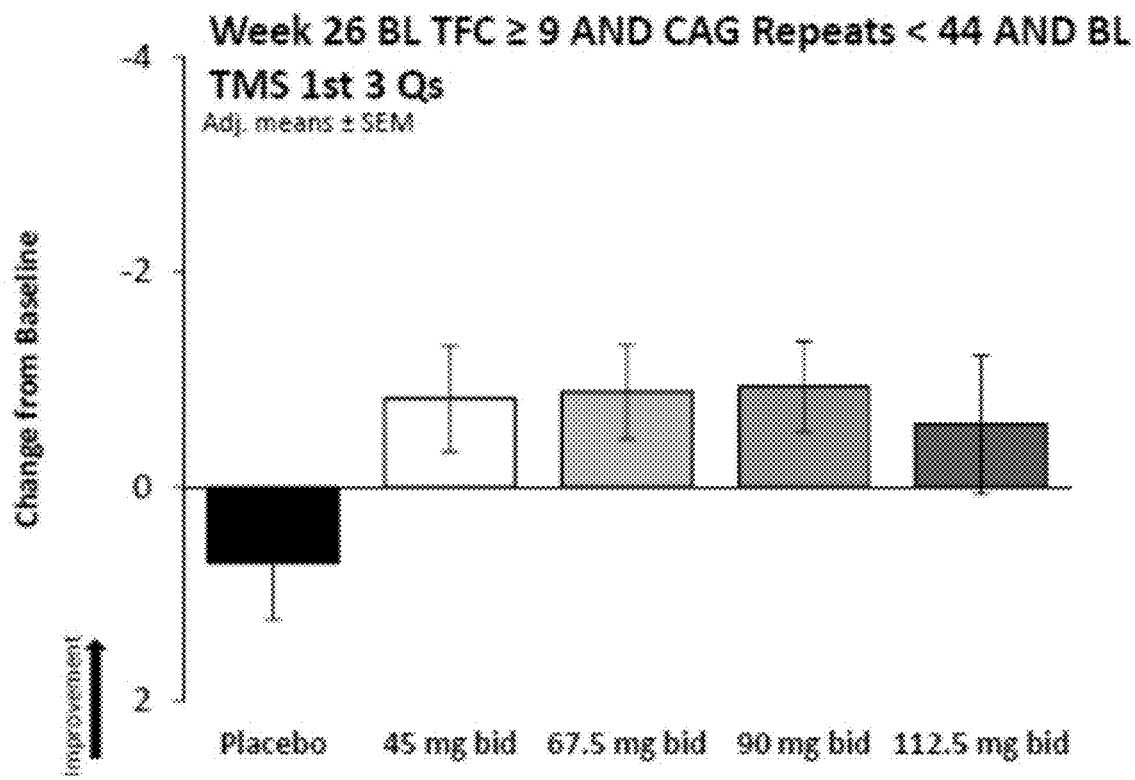

FIG. 9m: Change from baseline in UHDRS TMS Dystonia: UHDRS TMS Dystonia scores for patients with BL TFC≥9 and CAG Repeats<44 and BL TMS 1st 3 Qs at week 26. The table below provides the P-Values corresponding to FIG. 9m. Patients with baseline TFC greater than or equal to 9, baseline TMS representing three least severe TMS quarters and less than 44 CAG repeats in their htt gene, show statistically significant improvement in the UHDRS TMS Dystonia score at 45 mg bid 67.5 mg bid and 90 mg bid pridopidine for 26 weeks.

|          | Placebo | 45 mg bid | 67.5 mg bid | 90 mg bid | 112.5 mg bid |
|----------|---------|-----------|-------------|-----------|--------------|
| N        | 13      | 15        | 19          | 21        | 10           |
| Baseline | 3.8     | 1.7       | 2.8         | 3.1       | 2.1          |
| Δ to placebo |     | −1.53     | −1.6        | −1.64     | −1.29        |
| p value  |         | 0.0349    | 0.02        | 0.0132    | 0.1276       |

Figure 10A:
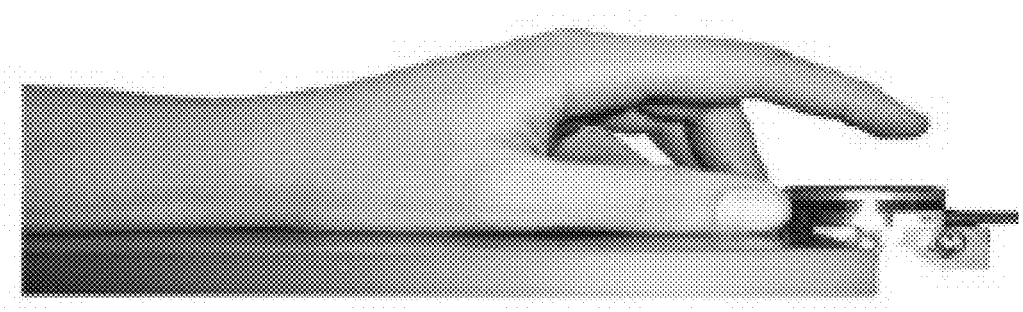
Figure 10B:
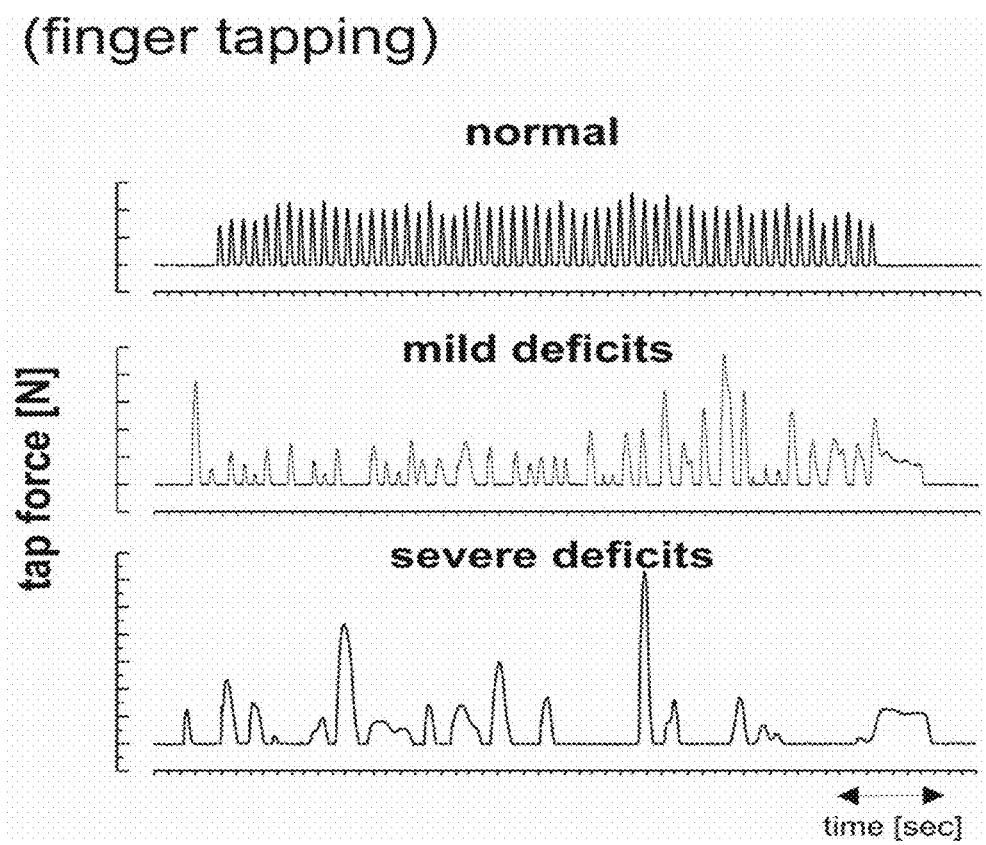

FIGS. 10a and 10b: General information regarding Finger tapping (Q-motor tap measurements). FIG. 10a shows a drawing of subject's arm with tapper. FIG. 10b shows normal and aberrant tapping measurements.

Figure 11A:
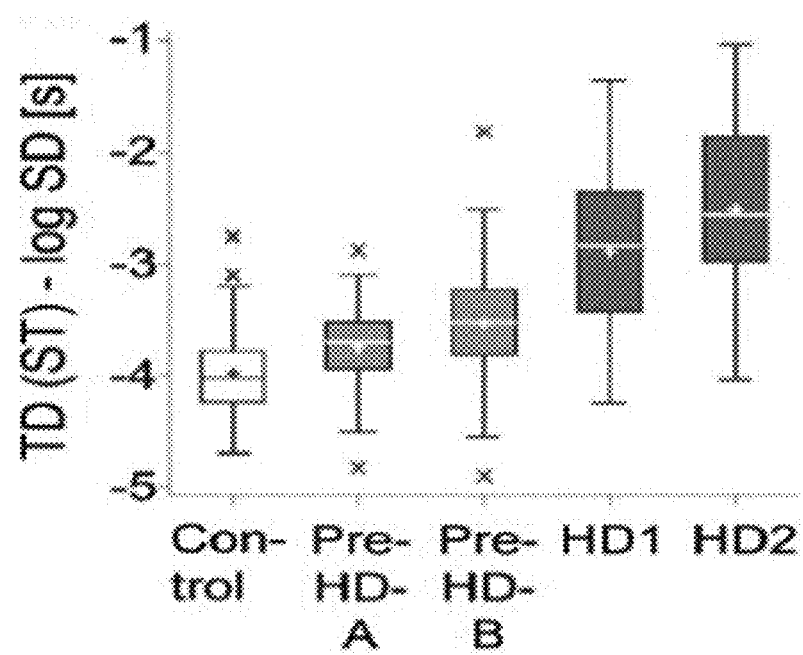
Figure 11B:
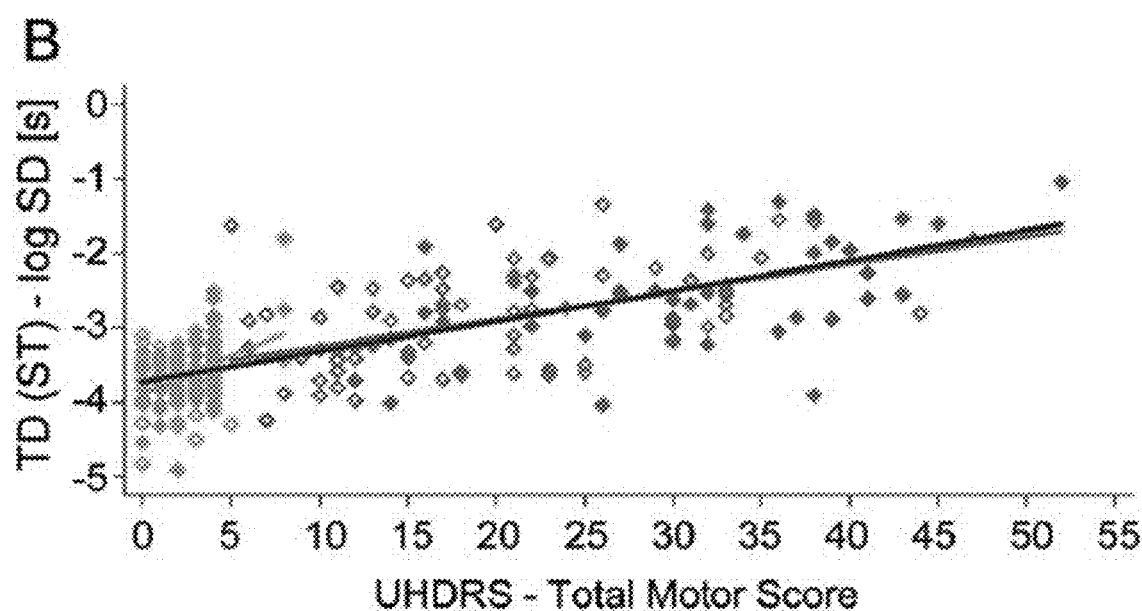

FIGS. 11a and 11b: Q-motor tap measurements: A well-validated objective measure. (Bechtel 2010)

Figure 12:
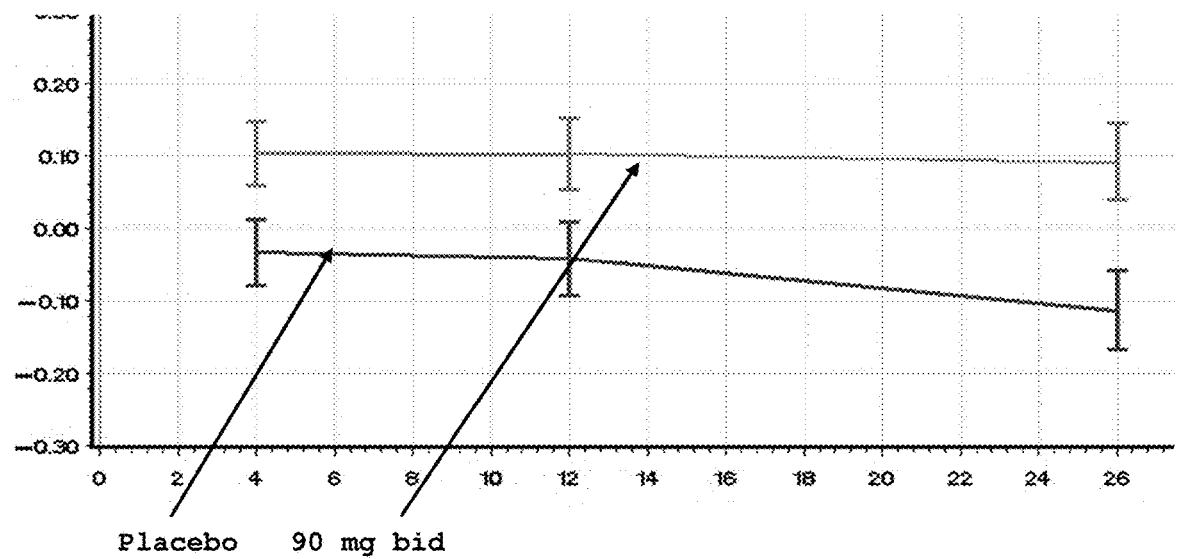

FIG. 12: Q-Motor Tap-Speed-Frequency. 90 mg pridopidine administered bid demonstrated consistent improvement from baseline. The data for 90 mg pridopidine bid is shown by the top line in this graph and the data for the placebo is shown by the bottom line in this graph. Difference in p-value of 90 mg pridopidine bid from placebo was 0.0259 at week 4, 0.0365 at week 12, and 0.0056 at week 26. Increase in tap speed indicates improvement. The unit of measurement of the Y-axis is Frequency (Hz).

Figure 13A:
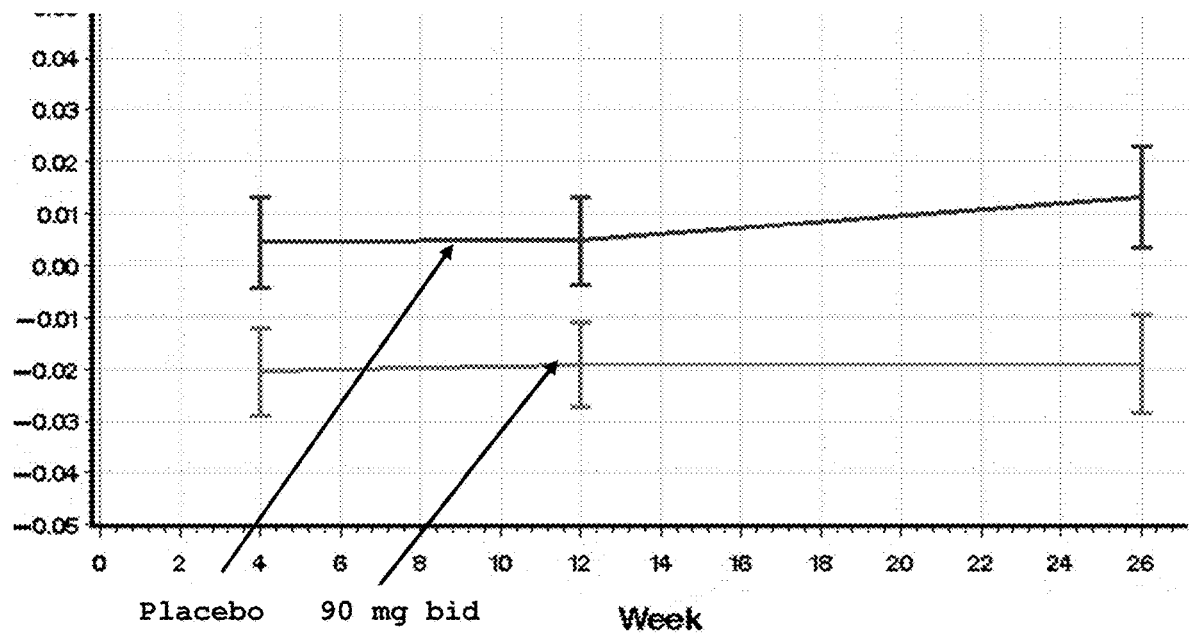
Figure 13B:
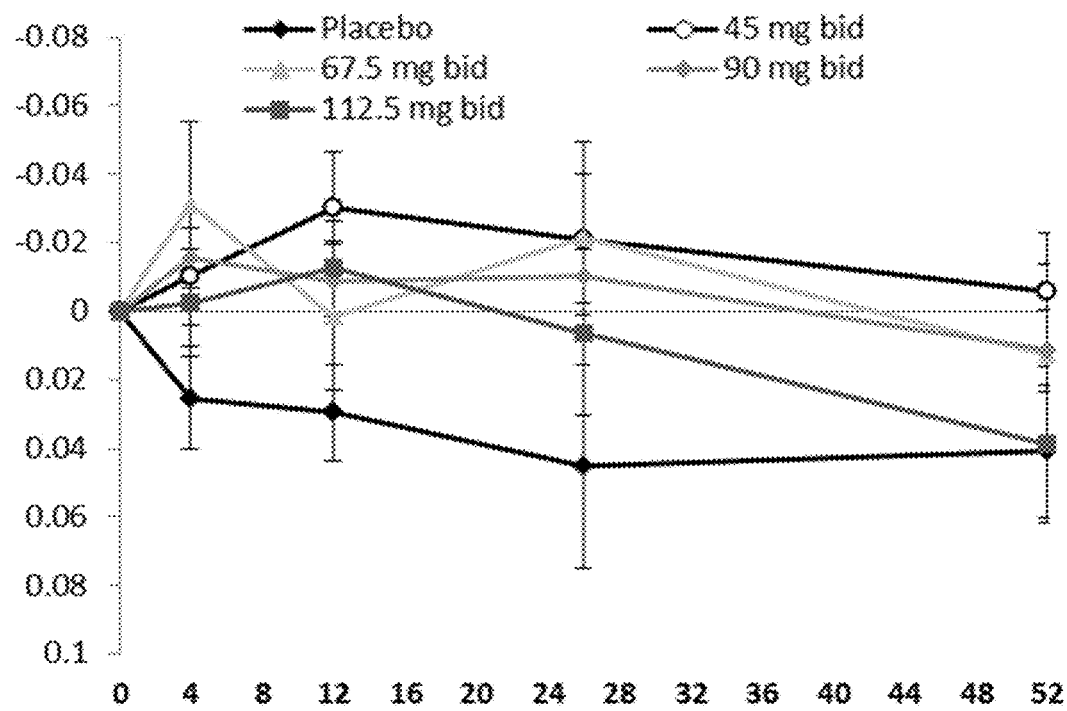

FIGS. 13a and 13b: Q-Motor Tap Speed Inter Onset interval (IOI). 90 mg pridopidine administered bid demonstrated consistent and significant improvement from baseline for 90 mg bid. The data for 90 mg pridopidine bid is shown by the bottom line in this graph and the data for the placebo is shown by the top line in this graph. Difference in p-value of 90 mg pridopidine bid from placebo was 0.0342 at week 4, 0.0368 at week 12, and 0.0162 at week 26. Decrease in inter tap interval indicates improvement. The unit of measurement of the Y-axis in FIG. 13a is Frequency (Hz). FIG. 13b shows change from baseline in Tap-Speed-Inter-Onset-interval-MN-Hand-L (sec) over time (weeks) for full analysis set.

Figure 13C:
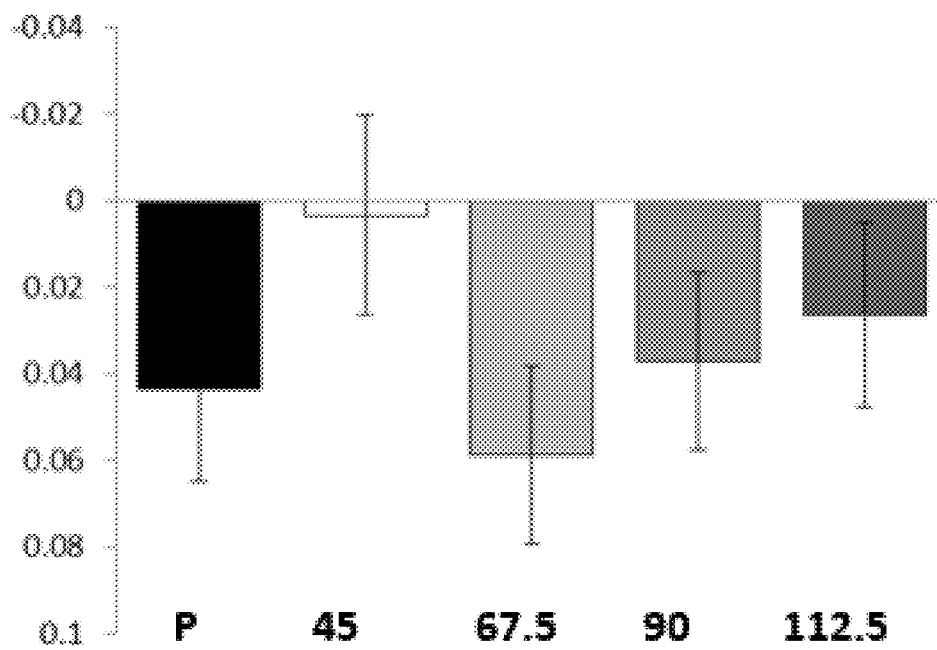

FIG. 13c: Improvement in objective pharmacodynamic measures of motor control: change from baseline in Q-Motor: Tap-Speed-Inter-Onset-interval-MN-Hand (sec), Week 52 FAS. The table below provides data and the P-Values corresponding to FIG. 13c. A trend towards improvement was noted in 45 mg bid treated patients.

|          | Placebo | 45 mg bid | 67.5 mg bid | 90 mg bid | 112.5 mg bid |
|----------|---------|-----------|-------------|-----------|--------------|
| N        | 81      | 75        | 79          | 81        | 81           |
| Baseline | 0.4065  | 0.4154    | 0.4608      | 0.4029    | 0.4366       |
| Δ to placebo |     | −0.0402   | 0.0152      | −0.0064   | −0.017       |
| p value  |         | 0.1956    | 0.6063      | 0.8258    | 0.5689       |

Figure 13D:
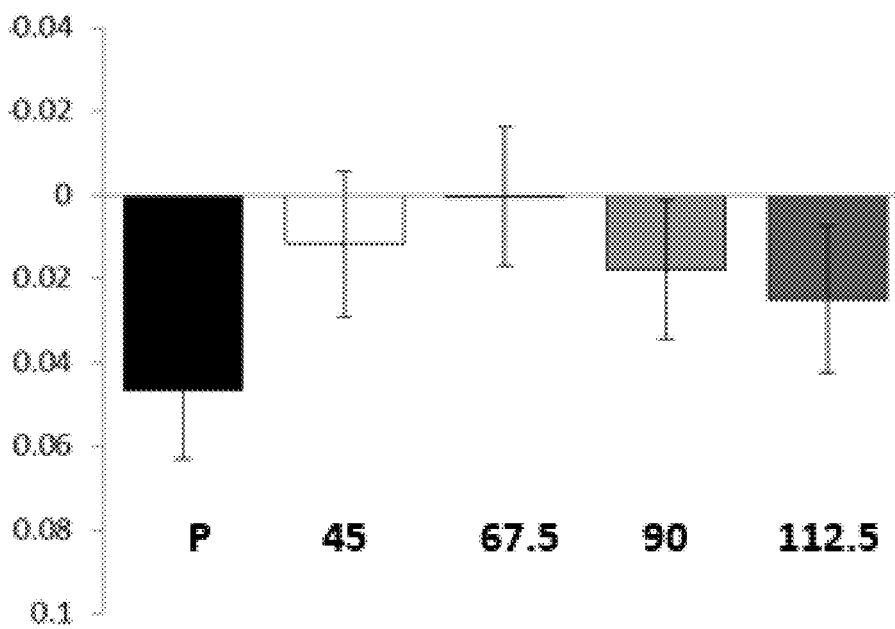

FIG. 13d: Improvement in objective pharmacodynamic measures of motor control: change from baseline in Q-Motor: Tap-Speed-Inter-Onset-interval-MN-Hand (sec), Week 52 in pridopidine treated HD1 and HD2 patients. The table below provides the data and P-Values corresponding to FIG. 13d. A trend towards improvement was noted in all treatment arms.

|          | Placebo | 45 mg bid | 67.5 mg bid | 90 mg bid | 112.5 mg bid |
|----------|---------|-----------|-------------|-----------|--------------|
| N        | 62      | 59        | 54          | 56        | 58           |
| Baseline | 0.3725  | 0.3605    | 0.3983      | 0.3789    | 0.4056       |
| Δ to placebo |     | −0.0351   | −0.0464     | −0.0291   | −0.022       |
| p value  |         | 0.1347    | 0.0449      | 0.2039    | 0.3509       |

Figure 13E:
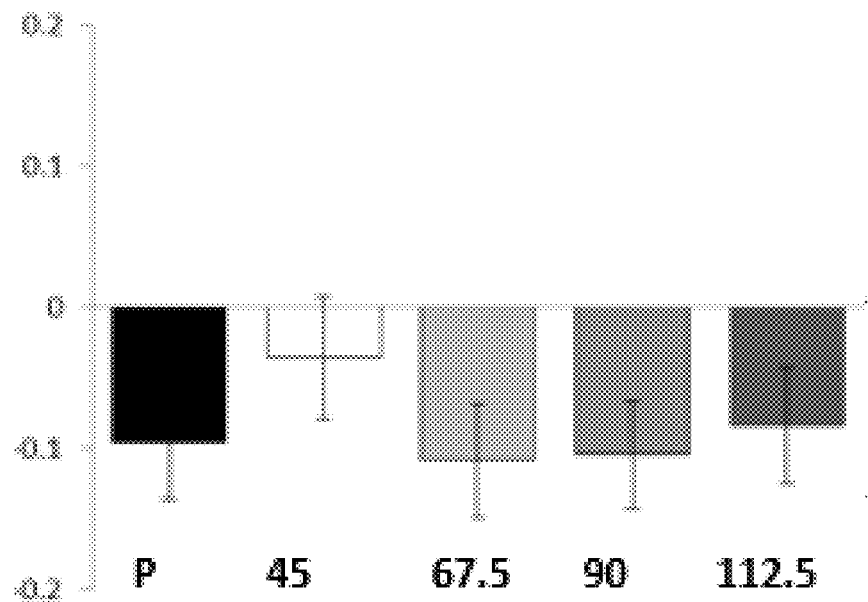

FIG. 13e: Improvement in objective pharmacodynamic measures of motor control, change from baseline in Q-Motor: Pro-Sup-Frequency-MN-Hand (Hz), Week 52 FAS. The table below provides the data and P-Values corresponding to FIG. 13e. A trend towards improvement was noted in 45 mg bid treated patients.

|          | Placebo | 45 mg bid | 67.5 mg bid | 90 mg bid | 112.5 mg bid |
|----------|---------|-----------|-------------|-----------|--------------|
| N        | 81      | 75        | 79          | 81        | 81           |
| Baseline | 1.6686  | 1.7789    | 1.7255      | 1.7505    | 1.7251       |
| Wk 52 Δ to placebo |  | 0.0599  | −0.0124     | −0.0087   | 0.0127       |
| p value  |         | 0.3122    | 0.8278      | 0.8763    | 0.8261       |

Figure 13F:
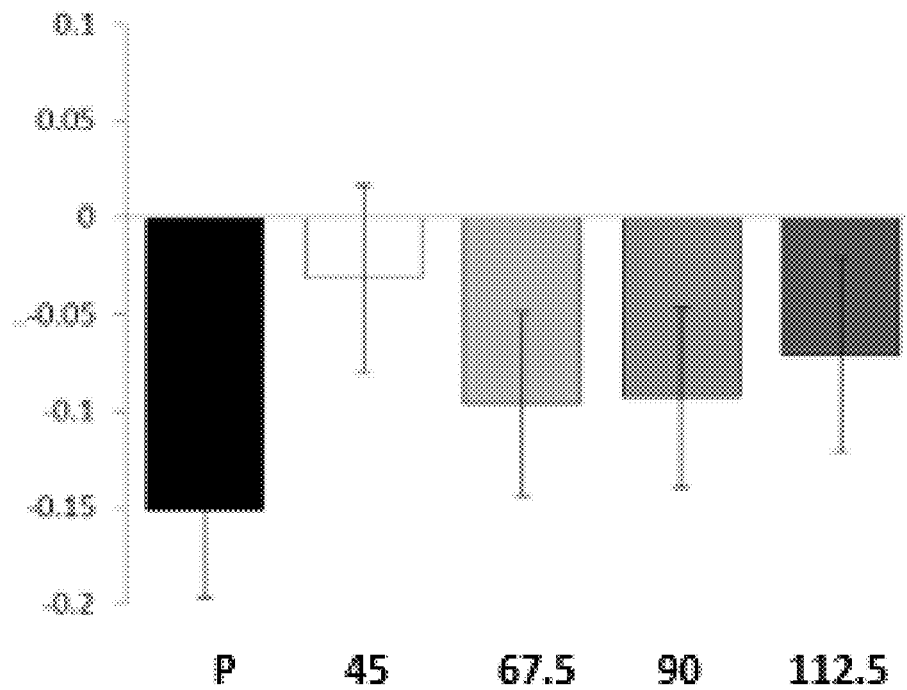

FIG. 13f: Improvement in objective pharmacodynamic measures of motor control, change from baseline in Q-Motor: Pro-Sup-Frequency-MN-Hand (Hz), Week 52 Week 52 in pridopidine treated HD1 and HD2 patients. The table below provides the data and P-Values corresponding to FIG. 13f. A trend towards improvement was noted in 45 mg bid treated patients.

|          | Placebo | 45 mg bid | 67.5 mg bid | 90 mg bid | 112.5 mg bid |
|----------|---------|-----------|-------------|-----------|--------------|
| N        | 62      | 59        | 54          | 56        | 58           |
| Baseline | 1.77    | 1.8513    | 1.8928      | 1.8658    | 1.841        |

-continued

| | Placebo | 45 mg bid | 67.5 mg bid | 90 mg bid | 112.5 mg bid |
|---|---|---|---|---|---|
| Wk 52 Δ to placebo | | 0.1195 | 0.0548 | 0.0575 | 0.08 |
| p value | | 0.0692 | 0.3996 | 0.3709 | 0.229 |

Figure 14:
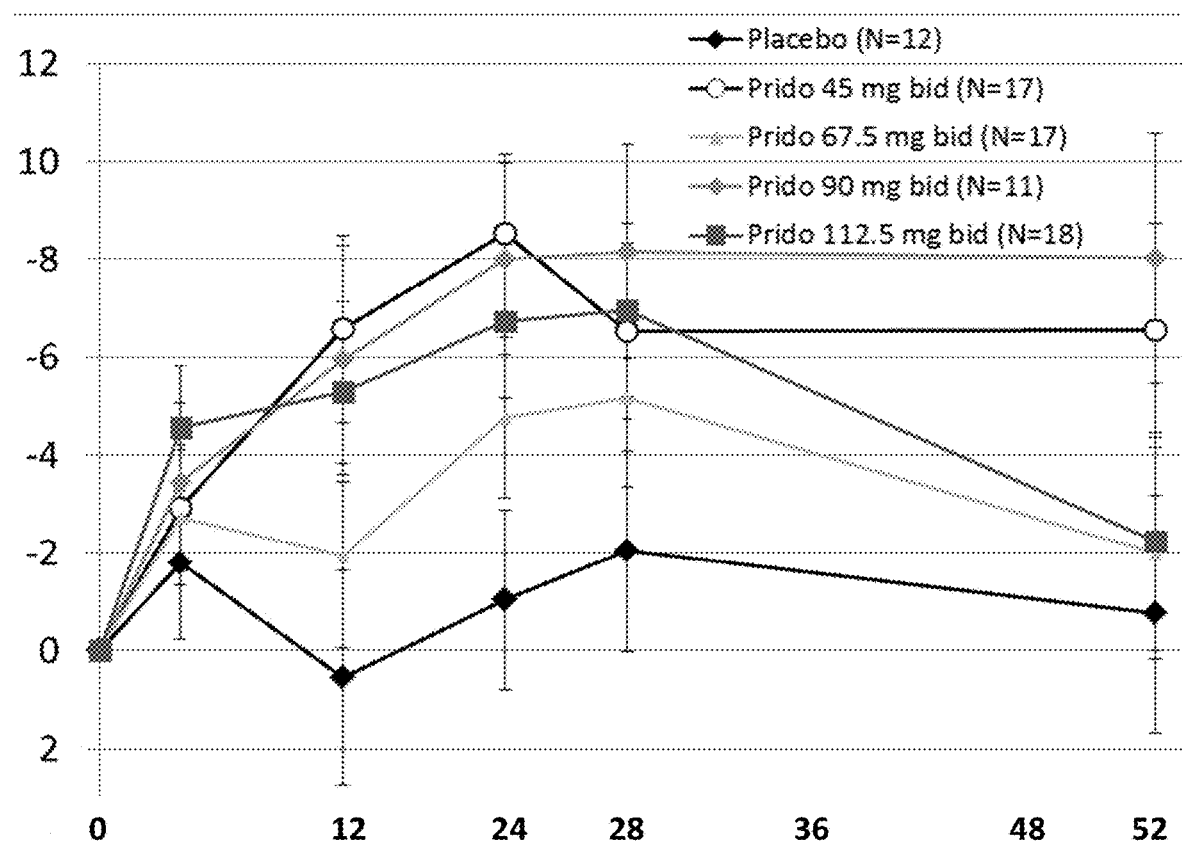

FIG. 14: Change from baseline in UHDRS-TMS plotted over time in HD1 patients. Line with dark diamond represents placebo; line with open circle represents 45 mg bid, line with triangle represents 67.5 mg bid, line with grey diamond represents 90 mg bid, line with square represents 112.5 mg bid. 45 mg bid shows improvement in TMS score after 52 weeks. Y axis represents change from baseline in TMS from baseline, x axis represents treatment time in weeks. (Adj. means±SEM)

Figure 15:
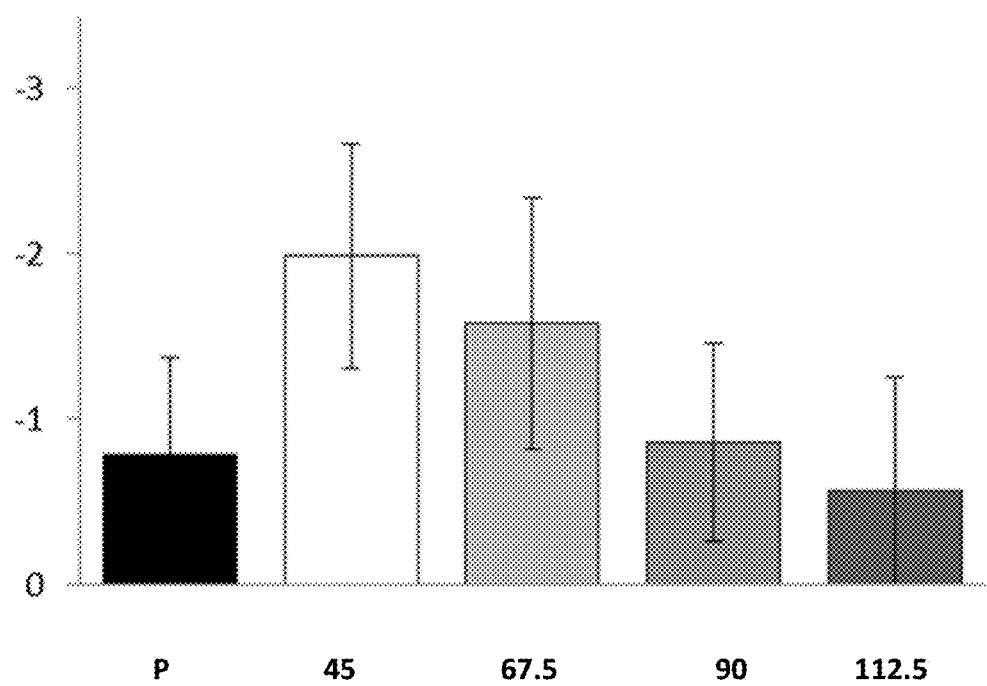

FIG. 15: Comparison of patients with baseline (BL) dystonia score of ≥4 at 52 weeks after dosage with either placebo, 45 mg pridopidine b.i.d, 67.5 mg pridopidine b.i.d., 90 mg pridopidine b.i.d., or 112.5 mg pridopidine b.i.d. Within the full analysis set, no clinically meaningful changes from baseline were noted for patients at Week 26 or Week 52 in the dystonia score across the placebo and all active treatment groups (not shown). In patients with a baseline total dystonia score≥4 assessed at Week 52, a directional clinical improvement in dystonia was noted for all treatment groups, with the greatest decreases observed for the 45, 67.5, and 90 mg bid treatment groups.

Figure 16A:
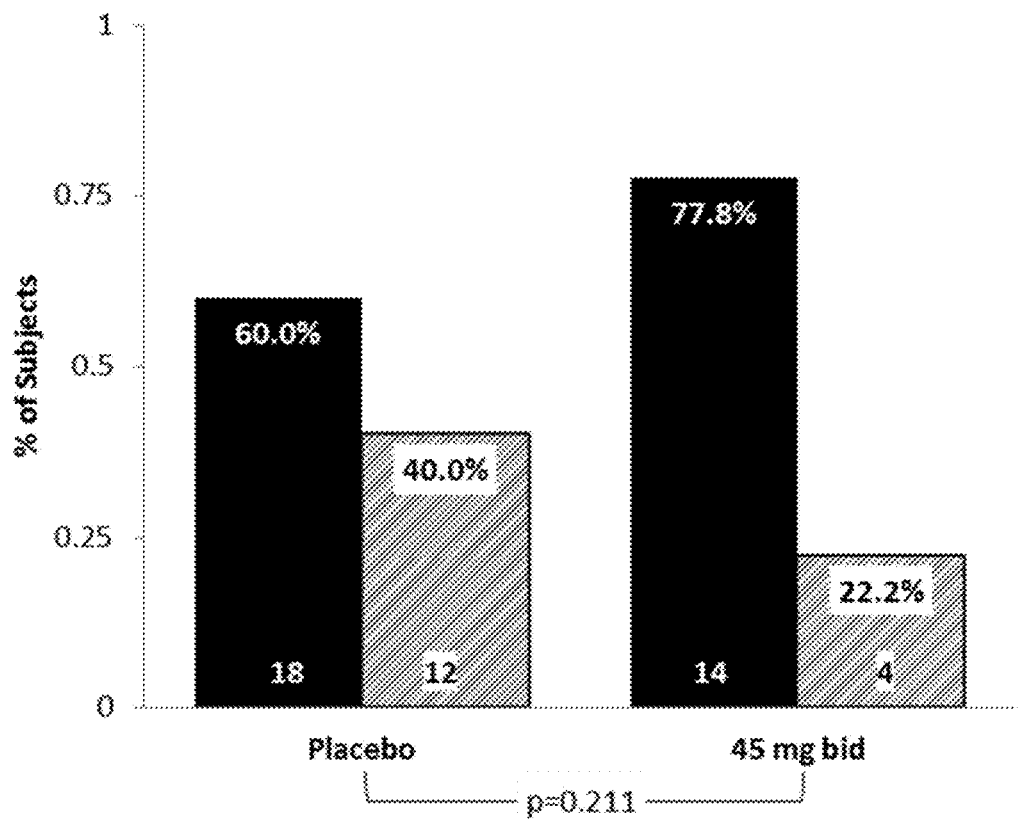

FIG. 16a: Of those patients with baseline (BL) dystonia score of ≥4 who completed 52 weeks of treatment with either placebo or 45 mg pridopidine b.i.d., the percentage who were categorized based on the change in UHDRS TMS dystonia from BL to 52 weeks as responders (improved or no change, e.g. change≥0) or non-responders (worsened, change<0).

Figure 16B:
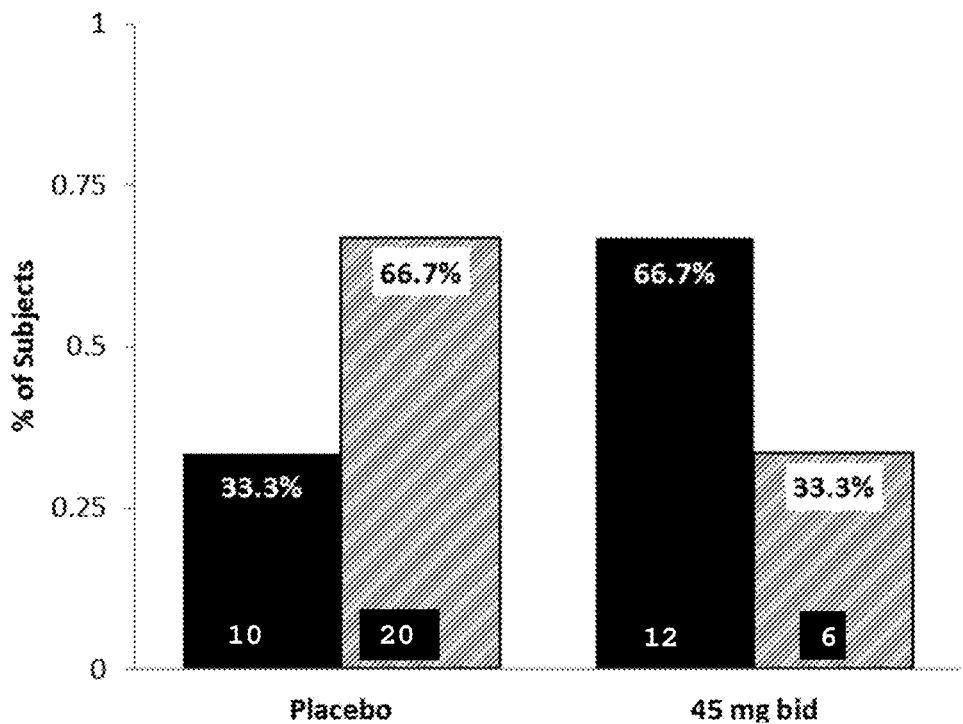

FIG. 16b: Of those patients with baseline (BL) dystonia score of >4 who completed 52 weeks of treatment with either placebo or 45 mg pridopidine b.i.d., the percentage who were categorized based on the change in UHDRS TMS dystonia from BL to 52 weeks as responders (improved, e.g. change≥1) or non-responders (worsened or no change<1).

Results of the Responder Analysis for dystonia items (FIGS. 16a and 16b) further support this trend toward improvement by showing that a greater percentage of patients were categorized as Responders within the dystonia items in the 45 mg bid treatment group compared to the placebo group (14 patients [77.8%] and 18 patients [60.0%], respectively in FIGS. 16a and 66.7% and 33.3%, respectively in FIG. 16b). A similar trend of Responders was seen in the chorea+dystonia items in the 45 mg bid treatment group compared to the placebo group (14 patients [77.8%] and 20 patients [66.7%], respectively) (not shown).

Figure 17:
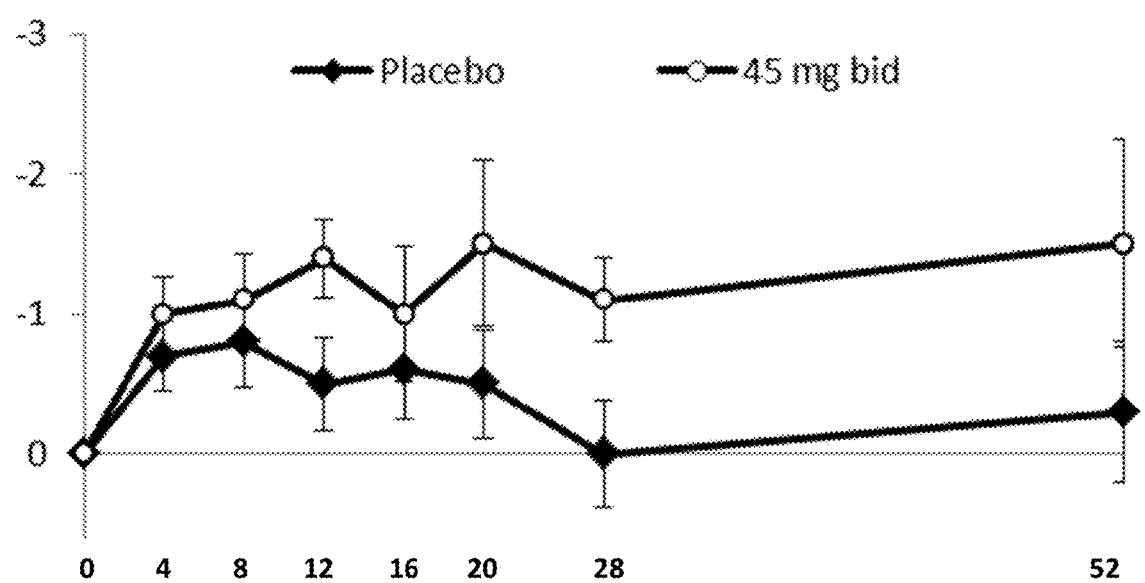

FIG. 17: Plot of change in UHDRS Dystonia score over time for subjects pooled from MermaiHD, HART and Pride-HD studies with baseline (BL) dystonia (≥4) who received either placebo or 45 mg pridopidine b.i.d. At Week 26, patients taking 45 mg pridopidine b.i.d showed a statistically significant improvement in the dystonia score compared to those taking placebo. A trend toward this improvement was maintained at Week 52.

Figure 18:
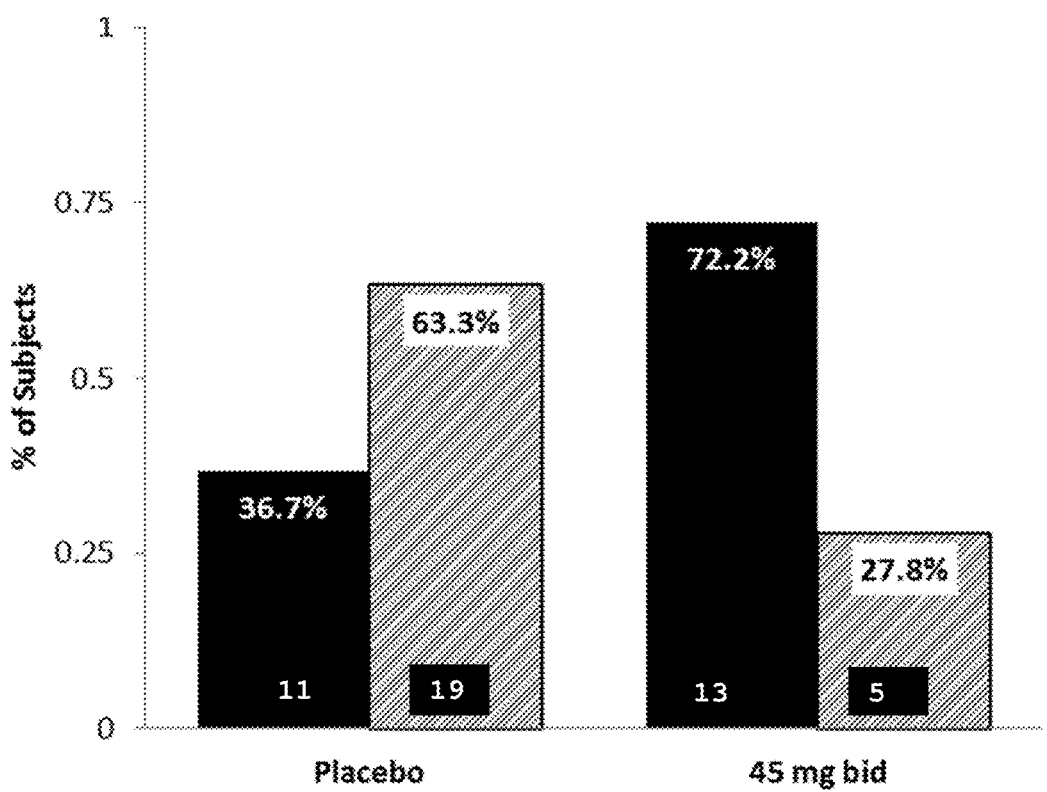

FIG. 18: Of those PRIDE-HD patients with baseline (BL) dystonia score of ≥4 who completed 52 weeks of treatment with either placebo or 45 mg pridopidine b.i.d., the percentage who were categorized based on the change in UHDRS limb dystonia from BL to 52 weeks as responders (improved, e.g. change >1) or non-responders (worsened or no change<1).

A statistically significant greater percentage of patients were categorized as Responders for the UHDRS-Limb Dystonia item in the pridopidine 45 mg bid treatment group compared to the placebo group (77.2% and 36.7%, respectively).

Figure 19A:
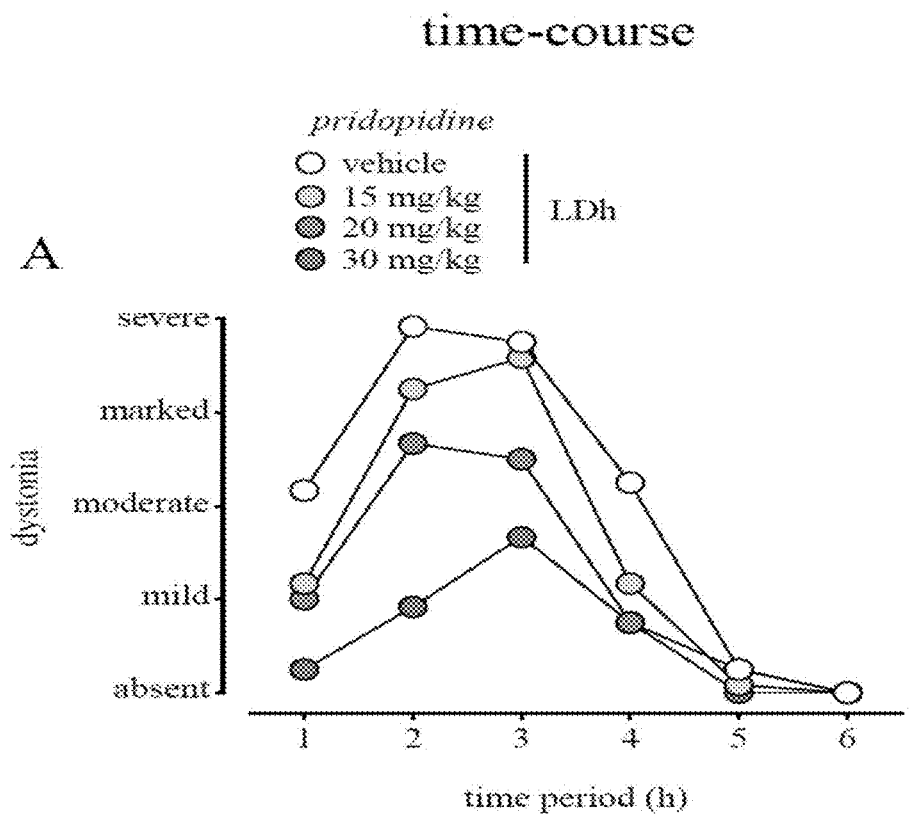
Figure 19B:
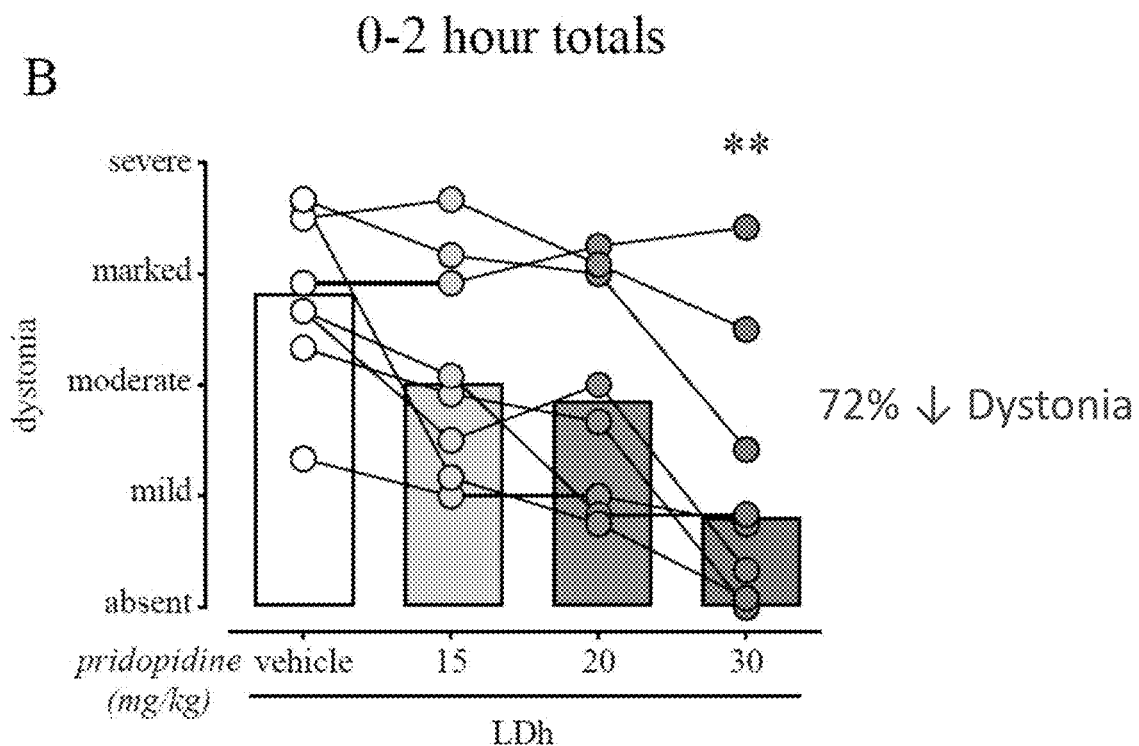

FIGS. 19A and 19B present levels of dystonia over a 6 h period and cumulated in either 1 h epochs (FIG. 19A) or cumulated across the 0-2 h period of peak-effect (FIG. 19B). Data are median (FIG. 19A) with individual values (FIG. 19BB). N=8 for all treatment groups. *//* represents P<0.05, P<0.01 or P<0.001 cf vehicle-treatment. 2-way RM ANOVA (FIG. 19A) with Holm-Sidak's test or Friedman test with Dunn's test (FIG. 19B).

| | LDh-vehicle cf. (h) | | | | | |
|---|---|---|---|---|---|---|
| Pridopidine | 1 | 2 | 3 | 4 | 5 | 6 |
| 15 mg/kg | ns | ns | ns | ns | ns | ns |
| 20 mg/kg | * | ns | ns | ns | ns | ns |
| 30 mg/kg | ** | *** | * | ns | ns | ns |

DETAILED DESCRIPTION OF THE INVENTION

This invention provides a method of treating a subject afflicted with a dystonia, comprising periodically administering to the subject a pharmaceutical composition comprising an amount of pridopidine effective to treat the subject.

This invention provides a method of treating a subject afflicted with a dystonia comprising periodically administering to the subject a pharmaceutical composition comprising an amount of pridopidine or its pharmaceutically acceptable salt, effective to treat the subject, wherein the dystonia is a primary dystonia, an isolated dystonia, an early onset generalized dystonia, a secondary dystonia, a focal dystonia, a segmental dystonia, a multifocal dystonia, a hemidystonia, a generalized dystonia, paroxysmal dystonia, Blepharospasm (Benign Essential Blepharospasm[BEB]), Cervical Dystonia (Spasmodic Torticollis[ST]), Acquired Dystonia, Oromandibular Dystonia, Embouchure dystonia, Paroxysmal Dystonia Choreoathetosis, Paroxysmal nonkinesigenic dyskinesia (PKND), Spasmodic Dysphonia (SD), Spasmodic Torticollis (Cervical Dystonia), Tardive Dystonia, writer's Cramp dystonia or any combination thereof.

This invention further provides a method of treating a subject afflicted with a dystonia as a symptom of a disorder comprising: Huntington disease, Parkinson disease, Alzheimer disease, Wilson's disease, Multiple Sclerosis, birth injury, disorders that develop in some people with cancer (paraneoplastic syndromes), oxygen deprivation or carbon monoxide poisoning, infections such as HIV, tuberculosis or encephalitis, reactions to certain medications or heavy metal poisoning, comprising periodically administering to the subject a pharmaceutical composition comprising an amount of pridopidine or its pharmaceutically acceptable salt effective to treat the subject or a genetic dystonias.

In some embodiments, the subject is not afflicted with Huntington's disease.

In some embodiments, the subject is not a Huntington's disease subject.

In one embodiment, the dystonia is a primary dystonia or an isolated dystonia. In another embodiment, the dystonia is a primary generalized dystonia. In another embodiment, the dystonia is a genetic form of primary dystonia. In another embodiment, the dystonia is an early onset generalized dystonia.

In one embodiment, the dystonia is Torsion dystonia-1 (DYT1) dystonia. In another embodiment, the dystonia is DYT6 dystonia or DYT-KMT2B (DYT28) dystonia. In one embodiment, the DYT1 dystonia is postural type dystonia or action type dystonia.

In some embodiments, the dystonia is early onset dystonia or late onset dystonia. In some embodiments, the dystonia manifests at any age. In some embodiments, the dystonia is an early onset generalized dystonia (DYT1 and non-DYT1).

In some embodiments, the dystonia is an isolated or a combined dystonia.

In some embodiment, the dystonia is a secondary dystonia or a combined dystonia.

In one embodiment, the dystonia is Dopa-responsive dystonia, Myoclonus dystonia, X-linked dystonia-parkinsonism, or Rapid-onset dystonia-parkinsonism.

In some embodiments, the dystonia is a focal dystonia, a segmental dystonia, a multifocal dystonia, a hemidystonia or a generalized dystonia.

In one embodiment, the dystonia is a paroxysmal dystonia. In another embodiment the dystonia is action-specific dystonia or a task-specific dystonia. In one embodiment, the dystonia is Musician's dystonia.

In one embodiment, the dystonia is not caused by a pathology. In some embodiments, the pathology is a stroke, a traumatic brain injury, a lesion, a brain tumor, neurological tissue damage, or neurological tissue degeneration.

In some embodiments, the dystonia is Musician's dystonia, Dopa-responsive dystonia, Myoclonus dystonia, Paroxysmal dystonia and dyskinesia, X-linked dystonia-parkinsonisms, Rapid-onset dystonia-parkinsonisms, Primary dystonia, Secondary dystonia (including Huntington's dystonia), or Psychogenic dystonia.

In one embodiment, the dystonia is postural dystonia. In another embodiment, the dystonia is action dystonia.

In an embodiment, the subject has been confirmed to be afflicted with DYT1 or other primary genetic forms of dystonia by genetic testing. In an embodiment, the subject has a Burke-Fahn-Marsden Dystonia Rating Scale (BFMDRS) score greater than 6.

In one embodiment, the subject has a 3-base pair in-frame deletion within the coding region of the TOR1A (torsinA) gene located on chromosome 9q34.

In one embodiment, the subject does not suffer from cognitive impairment. In another embodiment, the subject suffers from a cognitive impairment.

In an embodiment, the amount of pridopidine is effective to reduce or maintain a level of one or more symptoms of the dystonia in the subject. In an embodiment, the symptoms are measured by the Burke-Fahn-Marsden Dystonia Rating Scale or the Unified Dystonia Rating Scale. In another embodiment, the symptoms are measured by the Clinical Global Impression (CGI) scale, Patient Global Assessment score, Visual Analogue Score for pain, Patient Evaluation of Global Response, Burke-Fahn-Marsden Disability Scale (BFMDS), or the Health Related quality of life score (EQ-5D, SF-36).

In one embodiment, the one or more symptom is dystonia.

In an embodiment, the one or more symptoms are selected from the group consisting of: involuntary limb movement or muscle contractions; twisted posture of the limbs or trunk; abnormal fixed posture of the limbs or trunk; talipes equinovarus; turning in of the leg; turning in of the arm; tremor of the hand, head, trunk or arms; dragging of the leg; torticollis; writer's cramp; and dystonia of trunk and/or extremities.

In one embodiment, the amount of pridopidine is effective to provide a clinically significant improvement in dystonia symptoms. In an embodiment, the clinically significant improvement in dystonia symptoms is an at least a 20% change from baseline in the subject administered pridopidine in comparison to a human patient not treated with pridopidine as measured by a rating scale used in clinical practice or clinical research. In an embodiment, the rating scale used in clinical practice or clinical research is the dystonia items of the UHDRS scale or the Burke-Fahn-Marsden Dystonia Rating Scale. In some embodiments, a clinically significant improvement in dystonia symptoms is considered to be at least a 20% change from baseline in a pridopidine treated patient compared to placebo treated patient (a patient not receiving pridopidine) when measured using a rating scale used in clinical practice or clinical research such as, for example, the dystonia items of the UHDRS scale or BFMDRS. In some embodiments, a clinically significant improvement is at least a 25% change from baseline, a 30% change from baseline, a 40% change from baseline or a greater than 50% change from baseline.

In an embodiment, the subject is a human patient. In another embodiment, the subject is a mammal. In one embodiment, the periodic administration is oral.

In an embodiment, between 22.5-315 mg pridopidine is administered to the patient per day. In another embodiment, 22.5 mg, 45 mg, 67.5 mg, 90 mg, 100 mg, 112.5 mg, 125 mg, 135 mg, 150 mg, 180 mg, 200 mg, 250 mg, or 315 mg pridopidine is administered to the patient per day.

In an embodiment, the amount of pridopidine is administered by a unit dose of 22.5 mg, 45 mg, 67.5 mg, 90 mg, 100 mg, 112.5 mg, 125 mg, 135 mg, 150 mg, 180 mg, 200 mg, 250 mg, or 315 mg pridopidine.

In an embodiment, the unit dose is administered once daily.

In an embodiment, the unit dose is administered more than once daily. In another embodiment, the unit dose is administered twice per day.

In an embodiment, the pridopidine is in the form of pridopidine hydrochloride.

The invention also provides pridopidine for use in treating a subject afflicted with a dystonia.

The invention also provides pridopidine for the manufacture of a medicament for use in treating a subject afflicted with a dystonia.

The invention also provides a pharmaceutical composition comprising an effective amount of pridopidine for treating a dystonia The invention also provides a pharmaceutical composition comprising pridopidine or for use in treating a subject suffering from a dystonia.

The invention also provides a package comprising:
a) a pharmaceutical composition comprising an amount of pridopidine; and
b) instructions for use of the pharmaceutical composition to treat a subject afflicted with a dystonia.

The invention also provides a therapeutic package for dispensing to, or for use in dispensing to, a subject afflicted with dystonia, which comprises:
a) one or more unit doses, each such unit dose comprising an amount of pridopidine thereof, wherein the amount of said pridopidine in said unit dose is effective, upon administration to said subject, to treat the subject, and b) a finished pharmaceutical container therefor, said container containing said unit dose or unit doses, said container further containing or comprising labeling directing the use of said package in the treatment of said subject.

Combinations of the above-described embodiments are also within the scope of the invention.

Each embodiment disclosed herein is contemplated as being applicable to each of the other disclosed embodiments. For instance, all combinations of the various elements described herein are within the scope of the invention. Additionally, the elements recited in the packaging and pharmaceutical composition embodiments can be used in the method and use embodiments described herein.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of Remington's Pharmaceutical Sciences (Mack Publishing Co., Easton, PA).

Terms

As used herein, and unless stated otherwise, each of the following terms shall have the definition set forth below.

The articles "a", "an" and "the" are non-limiting. For example, "the method" includes the broadest definition of the meaning of the phrase, which can be more than one method.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a movement disorder. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives As used herein, to "treat" or "treating" encompasses, e.g., reducing a symptom, inducing inhibition, regression, or stasis of the disorder and/or disease. As used herein, "inhibition" of disease progression or disease complication in a subject means preventing or reducing the disease progression and/or disease complication in the subject.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition. The administration can be periodic administration.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times a week and so on, etc.

"Dystonia" as referred to herein is a movement disorder characterized by sustained or intermittent muscle contractions causing abnormal, often repetitive, movements, postures, or both. Dystonic movements are typically patterned, twisting, and may be tremulous. Dystonia is often initiated or worsened by voluntary action and associated with overflow muscle activation (Albanese 2013a).

As used herein, an "amount" or "dose" of pridopidine as measured in milligrams refers to the milligrams of pridopidine present in a preparation, regardless of the form of the preparation. A "dose of 90 mg pridopidine" means the amount of pridopidine acid in a preparation is 90 mg, regardless of the form of the preparation. Thus, when in the form of a salt, e.g. a pridopidine hydrochloride, the weight of the salt form necessary to provide a dose of 90 mg pridopidine would be greater than 90 mg due to the presence of the additional salt ion.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1; 0.2 . . . 0.9; and 1, 2 . . . 49 mg unit amounts are included as embodiments of this invention.

As used herein, "pridopidine" means pridopidine base or a pharmaceutically acceptable salt thereof, as well as derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. In certain embodiments, pridopidine is a pharmaceutically acceptable salt, such as the HCl salt or tartrate salt. Preferably, in any embodiments of the invention as described herein, the pridopidine is in the form of its hydrochloride salt.

"Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the L-tartrate, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Dystonia Rating Scales

Albanese et al, (2013b) describes the results of a task force convened to critique existing dystonia rating scales and place them in clinical and clinimetric context.

Listing of Abbreviations

The following abbreviations are used throughout this application:

ALT: alanine aminotransferase; ADL: Activities of Daily Living; AR: Autoregressive; AUC: area under the concentration-time curve; bid or b.i.d.: twice daily; BL=Baseline; CAB: cognitive assessment battery; CGI-C: Clinical Global Impression of Change; CGI-S: Clinical Global Impression of Severity; CI: confidence interval; CIBIC-Plus: Clinician's Interview-based Impression of Change plus Caregiver Input; CIBIS: Clinician's Interview-based Impression of Severity; CIOMS: Council for International Organizations of Medical Sciences; Cmax: maximum observed plasma drug concentration; CNS: central nervous system; CRF: case report form; CRO: contract research organization; CS: Compound Symmetry; C-SSRS: Columbia-Suicide Severity Rating Scale; CYP: cytochrome P450; DSM-IV TR: Diagnostic and Statistical Manual—Fourth Edition Text Revision; EM: extensive metabolizers; EU: European Union; FA: Functional Assessment; FAS: full analysis set; Freq: tapping frequency; GCP: Good Clinical Practice; GFV-C: grip force variability in the static phase; GGT: gamma-glutamyl transpeptidase; HART: Huntington's disease ACR16 Randomized Trial; HCG: human chorionic gonadotropin; HD: Huntington's disease; HD-QoL=Huntington's disease Quality of Life; HVLT-R: HAD-CAB Hopkins Verbal Learning Test-Revised; ICH:

International Conference on Harmonisation; IEC: Independent Ethics Committee; IOI: inter onset interval; IPI: inter peak interval; IRB: Institutional Review Board; IRT: interactive response technology; IS: Independence Score; ITI: inter tap interval; ITT: intent-to-treat; LSO: local safety officer; MAD: multiple ascending dose; MedDRA: Medical Dictionary for Regulatory Activities; MermaiHD: Multinational European Multicentre ACR16 study in Huntington's Disease; ML: Maximum-Likelihood; mMS: Modified Motor Score; MoCA: Montreal cognitive assessment; MS: Multiple sclerosis; MTD: maximum tolerated dose; NMDA: N-methyl-D-aspartate; NOAEL: no observed adverse effect level; PBA-s: Problem Behaviors Assessment-Short form; PD: pharmacodynamic(s); PDS: Physical disability scale; PK: pharmacokinetic(s); PM: poor metabolizer; PPT: physical performance test; Qd: once daily; Q-Motor: Quantitative motor; QoL: Quality of life; QTcF: Fridericia-corrected QT interval; RBC: red blood cell; REML: Restricted Maximum-Likelihood; SAE: serious adverse event; SD: standard deviation; SDMT: symbol digit modalities test; SOC: system organ class; SOP: standard operating procedure; SUSAR: suspected unexpected serious adverse reaction; t½: half life; TC=telephone call; TD: tap duration; TF: tapping force; TFC: Total Functional Capacity; TMS: Total Motor Score; TMS Involuntary Movements=TMS for performance of Domestic Chores and Dystonia scores combined. TUG: timed up and go; UHDRS: Unified Huntington's Disease Rating Scale; ULN: upper limit of the normal range; US: United States; WBC: white blood cell; WHO: World Health Organization; WHO: Drug World Health Organization (WHO) drug dictionary; $\Delta$HR: change from baseline in heart rate; $\Delta$QTcF: change from baseline in QTcF; $\Delta\Delta$HR: placebo-corrected change from baseline in heart rate; Placebo-Controlled Study—Huntington's Disease; $\Delta\Delta$QTcF: placebo-corrected change from baseline in QTcF, wk: week; EQ5D-5L European Quality of Life-5 Dimensions (5 levels).

Clinical Studies

Sixteen (16) clinical studies have been completed with pridopidine, including 8 studies in healthy subjects (of which 1 study also included patients with schizophrenia), 1 study in patients with Parkinson's disease, 2 studies in patients with schizophrenia (including the study mentioned above), and 6 studies in patients with HD (including 1 open-label extension study). In addition, a compassionate use program for pridopidine in patients with HD is ongoing in Europe, and an open-label, long term safety study is ongoing in the United States (US) and Canada. An overview of these studies are presented in International Publication No. WO 2014/205229, the content of which is hereby incorporated by reference.

This invention will be better understood by reference to the Experimental Details which follow, but those skilled in the art will readily appreciate that the specific experiments detailed are only illustrative of the invention as described more fully in the claims which follow thereafter.

EXAMPLES

Example 1

A Phase II, Dose-finding, Randomized, Parallel-Group, Double-Blind, Placebo-Controlled Study, Evaluating the Safety and Efficacy of Pridopidine 45 mg, 67.5 mg, 90 mg, and 112.5 mg Twice-Daily versus Placebo for Symptomatic Treatment in Patients with Huntington's Disease ("PRIDE-HD")

The PRIDE-HD study assessed the efficacy of pridopidine 45 mg to 112.5 mg twice daily (bid) on motor impairment in patients with HD over at least 52 weeks of treatment using the Unified Huntington's Disease Rating Scale (UHDRS) Total Motor Score (TMS). The study also assessed the effect of at least 52 weeks of treatment with pridopidine 45 mg bid to 112.5 mg bid on the Modified Physical Performance Test (mPPT). The study also assessed the effect of at least 52 weeks of treatment with pridopidine 45 mg bid to 112.5 mg bid on UHDRS measures for total function capacity (TFC) and cognitive assessment battery (CAB). The study also compared data from all patients to those obtained in HD subpopulations. The study also (i) evaluated the safety and tolerability of a range of pridopidine doses in patients with HD during at least 52 weeks of treatment, (ii) explored the pharmacokinetics (PK) of pridopidine in the study population and (iii) investigated the relationship between exposure to pridopidine and outcome measures (e.g., clinical efficacy and toxicity parameters).

Study Design

General Design and Study Schema

This was a randomized, parallel-group, double blind, placebo controlled study that compared the efficacy and safety of pridopidine 45 mg, 67.5 mg, 90 mg, and 112.5 mg bid versus placebo in the treatment of motor impairment in HD.

The administration of pridopidine to patients is summarized in Table 2. The study procedures and assessments are summarized in Table 3. A detailed clinical procedure, including screening procedures and other procedures, is listed as Example 3 in U.S. Patent Application Publication No. US 2014/0378508 and International Publication No. WO 2014/205229, the content of which are hereby incorporated by reference.

Primary and Secondary Variables and Endpoints

The primary efficacy variable and endpoint for this study was change from baseline in the UHDRS TMS (defined as the sum of all UHDRS motor domains ratings) at Week 26 or Week 52. The primary measure of motor impairment is the UHDRS motor assessment section, which was administered by a trained examiner. The first part of the motor assessment consisted of five TMS subscores, provided below. The sum total of all the 31 items is referred to as the Total Motor Score (TMS). The secondary efficacy variable and endpoint was change from baseline in the mPPT at Week 26 or Week 52. The TMS scale includes measurement of dystonia.

Other Efficacy Variables and Endpoints

Other efficacy variables and endpoints for this study are as follows:

Global Functional Scales:
CIBIC-Plus global score as compared to baseline
Change from baseline in the PDS score
Change from baseline in UHDRS FA
CGIC as compared to baseline
Change from baseline in UHDRS TFC
Change from baseline in UHDRS IS
Global/Functional Scales:
Change from baseline in HD QoL
Change from baseline in Walk-12 scale
TMS Subscores:
Change from baseline in hand movement score (defined as the sum of UHDRS domains finger taps, pronate-supinate hands and luria [fist-hand-palm test])
Change from baseline in Gait and balance score (defined as the sum of UHDRS domains gait, tandem walking and retropulsion pull test)
Change from baseline in UHDRS mMS (defined as the sum of UHDRS domains dysarthria, tongue protrusion, finger taps, pronate-supinate hands, luria, rigidity, bradykinesia, gait, tandem walking, retropulsion pull test)
Change from baseline in UHDRS Chorea
Change from baseline in UHDRS Dystonia
Responders, defined as patients with UHDRS TMS change from baseline <0
Other Motor Assessments:
Change from baseline in Q Motor measurements including digitomotography (speeded index finger tapping), dysdiadochomotography (pronation/supination hand tapping), manumotography and choreomotography (grip force and chorea analysis) and pedomotography (speeded foot tapping)
Change from baseline in the TUG test
Cognitive/Psychiatric Assessments:
Change from baseline in HD-CAB brief: SDMT, Emotion Recognition, Trail Making Test, HVLT-R, Paced Tapping at 3 Hz, OTS.
Change from baseline in PBA-s Safety Variables and Endpoints Safety variables and endpoints include the following:
AEs throughout the study
Changes from baseline in QTcF and other ECG parameters throughout the study
Clinical safety laboratory (clinical chemistry, hematology, and urinalysis) throughout study
Changes from baseline C-SSRS throughout the study
Vital signs throughout the study Tolerability Variables and Endpoints Tolerability variables and endpoints include the following:
the number (%) of patients who failed to complete the study
the number (%) of patients who failed to complete the study due to AEs Pharmacokinetic Variables and Endpoints The primary PK measure was determination of plasma concentration of pridopidine. Concentrations were also incorporated into a pridopidine population PK model and individual exposure for the study patients (Cmax and AUC) was calculated.

Study Drugs and Dosage

Pridopidine (as pridopidine hydrochloride) was provided as a white hard gelatin capsule, size 2 containing 45 mg pridopidine and a white hard gelatin capsule, size 4 containing 22.5 mg pridopidine. Placebo was presented as white hard gelatin capsules matching the 22.5 mg or 45 mg pridopidine capsules but containing no active ingredient, only the excipients (silicified microcrystalline cellulose and magnesium stearate).

TABLE 2

Dose Administration (Capsules were Administered Twice Daily to Give the Total Daily Dose)

| | Titration Period | | | | Full Dose Period |
|---|---|---|---|---|---|
| Treatment | Week 1 | Week 2 | Week 3 | Week 4[a] | Weeks 4[b] to 52 |
| Pridopidine 45 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>1 × 22.5 mg Placebo<br>1 × 45 mg Placebo<br>(TDD = 90 mg) |

TABLE 2-continued

Dose Administration (Capsules were Administered Twice Daily to Give the Total Daily Dose)

| Treatment | Titration Period | | | | Full Dose Period |
|---|---|---|---|---|---|
| | Week 1 | Week 2 | Week 3 | Week 4[a] | Weeks 4[b] to 52 |
| Pridopidine 67.5 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>2 × 22.5 mg Placebo<br>(TDD = 90 mg) | 1 × 22.5 mg Pridopidine<br>1 × 45 mg Pridopidine<br>1 × 45 mg Placebo<br>(TDD = 135 mg) |
| Pridopidine 90 mg bid | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>1 × 22.5 mg Pridopidine<br>1 × 22.5 mg Placebo<br>(TDD = 135 mg) | 2 × 45 mg Pridopidine<br>1 × 22.5 mg Placebo<br>(TDD = 180 mg) |
| Pridopidine 112.5 mg bid | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>2 × 22.5 mg Pridopidine<br>(TDD = 180 mg) | 1 × 22.5 mg Pridopidine<br>2 × 45 mg Pridopidine<br>(TDD = 225 mg) |
| Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 1 × 22.5 mg Placebo<br>2 × 45 mg Placebo |

TDD = total daily dose;
[a]Excluding Day 28;
[b]Day 28 only

TABLE 3

Study Procedures and Assessments

| Procedures and Assessments | Screening | Titration Period | | | | First 26-Week Study Period | | | | | | Full Dose Treatment | | | | Second 26-week Study Period | | | | Follow Up |
|---|---|---|---|---|---|---|---|---|---|---|---|---|---|---|---|---|---|---|---|---|
| Visit | V0[a] | V1 | TC | V2 | TC | V3 | TC | V4[a] | V5[a] | V6[a] | V7[a] | V8[a] | V9[a] | TC | V10[a] | TC | TC | TC | V11[a] | V12[a] |
| Day | Maximum 12 weeks | 6±3 week | 14±3 week | | 20±3 week | 28±3 week | 35±3 week | 42±5 week | 56±5 week | 84±7 week | 112±7 week | 140±7 week | 182±7 week | 224±10 week | 273±7 week | 280-308 ±10 week | 315±10 week | 322-357 ±10 week | 364±7 week | 378±7 week |
| Procedures and assessments | BL Screening | 1 | 2 | | 3 | 4 | 5 | 6 | 8 | 12 | 16 | 20 | 26 | 32 | 39 | 40-44 | 45 | 46-51 | 52 | 54 |
| Abbreviated PBA-s | X | | | | | | | | | | | | | | | X[m] | X[m] | X[m] | | |
| CIBIS | | | | | | X | | | | X | | | X | | | | | | X | |
| CIBIC-Plus | | | | | | X | | | | X | | | X | | | | | | X | |
| PDS | X | X | | | | | | | | | | | | | | | | | | |
| CGI-S | X | X | | | | X | | | | X | | | X | | | | | | X | |
| CGI-C | | | | | | | | | | | | | | | | | | | | |
| HD-QoL | X | X | | | | X | | | | X | | | X | | | | | | X | |
| EQ5D5L | X | X | | | | X | | | | X | | | X | | | | | | X | |
| Walk-12 | X | X | | | | X | | | | X | | | X | | | | | | X | |
| Q-Motor assessments[b] | X | X[f] | | | | X[q] | | X[q] | | X[p] | X[q] | X[p] | X | | | | | | X[f] (trough) | X |
| TUG Test | X | X | | | | X | | X | X | X | X | X | X | | X | X | X | X | X | |
| Cognitive assessment battery[b] | X | X | | | | X | | X | X | X | X | X | X | X | X | X | X | X | X | X |
| Blood samples for drug concentration | | | X[p] | | X | X[q] | | X[q] | | X[p] | X[q] | X[p] | | | | | | | | |
| Adverse event inquiry | | X | X | | X | X | X | X | X | X | X | X | X | X | X | X | X | X | X | X |
| Concomitant medication inquiry | | X | X | | X | X | X | X | X | X | X | X | X | X | X | X | X | X | X | X |
| Benzodiazepines and antidepressants inquiry[†] | | | | | | | | | | | | X | | | X | X | X | X | X | |
| Alcohol/Illicit drug use inquiry | | | | | | | | | | | | X | | | X | X | X | X | X | |
| Review of tolerability to study drug prior to dose escalation (if applicable) | | X | | | X | | | | | | | | | | | | | | | |
| Dispense/collect study drug | | X | X | | | X | | X | | X | | X | X | | X | X | X | X | X[g] | X[g] |
| Review study compliance & adherence | | X | X | | | X | | | | X | | X | X | | X | X[v] | X[v] | X[v] | X | X |
| Study drug administration[w,%] | | | | | | | | | | | | | | | | → | | | | |

Table 3 Legend a The procedures and assessments for these visits (V0 and V4-12) may be performed over several days, as long as they are completed within the defined visit window.

b. Inclusion/exclusion criteria should be met at screening and reviewed on Day 0 before the patient is randomized.

c Electrolytes only.

d Serum pregnancy test at screening (with urine test if required for confirmation); urine pregnancy test at subsequent time points. An indeterminate reading for the serum pregnancy test should be checked twice (urine test) and the patient referred to a gynecologist if required.

e At screening, a single ECG was performed. When evidence of a prolonged QTcF interval at screening (defined as a QTcF interval of >450 msec) was detected then the ECG was repeated twice, and the mean of the 3 screening measurements was used to determine whether or not the patient is suitable for inclusion in the study.

f At the Baseline visit, the predose QTcF was determined by the average of 3 ECGs (within 10 to 20 minutes of one another), each in triplicate (in total 9 recordings).

A postdose ECG was performed in triplicate 1 to 2 hours after first dosing. PK samples were collected prior to and 1 to 2 hours after dose administration at the site.

When concomitant to ECG, PK samples are collected after the ECG recording.

g One ECG performed in triplicate prior and 1 to 2 hours post afternoon dose.

h ECG is optional on Week 8, unless required by local regulations. It is to be performed at the investigator's discretion where there are clinical circumstances that justify an additional ECG, eg, patients with a previous episode of hypokalemia without QT prolongation.

i On Week 52, a triplicate ECG and PK sample were collected before the last study (morning) dose.

j ECG is optional at the follow up visit, but should be performed for all patients with a previously observed cardiac concern and/or QTc change from baseline.

k Including CAG analysis, cytochrome P450 2D6 status, genetic long QT syndrome (assessed only in patients experiencing QT prolongation following study drug administration leading to study discontinuation), or any other genetic analyses related to pridopidine response or Huntington's disease.

l Evaluated in priority.

m The safety telephone calls included an abbreviated PBA-s (a subset of PBA questions on depressed mood, suicidal ideation, anxiety, irritability, loss of motivation and obsessive compulsive behaviors).

n Included digitomotography (speeded index finger tapping), dysdiadochomotography (pronation/supination hand tapping), manumotography and choreomotography (grip force and chorea analysis) and pedomotography (speeded foot tapping).

o Included SDMT, Emotion recognition, Trail Making Test A+B, HVLT-R; Paced Tapping Test and OTS.

p On Weeks 2, 12 and 20, PK samples were collected 1 to 2 hours post afternoon dose. When concomitant to ECG, PK samples were collected after the ECG recording.

q On Weeks 4, 6 and 16, PK samples were collected prior and 1 to 2 hours post afternoon dose. When concomitant to ECG, PK samples were collected after the ECG recording.

r On the last study day (week 52), the study drug administration will take place on site, after the pre-dose PK sample is obtained.

s At the follow up visit, 1 PK sample were collected. In case of SAE, an additional PK sampling should be aimed to be collected at the closest time to SAE. When concomitant to ECG, PK samples were collected after the ECG recording.

t This information were collected as part of concomitant medication inquiry.

u Collection only.

v Study adherence is reviewed during the TCs.

w Every patient received 3 capsules twice daily (bid), ie, 3 capsules in the morning and 3 capsules in the afternoon (7 to 10 hours after the morning dose), during the whole study period. Study drug was not administered at Early Termination visit. At on-site visits, the afternoon dose were taken at the site.

x Patients, who for safety or tolerability reasons have to stop study drug medication, were asked to continue in the study and follow the visit schedule as outlined without taking study drug.

Primary Efficacy Variable and Endpoint

The UHDRS comprises a broad assessment of features associated with HD (Huntington Study Group 1996). It is a research tool which has been developed to provide a uniform assessment of the clinical features and course of HD. The TMS component of UHDRS comprises 31 assessments from the 15 items of the UHDRS, with each assessment rated on a 5-point scale from 0 (normal) to 4 (maximally abnormal).

Secondary Efficacy Variable and Endpoint

The secondary efficacy variable and endpoint, the Modified Physical Performance Test (mPPT), quantifies the patient's performance in physical tasks (Brown 2000). It is a standardized 9-item test that measures the patient's performance on functional tasks. Assistive devices are permitted for the tasks that require a standing position (items 6 to 9). Both the speed and accuracy at which the patients complete the items were taken into account during scoring. The maximum score of the test is 36, with higher scores indicating better performance.

Other Efficacy Variables and Endpoints

Clinician Interview Based Impression of Change plus Caregiver Input

The CIBIC-Plus (version ADCS-CGIC) was developed, validated, and is commonly used in studies of anti-dementia drugs in Alzheimer's disease (Joffres 2000). An independent rater evaluated the patient's overall disease severity prior to the initiation of pridopidine or placebo. This assessment, known as the CIBIS, rates the patient on a 7-point Likert scale from extremely severe HD to no symptoms of HD.

Physical Disability Scale

The PDS was used during the study as a measure of disability. Patients were scored on a scale from 10 ("Fixed posture requiring total care—gastrotomy, catheterization") to 100 ("Normal; no disease evident") (Myers 1991).

UHDRS Functional Assessments or UHDRS Total Functional Assessment

The FA scale of the UHDRS assessed functionality in 25 tasks of daily living (e.g., "Could patient engage in gainful employment in his/her accustomed work?"). Each question was answered with 'yes' or 'no'.

Clinical Global Impression of Severity and Change

CGI-S was assessed at baseline and CGI-C was used at all subsequent time points to assess changes from baseline. The CGI-S scale was initially designed to assess treatment response in patients with mental disorders (Guy 1976) but is now used widely in a range of illnesses.

UHDRS Total Functional Capacity

The TFC scale of the UHDRS is a standardized scale used to assess 5 functional domains associated with disability shown below (occupation, finances, domestic chores (e.g.

laundry, washing dishes), activities of daily living, and care level). Total functional capacity score has a range of 0-13 and is a well-established endpoint for trials aiming disease progression. The Total functional capacity score has been developed and deployed by the Huntington Study Group (HSG, 1996) in multiple trials over 2 decades and is accepted by regulators.

Functional Capacity:
Occupation: 0=unable, 1=marginal work only, 2=reduced capacity for usual job, 3=normal.
Finances: 0=unable, 1=major assistance, 2=slight assistance, 3=normal.
Domestic Chores: 0=unable, 1=impaired, 2=normal.
ADL: 0=total care, 1=gross tasks only, 2=minimal impairment, 3=normal.
Care level: 0=fill time skill nursing, 1=home or chronic care, 2=home.

UHDRS Independence Scale

The independence scale of the UHDRS is a rating scale where the patient's degree of independence was given in percentage, from 10% (tube fed, total bed care) to 100% (no special care needed).

Global/Functional Scales
Huntington's Disease Quality of Life

The HD-QoL is a standardized instrument for measuring health-related quality of life. (Hocaoglu 2012). It is a validated disease-specific measure designed for HD, and can provide a summary score of overall health-related quality of life, as well as scores on several discrete scales.

Total Motor Score Subscores
UHDRS Hand Movement Score or UHDRS TMS Hand Movement Score The hand movement score is defined as the sum of UHDRS domains finger taps, pronate-supinate hands and luria (fist-hand-palm test).

UHDRS Gait and Balance Score or UHDRS TMS Gait and Balance Score

The gait and balance score is defined as the sum of UHDRS domains gait, tandem walking and retropulsion pull test.

UHDRS Modified Motor Scale or UHDRS TMS Modified Motor Scale

The UHDRS-mMS is defined as the sum of following domains from UHDRS-TMS: dysarthria, tongue protrusion, finger taps, pronate-supinate hands, luria, rigidity, bradykinesia, gait, tandem walking, and retropulsion pull test.

UHDRS Chorea or UHDRS TMS Chorea

In the UHDRS, maximal chorea was scored from 0 (absent) to 4 (marked/prolonged) on each of the following items: face, mouth, trunk, right upper extremity, left upper extremity, right lower extremity, and left lower extremity. Maximal chorea is the sum of all scores.

UHDRS Dystonia or UHDRS TMS Dystonia

In the UHDRS, maximal dystonia was scored from 0 (absent) to 4 (marked/prolonged) on each of the following items: trunk, right upper extremity, left upper extremity, right lower extremity, and left lower extremity. Maximal dystonia is the sum of all scores.

TMS Proportion of Responders

The percentage of responders, defined as patients with UHDRS-TMS change from baseline≤0 at Week 26.

Other Motor Assessments
Multiple Sclerosis Walking Scale

The Multiple Sclerosis Walking Scale (MSWS-12) was adapted to become a generic measure of walking and mobility and renamed the Walk-12.

European Quality of Life-3 Dimensions (3 Levels)

The EQSD 3 level version (EQSD-3L) was introduced in 1990 (EuroQol Group 1990). It essentially consists of the EQSD descriptive system and the EQ visual analogue scale (EQ VAS). The EQSD-3L descriptive system comprises the following 5 dimensions: mobility, self-care, usual activities, pain/discomfort and anxiety/depression.

Quantitative Motor (Q-motor) Assessments

Motor deficits can be objectively assessed using different Q-Motor assessments. All Q-Motor assessments are based on the application of precalibrated and temperature controlled force transducers and 3-dimensional position sensors with very high sensitivity and test-retest reliability across sessions and sites in a multicenter clinical study. Q-Motor measures thus aim to reduce the limited sensitivity of categorical clinical rating scales, the intra- and inter-rater variability, and placebo effects observed in scales such as UHDRS-TMS. In addition, Q-Motor assessments allow for the objective monitoring of unintended motor side-effects in clinical studies. Thus, Q-Motor is an objective, reliable, and sensitive measure of motor function that is free of rater bias and limits placebo effect influence. FIG. 10 shows the Q-motor tap measurements for a normal patient, a patient with mild defects and a patient with severe defects. In Track-HD, the largest natural history study of pre-manifest and early stage HD Q-motor tapping deficits correlated with clinical scores as well as regional brain atrophy (FIGS. 11a, 11b, 12 and Bechtel 2010).

Digitomography (Speeded Index Finger Tapping)

The patient places their hand on a hand rest with their index finger positioned above a force-transducer. Recordings start after practice runs. The patient is instructed to finger tap as fast as possible between 2 auditory cues. The beginning of a tap is defined as a rise of the force by 0.05 N above maximal baseline level. The tap ends when it drops to 0.05 N before the maximal baseline level is reached again. The duration and variability of tap durations (TD), inter onset intervals (IOI), inter peak intervals (IPI), and inter tap intervals (ITI) are the exploratory outcome measures for speeded tapping. In addition, variability of peak tapping forces (TF) is calculated as coefficient of variation, and the tapping frequency (Freq), i.e., the number of taps between the onsets of the first and the last tap divided by the time in between, is determined. Five trials of 10 seconds duration are performed with each hand.

Dysdiadochomotography (Pronation/Supination Hand Tapping)

This task assessed the regularity of hand taps performed when alternating between the palm and dorsal surface of the hand performing a repetitive pronation/supination movement. The force and duration of the hand taps are recorded similarly to the speeded tapping task. A tone cues the start and end of an assessment. Five trials of 10 seconds duration are performed with each hand.

UHDRS Pronation/Supination Assessment

An assessment of the ability to rotate the forearm and hand such that the palm is down (pronation) and to rotate the forearm and hand such that the palm is up (supination) on both sides of the body.

Manumotography and Choreomotography (Grip Force and Chorea Analysis)

This task assessed the coordination of isometric grip forces in the precision grip between the thumb and index finger. Grip forces are assessed during grip initiation, object transport, and in a static holding phase. Patients are instructed to grasp and lift a device equipped with a force transducer and 3-dimensional position sensor in the precision grip between thumb and index finger and hold it stable adjacent to a marker 10-cm high. Grip forces and 3-dimensional position and orientation of the object are recorded. Mean isometric grip forces and grip force variability in the static phase (expressed as coefficient of variation=standard deviation [SD]/mean×100) (GFV-C) are calculated during a 15-second period starting 8 seconds after the first cueing tone. Five trials of 20 seconds duration are performed with each hand. Chorea is assessed calculating a "position-index" and "orientation-index". Start and end of assessment are signaled by a cueing tone.

Pedomotography (Speeded Foot Tapping)

The patient places a foot on the foot device such that the ball of the foot is positioned above a force-transducer. Recordings start after practice runs. The patient is instructed to tap with the foot as fast as possible between 2 auditory cues. The beginning of a tap is defined as a rise of the force by 0.05 N above maximal baseline level. The tap ends when it dropped to 0.05 N before the maximal baseline level is reached again. The duration and variability of TD, IOI, IPI, and ITI are the exploratory outcome measures for speeded tapping. In addition, variability of peak TF is calculated as coefficient of variation, and the tapping Freq, i.e., the number of taps between the onsets of the first and the last tap divided by the time in between, is determined. Five trials of 10 seconds duration are performed with each foot.

Timed Up and Go Test

The TUG is a simple test used to assess a person's mobility and requires both static and dynamic balance. It uses the time that a person takes to rise from a chair, walk 3 meters, turn around, walk back to the chair, and sit down. During the test, the person is expected to wear their regular footwear and use any mobility aids that they would normally require. The TUG is used frequently in the elderly population, as it is easy to administer and can generally be completed by the majority of older adults. The test is quick, requires no special equipment or training, and is easily included as part of the routine medical examination (Podsiadlo 1991). The use of the TUG test in conjunction with UHDRS has been recommended for clinical studies of HD (Rao 2009).

Cognitive Assessment Battery (CAB)

The following six sections describe the tests that are part of the CAB brief.

1. Symbol Digit Modalities Test

The SDMT is a paper-and-pencil test of psychomotor speed and working memory.

2. Emotion Recognition

Emotion recognition of facial expressions of emotions is examined using computerized presentations of photographs depicting 6 basic emotions or a neutral expression.

3. Trail Making Tests A and B

Visual attention and task switching are assessed using the Trail Making test, which consists of 25 circles on a standard sheet of paper. For Trail A, participants are required to connect, as quickly as possible, circles containing numbers in ascending numerical order. For Trail B, participants are to connect, as quickly as possible, circles containing numbers and letters, alternating between numbers and letters in ascending order (e.g., 1, A, 2, B, 3, C, etc.).

4. Hopkins Verbal Learning Test, Revised

The HVLT-R offers a brief assessment of verbal learning and memory (recognition and recall).

5. Paced Tapping test

Psychomotor function is assessed in a Paced Tapping test. Participants tap on left and right mouse buttons, alternating between thumbs, at 3.0 Hz. They first listen to a tone presented at the desired tapping rate, and then begin tapping to the tone. After 11 taps with the tone, the repetition of the tone is discontinued, and participants attempt to continue tapping at the same rate until the end of the trial (31 taps later).

6. One Touch Stockings of Cambridge (OTS)

OTS is a spatial planning task which gives a measure of frontal lobe function. OTS is a variant of the Stockings of Cambridge task, and places greater demands on working memory as the participant has to visualize the solution.

7. Problem Behaviors Assessment-Short Form (PBA-s)

Because of the prominence of psychiatric symptoms in HD, it is recommended that the PBA-s form be used in all HD studies with any need for behavioral assessment as a comprehensive screen for the most common psychiatric symptoms in HD. (Craufurd 2001, Kingma 2008).

Assessment of Safety

In this Example, safety was assessed by qualified study staff by evaluating the following: reported AEs, clinical laboratory test results, vital signs measurements, ECG findings, physical and neurological examination findings (including body weight), and concomitant medication usage.

Clinical Laboratory Tests

Clinical laboratory tests (serum chemistry including electrolytes, hematology and urinalysis) were performed as listed below.

The following serum chemistry tests were performed: calcium; phosphorus; sodium; magnesium; potassium; chloride; bicarbonate or carbon dioxide; glucose; blood urea nitrogen; creatinine; cholesterol; uric acid; ALT; AST (aspartate aminotransferase); lactate dehydrogenase; gamma-glutamyl transpeptidase (GGT); alkaline phosphatase; creatine phosphokinase (in case of elevated creatine phosphokinase, the MB fraction should be measured); total protein, albumin; total bilirubin; direct bilirubin; indirect bilirubin; and prolactin. The following hematology tests were performed: Hemoglobin; hematocrit; red blood cell (RBC) count; platelet count; white blood cell (WBC) count and differential count; absolute neutrophil count; absolute lymphocyte count; absolute eosinophil count; absolute monocytes count; absolute basophil count; and absolute atypical lymphocyte count. Urinalysis includes testing for the following: Protein; glucose; ketones; blood (hemoglobin); pH; specific gravity; leukocyte esterase; microscopic; bacteria; RBCs; WBCs; casts; and crystals.

Vital Signs

Vital signs, including pulse, blood pressure, and body temperature were measured.

Assessment of Pharmacokinetics and Pharmacogenomics

The primary PK measure is a determination of plasma concentration of pridopidine. Concentrations were also incorporated into a pridopidine population PK model and individual exposure for the study patients (Cmax and AUC) was calculated.

Blood Sampling and Handling

Blood samples (4 mL each) were collected for the determination of plasma concentrations via venipuncture or indwelling catheter in the morning before study drug administration at the following visits:

Titration Period: day 0 (baseline)—prior and 1 to 2 hours post first dose and day 14—1 to 2 hours post afternoon dose. Full Treatment Dose Period: day 28—pre afternoon dose and 1 to 2 hours post afternoon dose, day 42—pre afternoon dose and 1 to 2 hours post afternoon dose, day 84—1 to 2 hours post afternoon dose, day 112—pre afternoon dose and 1 to 2 hours post afternoon dose, day 140—1 to 2 hours post afternoon dose, day 182—prior to morning dose, and follow-up visit.

Analysis of Samples

Samples were analyzed using an appropriate validated method for pridopidine and its main metabolite TV-45065 (previously called ACR30). The lower limits of quantification for pridopidine and TV-45065 in plasma are approximately 1.6 to 1.8 ng/mL and 1.5 to 1.9 ng/mL, respectively.

Pharmacogenomic Variables

A blood sample (10 mL) was collected in 2 dipotassium ethylenediaminetetraacetic acid (K2EDTA) plastic tubes at the screening visit for genetic analyses. Analyses include CAG repeats, CYP2D6 status, and genetic long QT syndrome, or any other genetic analyses related to pridopidine response or HD.

Primary Efficacy Analysis

The change from baseline in UHDRS-TMS was analyzed using a Repeated Measures model (SAS® MIXED procedure with REPEATED sub-command). The model includes the following fixed effects: categorical week in study by treatment interaction, center, neuroleptic use or no use, and baseline UHDRS-TMS score. The unstructured covariance matrix for repeated observations within patients was used. In case that the model does not converge, the Maximum-Likelihood (ML) estimation method is used instead of the default Restricted ML (REML). If the model still does not converge then a simpler covariance structures with less parameters is used, according to the following order: Heterogeneous Autoregressive(1) [ARH(1)], Heterogeneous Compound Symmetry (CSH), Autoregressive(1) [AR(1)], and Compound Symmetry (CS). The estimated means at the Week 26 visit of the change from baseline in UHDRS-TMS was compared between the active treatment arms) and the placebo arm.

Sensitivity Analysis

A sensitivity analysis to evaluate if the observed effect in UHDRS-TMS is driven by the Chorea UHDRS-TMS sub-score, the Dystonia UHDRS-TMS sub-score, or the Involuntary Movements (Chorea+Dystonia) UHDRS-TMS sub-score was performed as follows: Three variables were calculated: (1) The change from baseline to Week 26 and Week 52 in the sum of the UHDRS-TMS items except the Chorea items, (2) The change from baseline to Week 26 and Week 52 in the sum of the UHDRS-TMS items except the Dystonia items, and (3) The change from baseline to Week 26 and Week 52 in the sum of the UHDRS-TMS items except the Chorea and Dystonia items. These variables were analyzed in the same way as the primary efficacy endpoint except that the variable evaluation at baseline were included in the model instead of baseline UHDRS-TMS.

Pharmacokinetic Analysis

Plasma concentration data on pridopidine and the main metabolite TV-45065 are presented by descriptive statistics by dose of pridopidine and also by CYP2D6 metabolizer status. Concentrations are also incorporated into a pridopidine population PK model and individual exposure for the study patients ($C_{max}$ and AUC) are calculated.

Patient Disposition by Treatment Group

| Analysis group, n (%) | Placebo | Pridopidine 45 mg bid | 67.5 mg bid | 90 mg bid | 112.5 mg bid | All | Total |
|---|---|---|---|---|---|---|---|
| Screened | | | | | | | 492 |
| Screened, not in ITT population | | | | | | | 84 |
| Death | | | | | | | 0 |
| Adverse event | | | | | | | 0 |
| Withdrawal by subject | | | | | | | 11 |
| Inclusion criteria not met | | | | | | | 20 |
| Exclusion criteria met | | | | | | | 46 |
| Lost to follow-up | | | | | | | 0 |
| Other | | | | | | | 7 |
| ITT population | 82 (100) | 81 (100) | 82 (100) | 81 (100) | 82 (100) | 326 (100) | 408 (100) |
| ITT population, not treated | 0 | 0 | 0 | 0 | 0 | 0 | 0 |
| Safety population (SP) | 82 (100) | 81 (100) | 82 (100) | 81 (100) | 82 (100) | 326 (100) | 408 (100) |
| PK population (PK) | 0 | 0 | 0 | 0 | 0 | 0 | 0 |
| Full analysis set (FAS) | 81 (99) | 75 (93) | 79 (96) | 81 (100) | 81 (99) | 316 (97) | 397 (97) |
| Full analysis set on study drug (FASOD) | 81 (99) | 75 (93) | 79 (96) | 81 (100) | 81 (99) | 316 (97) | 397 (97) |
| Complete 26 weeks of treatment (CO) | 70 (85) | 59 (73) | 65 (79) | 67 (83) | 62 (76) | 253 (78) | 323* (79) |
| Discontinued treatment during 1st period | 12 (15) | 22 (27) | 17 (21) | 14 (17) | 20 (24) | 73 (22) | 85* (21) |
| Death | 0 | 0 | 0 | 0 | 0 | 0 | 0 |
| Adverse event | 5 (6) | 6 (7) | 11 (13) | 11 (14) | 14 (17) | 42 (13) | 47 (12) |
| Withdrawal by subject | 3 (4) | 9 (11) | 3 (4) | 0 | 3 (4) | 15 (5) | 18 (4) |
| Non-compliance | 2 (2) | 1 (1) | 1 (1) | 0 | 0 | 2 (<1) | 4 (<1) |
| Protocol violation | 1 (1) | 1 (1) | 1 (1) | 1 (1) | 0 | 3 (<1) | 4 (<1) |
| Pregnancy | 0 | 0 | 0 | 0 | 0 | 0 | 0 |
| Lost to follow-up | 0 | 0 | 0 | 0 | 0 | 0 | 0 |
| Lack of efficacy | 0 | 0 | 1 (1) | 0 | 0 | 1 (<1) | 1 (<1) |
| Other | 1 (1) | 5 (6) | 0 | 2 (2) | 3 (4) | 10 (3) | 11 (3) |
| Discontinued treatment during 1st period but continue to FU | 1 (1) | 0 | 2 (2) | 2 (2) | 2 (2) | 6 (2) | 7 (2) |
| Complete 26 weeks of study | 70 (85) | 61 (75) | 66 (80) | 67 (83) | 66 (80) | 260 (80) | 330 (81) |
| Signed protocol amendment 4 | 59 (72) | 55 (68) | 60 (73) | 62 (77) | 57 (70) | 234 (72) | 293 (72) |
| Entered 2nd period | 57 (70) | 49 (60) | 54 (66) | 56 (69) | 46 (56) | 205 (63) | 262 (64) |
| Started treatment for 2nd period | 57 (70) | 49 (60) | 52 (63) | 56 (69) | 46 (56) | 203 (62) | 260 (64) |
| ITT population for the 52 Weeks Analysis (ITT2) | 82 (100) | 81 (100) | 82 (100) | 81 (100) | 82 (100) | 326 (100) | 408 (100) |
| Safety population for the 52 Weeks Analysis (5P2) | 82 (100) | 81 (100) | 82 (100) | 81 (100) | 82 (100) | 326 (100) | 408 (100) |
| PK population for the 52 Weeks Analysis (PK2) | 0 | 0 | 0 | 0 | 0 | 0 | 0 |
| Full analysis set for the 52 Weeks Analysis (FAS2) | 81 (99) | 75 (93) | 79 (96) | 81 (100) | 81 (99) | 316 (97) | 397 (97) |
| Complete 52 weeks of treatment | 52 (63) | 43 (53) | 44 (54) | 53 (65) | 44 (54) | 184 (56) | 236 (58) |
| Discontinued treatment during 2nd period | 5 (6) | 6 (7) | 8 (10) | 3 (4) | 2 (2) | 19 (6) | 24 (6) |

Patient Disposition by Treatment Group

| Analysis group, n (%) | Placebo | Pridopidine | | | | | Total |
| --- | --- | --- | --- | --- | --- | --- | --- |
| | | 45 mg bid | 67.5 mg bid | 90 mg bid | 112.5 mg bid | All | |
| Death | 0 | 0 | 0 | 1 (1) | 0 | 1 (<1) | 1 (<1) |
| Adverse event | 1 (1) | 4 (5) | 5 (6) | 0 | 1 (1) | 10 (3) | 11 (3) |
| Withdrawal by subject | 2 (2) | 1 (1) | 2 (2) | 0 | 0 | 3 (<1) | 5 (1) |
| Non-compliance | 1 (1) | 0 | 0 | 0 | 0 | 0 | 1 (<1) |
| Protocol violation | 0 | 0 | 0 | 0 | 0 | 0 | 0 |
| Pregnancy | 0 | 0 | 0 | 0 | 0 | 0 | 0 |
| Lost to follow-up | 0 | 0 | 0 | 0 | 0 | 0 | 0 |
| Lack of efficacy | 1 (1) | 0 | 0 | 1 (1) | 1 (1) | 2 (<1) | 3 (<1) |
| Other | 0 | 1 (1) | 1 (1) | 1 (1) | 0 | 3 (<1) | 3 (<1) |
| Discontinued treatment during 2nd period but continue to FU | 0 | 1 (1) | 2 (2) | 0 | 1 (1) | 4 (1) | 4 (<1) |
| Complete 52 weeks of study | 52 (63) | 43 (53) | 46 (56) | 52 (64) | 44 (54) | 185 (57) | 237 (58) |

Stages of Huntington's Disease

Many clinicians and diagnosticians adopt the Shoulson and Fahn rating scale, based on TFC scores, to follow progression of HD. This rating scale groups total TFC scores into five stages of disease, with lower stages indicating more intact functioning. Table 4, below, provides the TFC scores, average years from diagnosis and broad guidelines for typical care level for each stage of disease. (Johnson 2014.)

TABLE 4

| Stage | TFC score | Years since motor diagnosis | Typical abilities and care level |
| --- | --- | --- | --- |
| 1 | 11-13 | 0-8 | Able to work at least part time, may require slight assistance in one of finances, domestic chores or ADL basic functions |
| 2 | 7-10 | 3-13 | Unable to work, requires some assistance in some basic functions |
| 3 | 3-6 | 5-16 | Unable to work, requires major assistance in most basic functions |
| 4 | 1-2 | 9-21 | Requires major assistance in all basic functions and although comprehension may be intact requires assistance to act. |
| 5 | 0 | 11-26 | Requires major assistance in all basic functions and full time nursing care |

Results

The results of this example are shown in FIGS. 1-18.

Overview of Preliminary Analysis of Functional, Exploratory Endpoints and Safety:

Endpoints not dependent on rater bias were less prone to placebo effect, such as the Q-motor assessment. The signals detected suggest biological effects of pridopidine. Total Functional Capacity (TFC) showed trends favoring pridopidine after 26 weeks of treatment. There was no major safety findings despite high doses.

Preliminary Results on TFC Scores—Considerations

Expected deterioration of about 0.5 points were seen in the placebo group at 6 months. Historical data indicates that TFC deteriorates about 1 point per year in patients with Huntington's disease. TFC starts showing separation from placebo at week 12 to 20 and separation becomes a strong trend at week 26. The TFC data supports a finding that pridopidine causes a delay of progression of functional decline.

Without wishing to be bound to this theory, the treatment effects shown in the figures were more pronounced when treating early patients (including stages 1 and 2), especially early stages with BL TFC greater than or equal to 7, and even more so in stage 1 (BL TFC=11-13). Without wishing to be bound to this theory this is particularly true for TFC finances and ADL, dystonia, involuntary movements (dystonia and chorea). A patient affected with HD with a baseline TFC score of 11-13 is considered to be a stage 1 HD patient.

Potential Placebo Effect Contributors in this Example

The following items may account for the placebo effect seen in this example: Rater bias, a lack of hope in Huntington's disease, together with a high expectation for an effective treatment and a desire to get better from patients, overall positive data with pridopidine treatment causes high expectations, patients have an 80% chance to receive active treatment, a high number of pills may cause expectancy, protocol changes during the study, and the number of assessments per visit.

Dystonia

The results shown in the figures, especially FIGS. 6-7, 8 (i, j, k, l), 9 (i, j, k, m) and 15-18, demonstrate that patients undergoing pridopidine therapy experienced an improved dystonia score in comparison to those patients receiving a placebo. For example, FIGS. 15-18 show anti-dystonia effect especially in patients who have a degree of dystonia (GE 4) at baseline with doses 45 and 67.5 mg pridopidine bid showing numerical improvement.

By carefully selecting the patients (e.g. assessing functional capacity at baseline) and selecting patients with a TFC of 11-13 at baseline, doses of pridopidine, in particular at 45 and 90 mg bid, show a treatment effect (FIGS. 8j & l).

The dystonia treated in FIGS. 6-7, 8 (i, j, k), 9 (i, j, k, m) and 15-18 is representative of treating dystonia as described in this application. The effects of pridopidine on non-HD dystonias is expected to be similar to its benefit on HD dystonia due to shared areas of direct pathological involvement (e.g. striatum) and/or impaired connectivity between these brain regions (striatum, cerebellum, etc.), plus the known complex effects of pridopidine on multiple targets in the brain, including the striatum and cerebellum.

The total dystonia treatment exemplified in this application is representative of treatment of, inter alia, the following types of dystonia: early onset generalized dystonia (DYT1 and non-DYT1 dystonias), early onset and late onset dystonias, focal, segmental, multifocal, hemi- or generalized dystonias, Musician's dystonias, Dopa-responsive dystonias, Myoclonus dystonias, Paroxysmal dystonias and dyskinesias, X-linked dystonia-parkinsonisms, Rapid-onset dystonia-parkinsonisms, Primary dystonias, Secondary dystonias (including Huntington's dystonia), and Psychogenic dystonias.

Discussion

TMS and Motor Endpoints:

Motor effects were statistically significant in Huntington's disease stage 1 subpopulations. For example, statistically significant changes were seen in the HD Stage 1 patient subgroups for Total TMS, Involuntary movements (Dystonia, Chorea), Ambulation (TMS Gait and Balance, Time Up and Go, Walk-12).

In early HD there was a statistically significant effect on TMS at weeks 26 (FIG. 8b) and 52 (FIG. 8d) driven by a lower placebo effect. Involuntary Movements (chorea and dystonia) as measured by TMS improved in HD1 patients at 26 weeks (FIG. 8n). The effect persisted at 52 weeks as well (FIG. 8p).

Example 2

Rodent Models of Dystonia

Liang, et al. (2014) mouse model for primary generalized dystonia.

Overt dystonic symptoms were observed in mice with either a conditional deletion of the complete torsin-1A (Tor1a) gene, or a three-nucleotide Tor1a deletion that is associated with DYT1 in humans.

Multiple cellular effects were observed in these mice, including mislocalization of associated proteins, alterations in protein turnover, and age-restricted, region-specific neurodegeneration.

Liang's model highlights how subtle and selective dystonia associated neurodegeneration can occur in specific cell populations during certain stages of CNS development, with no further neurodegeneration occurring thereafter.

Example 3

Treatment of Patients Afflicted with Dystonia with Pridopidine Rationale

There is evidence for striatal involvement and abnormal synaptic connectivity in the pathophysiology of most forms of primary and secondary dystonia. In patients with DYT-1 dystonia, Positron Emission Tomography (PET) and Diffusion Tensor Imaging (DTI) MRI studies suggest abnormalities of basal ganglia, thalamic, cortical, and/or cerebellar regions (e.g. metabolism) or circuits.

Pridopidine has complex pharmacological effects on multiple targets found in the basal ganglia and cerebellum. Without wishing to be bound to theory, the potential synaptic actions of pridopidine may be consistent with a therapeutic effect in dystonia, including promoting synapse formation.

In clinical trials conducted in HD patients (HART, MermaiHD, and PRIDE-HD), those receiving pridopidine often had better outcomes on specific measures of dystonia. In PRIDE-HD, responder analysis in patients reporting some measure of dystonia further supports a benefit of pridopidine in dystonia.

Example 4

Assessment of Efficacy of Pridopidine for Treating Patients Afflicted with Dystonia Periodic (e.g., daily or twice daily) oral administration of pridopidine is effective in treating human patients afflicted with dystonia. Periodic (e.g., daily or twice daily) oral administration of pridopidine is effective to treat the subject suffering from dystonia. The administration of pridopidine is effective to reduce dystonia in afflicted patients.

A pridopidine composition as described herein is administered orally to a subject suffering from dystonia. The administration of the composition is effective to treat the subject suffering from dystonia. The administration of the composition is effective to reduce dystonia in afflicted patients.

Example 5

Assessment of Efficacy of Pridopidine for Treating DYT1 and other Primary Genetic Generalized Forms of Dystonia Objective To conduct a randomized, double-blind, placebo-controlled study to assess the change in the severity of dystonia (using the Burke-Fahn-Marsden Dystonia (BFMD) Rating Scale or the Unified Dystonia Rating Scale (UDRS)) in a population of patients with DYT1 and other primary genetic forms of dystonia after 26 weeks of treatment compared to baseline in patients on pridopidine versus a placebo.

Method

This study compares a cohort that receives pridopidine 45 mg b.i.d., 90 mg b.i.d., and placebo b.i.d. for a period of 26 weeks. The study population consists of those with DYT1 and other primary genetic forms of dystonia, as confirmed by genetic testing. The study's other inclusion criteria are patients with a BFMD score greater than 6, male or female patients, patients of any race or ethnicity, and patients with the ability to provide informed consent.

Burke-Fahn-Marsden Dystonia Rating Scale (BFMDRS) Rating Scale evaluates nine body parts (eyes, mouth, speech, swallowing, neck, trunk, right arm, right leg, left arm, and left leg) by rating the severity factor and provoking factors for each part on a 5 point scale of 0 (no dystonia) to 4 (indicating the presence of dystonia at rest). The dystonia scores of the eyes, mouth and neck are assigned a weighting factor of 0.5, while the other 6 parts are assigned a weighting factor of 1.0. The score of each part is obtained by multiplying the provoking factor by the severity factor and the weighting factor, and then summing the scores of each part. The maximum score possible is 120. A higher score indicates more severe dystonia.

The UDRS Rating Scale evaluates 14 body parts (eyes and upper face, lower face, jaw and tongue, larynx, neck, trunk, right shoulder/proximal arm, left shoulder/proximal arm, right distal arm/hand, left distal arm/hand, right proximal leg, left proximal leg, right distal leg/foot, and left distal leg/foot) by rating the severity and duration factors for each part. The severity factor for each part is rated using a 5-point scale, ranging from 0 (no dystonia) to 4 (severe dystonia). The duration factor is rating on a 5 point scale ranging from 0 (at rest/action) to 4 (submaximal/maximal). The total score is the sum of each domain (part), with the maximum being 112. A higher score indicates more severe dystonia.

The primary outcome is the change in the severity of dystonia (using the Burke-Fahn-Marsden Dystonia Rating Scale or the Unified Dystonia Rating Scale) after 26 weeks of treatment compared to baseline in patients on pridopidine vs. placebo.

The secondary outcomes are Clinical Global Impression (CGI), Patient Global Assessment, Visual Analogue Score for pain, Patient Evaluation of Global Response, Burke-Fahn-Marsden Disability Scale (BFMDS), Health Related quality of life (EQ-5D, SF-36), safety and tolerability of pridopidine including Beck Depression Inventory, cognitive impairment (e.g. Montreal Cognitive Assessment, Mattis Dementia Rating Scale, or Mini-Mental State Examination, and differences in number of treatment responders (at least 25% improvement in BFMDRS).

The study does not enroll patients with segmental and focal dystonias. Other exclusion criteria include: patients with primary genetic complex forms of dystonia with clear syndromic features, patients with secondary dystonias, patients whose conditions are judged by their physician to be too severe to participate in the study, patients with active seizure disorder, patients with comorbidities such as Parkinson's disease, schizophrenia, moderate to severe depression, cognitive impairment, dementia, renal failure, or other severe comorbidities, patients who are pregnant, lactating, probably pregnant, and patients who want to become pregnant, patients who cannot agree to contraception, patients who have participated in other trials within 12 weeks before consent, patients who are presently participating in other clinical trials, patients with the inability to follow the study protocol, and patients who are judged by their physician to be a poor candidate for this study.

The standard of care therapy may include oral medications, injectable medications, deep brain stimulation or intrathecal baclofen.

Treatment with pridopidine as described in this example is found to improve the severity of dystonia as measured by the primary endpoint. Treatment with pridopidine as described in this example is also found to improve the secondary outcomes discussed in this example.

Example 6

Pre-Clinical Anti-dystonia Drug Screening

Overview:

In the current pre-clinical study, 2 compounds (the test compound, pridopidine, and a positive control) are tested in 3 different mouse models known for testing dystonia: Bay K 8644-induced dystonia; Tottering mouse mutants (with induction by caffeine); and kainite-induced dystonia.

For each model, 4 doses of the test compound (plus dosage vehicle) are given, and 1 dose of the positive control (plus dosage vehicle). 8 mice will receive each dose. The tottering mouse mutants model is a crossover design and the tests in the Bay K 8644-induced dystonia and kainite-induced dystonia models are grouped independently.

The drug or vehicle is administered before the induction of dystonia. After dystonia is induced, each mouse is observed for 30 seconds every 10 minutes for 60 minutes by a rater who has been blinded to treatment and dose. Raters are trained extensively using an established rating scale with established inter-rater reliability of ≥90%. A total score is calculated for the entire 60 minutes session, with scores also recorded as a function of time over a regular interval for the 60 minute period.

Example 7

Effects of Pridopidine on L-DOPA-induced Dystonia

Pridopidine produced a significant and dose-dependent reduction in levels of L-DOPA-induced dystonia evoked by LDh. Examining the whole 6 h time-course revealed a significant effect of combination treatment ($F_{(3, 28)}=7.017$, $P=0.0012$) but not time ($F_{(5, 140)}=0$, $P>0.9999$) or the interaction of treatment and time ($F_{(15, 140)}=0.9735$, $P=0.4863$) on levels of dystonia (2-way, RM-ANOVA, FIG. 19A). Comparing to LDh-vehicle treatment revealed a significant decrease in dystonia during the first hour (20 and 30 mg/kg) and second and third hours (30 mg/kg) after start of observation in response to LDh when combined with pridopidine, with median levels remaining between moderate and marked (20 mg/kg) or mild to moderate (30 mg/kg) (all $P<0.05$). Assessing levels of dystonia cumulated over the 0-2 h period revealed a significant effect of pridopidine combination treatment (0-2 h; Friedman Statistic (FS) =11.88, $P=0.0078$, FIG. 19B) on levels of dystonia evoked by LDh administration. Median levels of dystonia in animals treated with LDh combined with high-dose pridopidine (30 mg/kg) were reduced (by 72%) compared to that seen following LDh-vehicle such that median levels of dyskinesia were below mild (non-disabling) ($P<0.01$).

REFERENCES CITED

Albanese, A. et al. A systematic review on the diagnosis and treatment of primary (idiopathic) dystonia and dystonia plus syndromes: report of an EFNS/MDS-ES Task Force. (2006). Eur J of Neurology, 13: 433-444.

Albanese, A., Bhatia, K., Bressman, S. B., DeLong, M. R., Fahn, S., Fung, V. S. C., Hallett, M., Jankovic, J., Jinnah, H A, Klein, C., Lang, A E, Mink, J W, Teller, J. K., Phenomenology and classification of dystonia: a consensus update. (2013) Movement Disorders: 28(7), 863-873. (Albanese 2013a)

Albanese, A., Del Sorbo, F., Comella, C., Jinnah, H. A., Mink, J W., Post, B., Vidailhet, M., Volkmann, J., Warner, T T., Leentjens, A F G., Martinez-Martin, P, Stebbins, G T., Goetz, C T, and Schrag, A. Dystonia rating scales: critique and recommendations. (2013) Mov Disord. 28(7): 874-883. (Albanese 2013b)

Bechtel, N. et al., Tapping linked to function and structure in premanifest and symptomatic Huntington disease. (2010) Neurology. 75(24):2150-60.

Bowie C R, Harvey P D. Administration and interpretation of the Trail Making Test. (2006) Nat Protoc. 1(5):2277-81.

Brown M, Sinacore D R, Binder E F, Kohrt W M. Physical and performance measures for the identification of mild to moderate frailty. J Gerontol A Biol Sci Med Sci. (2000) June; 55A(6):M350-5.

Coenzyme Q10 in Huntington's Disease (HD) (2CARE), ClinicalTrials.gov Identifier: NCT00608881, clinicaltrials.gov/ct2/show/NCT00608881?term=2CARE%20+Huntington&rank=1, accessed Sep. 13, 2016.

Craufurd D, Thompson J C, Snowden J S. Behavioral changes in Huntington Disease. Neuropsychiatry Neuropsychol Behav Neurol. (2001) October-December; 14(4): 219-26.

Exploratory Population Pharmacokinetic Modeling and Simulations With Pridopidine (Report Number: CP-13-013). Pharsight Consulting Services, 10 Jul. 2013.

Guy W. Clinical Global Impression: ECDEU assessment manual for psychopharmacology. (1976) Publication ADM-76-338, US Department of Health, Education, and Welfare Washington, DC: US Government Printing Office. 1976: 217-22.

Hocaoglu M B, Gaffan E A, Ho A K. The Huntington's Disease health-related Quality of Life questionnaire (HDQoL): a disease-specific measure of health-related quality of life. (2012) Clin Genet. February; 81(2):117-22.

Huntington Study Group TREND-HD Investigators. Randomized controlled trial of ethyleicosapentaenoic acid in Huntington disease: the TREND-HD study. Arch Neurol. 2008 December; 65(12):1582-9.

Huntington Study Group. Unified Huntington's Disease Rating Scale: Reliablility and Consistency., Movement Disorders, Vol. 11, No. 2, 1996, pp. 136-142.

Huntington Study Group. Dosage effects of riluzole in Huntington's disease: a multicenter placebo-controlled study. (2003) Neurology. December 9; 61(11):1551-6.

Huntington Study Group. Tetrabenazine as antichorea therapy in Huntington disease: a randomized controlled trial. (2006) Neurology. February 14; 66(3):366-72.

Joffres C, Graham J, Rockwood K. Qualitative analysis of the clinician interview-based impression of change (Plus): methodological issues and implications for clinical research. (2000) Int Psychogeriatr. September; 12(3):403-13.

Johnson A C and Paulsen J S. Huntington's Disease: A Guide for Professionals. (2014) D. Lovecky and K. Tarapata eds. Huntington's Disease Society of Americas (HDSA)

Kieburtz K, Koroshetz W, McDermott M, et al. A randomized, placebo-controlled trial of coenzyme Q10 and remacemide in Huntington's disease. Neurol. 2001 Aug. 14; 57(3):397-404.

Kingma E M, van Duijn E, Timman R, van der Mast R C, Roos R A. Behavioural problems in Huntington's disease using the Problem Behaviours Assessment. (2008) Gen Hosp Psychiatry. March-April; 30(2):155-6

Liang C C, Tanabe L M, Jou S, Chi F, Dauer W T. TorsinA hypofunction causes abnormal twisting movements and sensorimotor circuit neurodegeneration. (2014) J Clin Invest. July; 124(7):3080-92.

Mahant N, McCusker E A, Byth K, Graham S; Huntington Study Group. Huntington's disease: clinical correlates of disability and progression. (2003) Neurology. October 28; 61(8):1085-92.

Marder K, Zhao H, Myers R H, Cudkowicz M, Kayson E, Kieburtz K, Orme C, Paulsen J, Penney J B Jr, Siemers E, Shoulson I. Rate of functional decline in Huntington's disease. Huntington Study Group. (2000) Neurology; 54:452

Mestre T, Ferreira J, Coelho M M, Rosa M, Sampaio C. Therapeutic interventions for symptomatic treatment in Huntington's disease. (2009) Cochrane Database Syst Rev. July 8; (3).

Myers R H, Sax D S, Koroshetz W J, Mastromauro C, Cupples L A, Kiely D K, Pettengill F K, Bird E D. Factors associated with slow progression in Huntington's disease. (1991) Arch Neurol. August 48(8):800-4.

Natesan S, Svensson K A, Reckless G E, Nobrega J N, Barlow K B, Johansson A M, Kapur S. The dopamine stabilizers (S)-(-)-(3-methanesulfonyl-phenyl)-1-propyl-piperidine [(-)-OSU6162] and 4-(3-methanesulfonylphenyl)-1-propyl-piperidine (ACR16) show high in vivo D2 receptor occupancy, antipsychotic-like efficacy, and low potential for motor side effects in the rat. (2006) J Pharmacol Exp Ther. August; 318(2):810-8.

Open-label Extension Study of Pridopidine (ACR16) in the Symptomatic Treatment of Huntington Disease (OPEN-HART), ClinicalTrials.gov Identifier: NCT01306929, clinicaltrials.gov/ct2/show/NCT01306929, accessed Sep. 13, 2016.

Ozelius et al. DYT1 Early-Onset Primary Dystonia. 1999 Apr. 14 [Updated 2014 Jan. 2]. In: Pagon R A, Adam M P, Ardinger H H, et al., editors. GeneReviews® [Internet]. Seattle (Wash.): University of Washington, Seattle; 1993-2016. Available from: www.ncbi.nlm nih.gov/books/NBK1492/Ozelius et al. The early-onset torsion dystonia gene (DYT1) encodes an ATP-binding protein. (1997) Nature Genetics 17.1: 40-48.

Podsiadlo D, Richardson S. The timed "Up & Go": a test of basic functional mobility for frail elderly persons (1991). J Am Geriatr Soc.; 39(2):142-8.

Ponten H, Kullingsjo J, Lagerkvist S, Martin P, Pettersson F, Sonesson C, Waters S, Waters N. In vivo pharmacology of the dopaminergic stabilizer pridopidine. (2010) Eur J Pharmacol. 644(1-3):88-95.

Rao A K, Muratori L, Louis E D, Moskowitz C B, Marder K S. Clinical measurement of mobility and balance impairments in Huntington's disease: validity and responsiveness. (2009) Gait Posture. April; 29(3):433-6.

Segawa, M, and Nomura Y. Genetics and pathophysiology of primary dystonia with special emphasis on DYT1 and DYTS. (2014) Seminars in Neurology. 34(.03):306-311.

Standaert, D G. Update on the Pathology of Dystonia. (2011) Neurobiology of Disease 42.2: 148-151. PMC.

The EuroQol Group. EuroQol—a new facility for the measurement of health-related quality of life. (1990) Health Policy 16:199-208.

Verbeek, D. S., and Gasser, T., Unmet Needs in Dystonia: Genetics and Molecular Biology—How Many Dystonias? (2017) Front. Neurol. 7: 241.

The invention claimed is:

1. A method of treating a subject afflicted with severe dystonia comprising administering to the subject a pharmaceutical composition comprising pridopidine or a pharmaceutically acceptable salt thereof; wherein the subject has Huntington disease, Parkinson disease, Alzheimer disease, Wilson's disease, Multiple Sclerosis, or a genetic dystonias, and wherein the severe dystonia is measured by Unified Dystonia Rating Scale (UDRS), and the human subject has a UDRS rating of ≥4 for at least one body part; or the severe dystonia is measured by Burke-Fahn-Marsden Dystonia Rating Scale (BFMDRS) and the human subject has a BFMDRS rating of ≥4 for at least one body part; or the severe dystonia is measured by Unified Huntington's Disease Rating Scale Total Motor Score (UHDRS-TMS-dystonia), and the human subject has a UHDRS-TMS-dystonia rating of ≥4 for at least one body part.

2. The method of claim 1, wherein the amount of pridopidine is effective to provide a clinically significant improvement in dystonia symptoms.

3. The method of claim 2, wherein the clinically significant improvement in dystonia symptoms is at least a 20% change from baseline in the subject treated with administered pridopidine in comparison to a human patient not treated with pridopidine as measured by the dystonia items of the UHDRS-TMS dystonia scale or the UDRS scale or the Burke-Fahn-Marsden Dystonia Rating Scale.

4. The method of claim 1, wherein the amount of pridopidine is effective to reduce or maintain a level of one or more symptoms of the dystonia in the subject.

5. The method of claim 4, wherein the symptoms are measured by the Burke-Fahn-Marsden Dystonia Rating Scale or the Unified Dystonia Rating Scale.

6. The method of claim 4, wherein the symptoms are measured by the Clinical Global Impression (CGI) scale, Patient Global Assessment score, Visual Analogue Score for pain, Patient Evaluation of Global Response, Burke-Fahn-Marsden Disability Scale (BFMDS), or the Health Related quality of life score (EQ-5D, SF-36).

7. The method of claim 4, wherein the one or more symptoms are selected from the group consisting of: involuntary limb movement or muscle contractions; twisted posture of the limbs or trunk; abnormal fixed posture of the limbs or trunk; talipes equinovarus; turning in of the leg; turning in of the arm; tremor of the hand, head, trunk or arms; dragging of the leg; torticollis; writer's cramp; and dystonia of trunk and/or extremities.

8. The method of claim 1, wherein 22.5 mg to 315 mg pridopidine is administered to the patient per day.

9. The method of claim 8, wherein pridopidine is in the form of a unit dose and the unit dose is administered once daily.

10. The method of claim 8, wherein pridopidine is in the form of a unit dose and the unit dose is administered more than once daily.

11. The method of claim 10, wherein the unit dose is administered twice per day.

12. The method of claim 1, wherein pridopidine is periodically orally administered the periodic administration is oral.

13. The method of claim 1, wherein the subject is afflicted with severe dystonia as a symptom of Huntington disease.

14. The method of claim 13, wherein the subject is afflicted with severe dystonia having a UHDRS-TMS dystonia $\geq 4$.

* * * * *